United States Patent
Hoekstra et al.

(10) Patent No.: US 7,317,005 B2
(45) Date of Patent: *Jan. 8, 2008

(54) TRICYCLIC BENZODIAZEPINES AS VASOPRESSIN RECEPTOR ANTAGONISTS

(75) Inventors: William J. Hoekstra, Chapel Hill, NC (US); Alexey B. Dyatkin, Lansdale, PA (US); Bruce E. Maryanoff, Forest Grove, PA (US); Jay M. Matthews, Lansdale, PA (US)

(73) Assignee: Ortho-McNeil Pharmaceutical, Inc., Raritan, NJ (US)

( * ) Notice: Subject to any disclaimer, the term of this patent is extended or adjusted under 35 U.S.C. 154(b) by 208 days.

This patent is subject to a terminal disclaimer.

(21) Appl. No.: 10/775,675

(22) Filed: Feb. 10, 2004

(65) Prior Publication Data

US 2004/0242866 A1   Dec. 2, 2004

Related U.S. Application Data

(63) Continuation of application No. 09/911,605, filed on Jul. 24, 2001, now Pat. No. 6,713,475, which is a continuation-in-part of application No. 09/468,650, filed on Dec. 21, 1999, now abandoned.

(60) Provisional application No. 60/116,358, filed on Jan. 19, 1999.

(51) Int. Cl.
*A61P 9/00* (2006.01)
*A61K 31/55* (2006.01)
*C07D 487/00* (2006.01)
*C07D 513/00* (2006.01)

(52) U.S. Cl. .................. 514/220; 540/497; 540/559

(58) Field of Classification Search ............... 514/220; 540/497, 559
See application file for complete search history.

(56) References Cited

U.S. PATENT DOCUMENTS

| | | | | |
|---|---|---|---|---|
| 3,732,212 A | 5/1973 | Carabateas | .................. | 540/494 |
| 3,763,183 A | 10/1973 | Carabateas | .................. | 540/561 |
| 3,860,600 A | 1/1975 | Carabateas | .................. | 540/559 |
| 5,516,774 A | 5/1996 | Albright | .................... | 514/220 |
| 5,521,173 A | 5/1996 | Venkatesan et al. | ........ | 514/220 |
| 6,713,475 B2 * | 3/2004 | Hoekstra et al. | ............ | 514/220 |

FOREIGN PATENT DOCUMENTS

EP      0 987 266 A1    3/2000

OTHER PUBLICATIONS

P.A. Van Zwieten, *Progr. Pharmacol. Clin. Pharmacol.*, 1990, 7, 49.
H. Ogawa, *J. Med. Chem.*, 1996, 39, 3547.
G. Fujisawa, *Kidney Int.*, 1993, 44(1), 19.
U. Larsson and R. Carlson, *Acta Chimica Scandinavica*, 1994, 48, 517-525.
Bigge, C. F.; Hays, S.J.; Novak, P.M.; Drummond, J.T.; Johnson, G.; Bobovski, T.P.; *Tel. Lett.*, 1989, 30(39), 5193.
F. Rutjes, *Tetrahedron Lett.*, 1997, 38, 677-680.
International Search Report for PCT/US99/30423 dated Sep. 20, 2000.

* cited by examiner

*Primary Examiner*—Brenda Coleman
(74) *Attorney, Agent, or Firm*—Woodcock Washburn LLP

(57) ABSTRACT

The invention is directed to tricyclic benzodiazepines useful as vasopressin receptor antagonists for treating conditions involving increased vascular resistance and cardiac insufficiency. Pharmaceutical compositions comprising tricyclic benzodiazepines of the present invention and methods of treating conditions such as hypertension, congestive heart failure, cardiac insufficiency, coronary vasospasm, cardiac ischemia, liver cirrhosis, renal vasospasm, renal failure, cerebral edema and ischemia, stroke, thrombosis, or water retention are also disclosed.

46 Claims, No Drawings

TRICYCLIC BENZODIAZEPINES AS VASOPRESSIN RECEPTOR ANTAGONISTS

FIELD OF THE INVENTION

This patent application is a Continuation of Non-Provisional application Ser. No. 09/911,605 filed on Jul. 24, 2001, now issued as U.S. Pat. No. 6,713,475 on Mar. 30, 2004, which is a Continuation-In-Part of Non-Provisional application Ser. No. 09/468,650 filed on Dec. 21, 1999, now abandoned, which claims priority from provisional patent application Ser. No. 60/116,358 filed on Jan. 19, 1999, all of which are hereby incorporated by reference herein.

This invention relates to novel tricyclic vasopressin receptor antagonists. More particularly, the compounds of the present invention interrupt the binding of the peptide hormone vasopressin to its receptors and are therefore useful for treating conditions involving increased vascular resistance and cardiac insufficiency.

BACKGROUND OF THE INVENTION

Vasopressin is a nonapeptide hormone that is secreted primarily from the posterior pituitary gland. The hormone effects its actions through membrane-bound V-1 and V-2 receptor subtypes. The functions of vasopressin include contraction of uterine, bladder, and smooth muscle; stimulation of glycogen breakdown in the liver; release of corticotropin from the anterior pituitary; induction of platelet aggregation; and central nervous system modulation of behaviors and stress responses. The V-1 receptor mediates the contraction of smooth muscle, and hepatic glycogenolytic and central nervous system effects of vasopressin. The V-2 receptor, presumably found only in the kidney, effects the antidiuretic actions of vasopressin via stimulation of adenylate cyclase.

Elevated plasma vasopressin levels appear to play a role in the pathogenesis of congestive heart failure (P. A. Van Zwieten, *Progr. Pharmacol. Clin. Pharmacol.* 1990, 7, 49). As progress toward the treatment of congestive heart failure, nonapeptide vasopressin V-2 receptor antagonists have induced low osmolality aquaresis and decreased peripheral resistance in conscious dogs with congestive heart failure (H. Ogawa, *J. Med. Chem.* 1996, 39, 3547). In certain pathological states, plasma vasopressin levels may be inappropriately elevated for a given osmolality, thereby resulting in renal water retention and hyponatremia. Hyponatremia, associated with edematous conditions (cirrhosis, congestive heart failure, renal failure), can be accompanied by the syndrome of inappropriate secretion of antidiuretic hormone (SIADH). Treatment of SIADH-compromised rats with a vasopressin V-2 antagonist has corrected their existing hyponatremia (G. Fujisawa, *Kidney Int.* 1993, 44(1), 19). Due in part to the contractile actions of vasopressin at the V-1 receptor in the vasculature, vasopressin V-1 antagonists have reduced blood pressure as a potential treatment for hypertension. Thus, vasopressin receptor antagonists could be useful as therapeutics in the conditions of hypertension, congestive heart failure/cardiac insufficiency, coronary vasospasm, cardiac ischemia, liver cirrhosis, renal vasospasm, renal failure, cerebral edema and ischemia, stroke, thrombosis, and water retention.

SUMMARY OF THE INVENTION

The present invention is directed to compounds represented by the following general formulas (I) and (II):

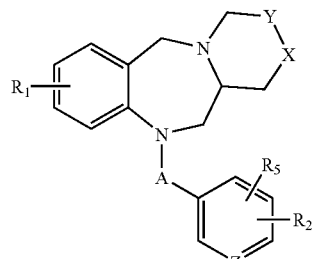

(I)

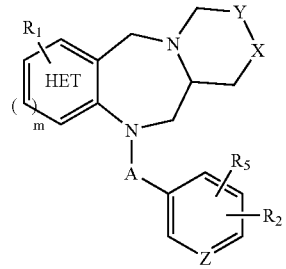

(II)

wherein m is an integer from 0 to 1 such that "HET" in the compound of formula (II) is a stable five- or six-membered monocyclic aromatic ring system composed of carbon atoms and one heteroatom, wherein the heteroatom is selected from N, O or S which may occupy any position in the ring whereby the resulting ring system is stable; for example, thiophene, furan, pyrrole or pyridine;

A is selected from —C(O)—, $SO_2$ or $CH_2$, preferably, A is —C(O)—;

Y is selected from $CH_2$ or CH as part of an olefin;

X is selected from $CH_2$, CH as part of an olefin, $NR_3$, S or O;

with the proviso that if Y is CH as part of an olefin, then X is CH as part of an olefin;

Z is selected from N or CH;

$R_1$ is one to two substituents independently selected from hydrogen, alkyl, alkoxy, halogen, aminoalkyl, oxo or nitro;

Ar is selected from naphthyl, wherein naphthyl is optionally substituted with from one to four (or one to three) substituents independently selected from $C_1$–$C_8$ alkyl, $C_1$–$C_8$ alkoxy, fluorinated $C_1$–$C_8$ alkyl (preferably trifluoromethyl), fluorinated $C_1$–$C_8$ alkoxy (preferably trifluoromethoxy), halogen, cyano, hydroxy, amino, nitro, $C_1$–$C_4$ alkylamino (preferably —NH—$C_1$–$C_4$ alkyl) or $C_1$–$C_4$ dialkylamino (preferably —N—($C_1$–$C_4$ alkyl)$_2$, wherein the alkyl groups on the amino may be the same or different); or phenyl, wherein phenyl is optionally substituted with from one to four (or one to three) substituents independently selected from $C_1$–$C_8$ alkyl, $C_1$–$C_8$ alkoxy, fluorinated $C_1$–$C_8$ alkyl, fluorinated $C_1$–$C_8$ alkoxy, $C_1$–$C_8$ aralkyl (wherein optionally the alkyl or aryl portions are independently substituted and the alkyl portion may be substituted with at least one fluorine and/or the aryl portion may be independently substituted with from one to two substituents selected from halogen, $C_1$–$C_4$ alkyl, $C_1$–$C_6$ alkylthio or hydroxyl), $C_1$–$C_8$ aralkoxy (wherein optionally the alkoxy or aryl portions are independently substituted and the alkoxy portion may be substituted with at least one fluorine and/or the aryl portion may be independently substituted with from one to two substituents selected from halogen, $C_1$–$C_4$ alkyl, $C_1$–$C_6$ alkylthio or hydroxyl), halogen, cyano, hydroxy, amino, nitro, $C_1$–$C_8$ alkylamino, $C_1$–$C_4$ dialkylamino (wherein the alkyl groups on the amino may be the same or different), (halo)$_{1-3}$(C$_1$–C$_8$)alkylthio, C$_1$–C$_8$ alkylsulfonyl, C$_1$–C$_8$ alkylthio, C$_1$–C$_8$ alkylsulfinyl, heteroaryl (optionally substituted with one to two substituents independently selected from C$_1$–C$_8$ alkyl) or phenyl (optionally substituted with from one to two substituents independently selected from C$_1$–C$_4$ alkyl, C$_1$–C$_4$ alkoxy, fluorinated C$_1$–C$_4$ alkyl, fluorinated C$_1$–C$_4$ alkoxy, halogen, cyano, hydroxy, amino, nitro, C$_1$–C$_4$ alkylamino, C$_1$–C$_4$ dialkylamino (wherein the alkyl groups on the amino may be the same or different), C$_1$–C$_4$ alkylsulfonyl, C$_1$–C$_4$ alkylthio, or C$_1$–C$_4$ alkylsulfinyl);

R$_2$ is selected from NR$_4$COAr, NR$_4$CO-heteroaryl, NR$_4$Ar, CH=CH—Ar, CF=CH—Ar, CH=CF—Ar, CCl=CH—Ar, CH=CCl—Ar, CH=CH-heteroaryl, CF=CH-heteroaryl, CH=CF-heteroaryl, —CCl=CH-heteroaryl, CH=CCl-heteroaryl, OCH$_2$—Ar, OCH$_2$-heteroaryl, SCH$_2$—Ar or NR$_4$CH$_2$Ar;

preferably, R$_2$ is selected from NR$_4$COAr, NR$_4$CO-heteroaryl, NR$_4$Ar, CH=CH—Ar, CF=CH—Ar, CH=CF—Ar, CCl=CH—Ar, CH=CCl—Ar, CH=CH-heteroaryl, CF=CH-heteroaryl, CH=CF-heteroaryl, —CCl=CH-heteroaryl or CH=CCl-heteroaryl; more preferably, R$_2$ is NR$_4$COAr; most preferably, R$_2$ is NHCOAr;

R$_3$ is selected from hydrogen, acyl, alkyl, alkoxycarbonyl, alkylsulfonyl or arylsulfonyl;

R$_4$ is selected from hydrogen or C$_1$–C$_4$ alkyl; preferably, R$_4$ is hydrogen or methyl; most preferably, R$_4$ is hydrogen; and R$_5$ is selected from hydrogen, C$_1$–C$_4$ alkyl, C$_1$–C$_4$ alkoxy, chlorine, fluorine, hydroxy, dialkylamino (wherein the alkyl groups on the amino may be the same or different), trifluoromethyl or trifluoromethoxy;

and pharmaceutically acceptable salts thereof.

The compounds of the present invention are vasopressin receptor antagonists useful as aquaretics and, in general, for treating cardiovascular disease.

In one embodiment of the present invention is a compound of the formula (III):

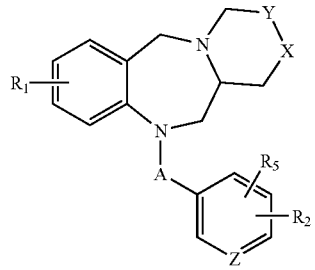

(III)

wherein

Y is selected from CH$_2$ or CH as part of an olefin;

X is selected from CH$_2$, CH as part of an olefin, NR$_3$, S or O;

with the proviso that if Y is CH as part of an olefin, then X is CH as part of an olefin;

R$_1$ is one to two substituents independently selected from hydrogen, C$_1$–C$_4$ alkyl, C$_1$–C$_4$ alkoxy, halogen, amino C$_1$–C$_4$ alkyl, oxo or nitro;

R$_2$ is NHCOAr;

R$_3$ is selected from hydrogen, acyl, alkyl, alkoxycarbonyl, alkylsulfonyl or arylsulfonyl; and R$_5$ is selected from hydrogen, C$_1$–C$_4$ alkyl, C$_1$–C$_4$ alkoxy, chlorine, fluorine, hydroxy, dialkylamino (wherein the alkyl groups on the amino may be the same or different), trifluoromethyl or trifluoromethoxy;

all other variables are as defined previously; and pharmaceutically acceptable salts thereof.

In a class of the invention is a compound wherein

Y is selected from CH$_2$ or CH as part of an olefin;

X is selected from CH$_2$, CH as part of an olefin, S or O;

with the proviso that if Y is CH as part of an olefin, then X is CH as part of an olefin;

A is —C(O)—;

Z is CH;

Ar is phenyl, wherein phenyl is optionally substituted with from one to four (or one to three) substituents independently selected from C$_1$–C$_8$ alkyl, C$_1$–C$_8$ alkoxy, fluorinated C$_1$–C$_8$ alkyl, fluorinated C$_1$–C$_8$ alkoxy, C$_1$–C$_8$ aralkyl (wherein optionally the alkyl or aryl portions are independently substituted and the alkyl portion may be substituted with at least one fluorine and/or the aryl portion may be independently substituted with from one to two substituents selected from halogen, C$_1$–C$_4$ alkyl, C$_1$–C$_6$ alkylthio or hydroxyl), C$_1$–C$_8$ aralkoxy (wherein optionally the alkoxy or aryl portions are independently substituted and the alkoxy portion may be substituted with at least one fluorine and/or the aryl portion may be independently substituted with from one to two substituents selected from halogen, C$_1$–C$_4$ alkyl, C$_1$–C$_6$ alkylthio or hydroxyl), halogen, cyano, hydroxy, amino, nitro, C$_1$–C$_8$ alkylamino, C$_1$–C$_4$ dialkylamino (wherein the alkyl groups on the amino may be the same or different), (halo)$_{1-3}$(C$_1$–C$_8$)alkylthio, C$_1$–C$_8$ alkylsulfonyl, C$_1$–C$_8$ alkylthio, C$_1$–C$_8$ alkylsulfinyl, heteroaryl (optionally substituted with one to two substituents independently selected from C$_1$–C$_8$ alkyl) or phenyl (optionally substituted with from one to two substituents independently selected from C$_1$–C$_4$ alkyl, C$_1$–C$_4$ alkoxy, fluorinated C$_1$–C$_4$ alkyl, fluorinated C$_1$–C$_4$ alkoxy, halogen, cyano, hydroxy, amino, nitro, C$_1$–C$_4$ alkylamino, C$_1$–C$_4$ dialkylamino {wherein the alkyl groups on the amino may be the same or different), C$_1$–C$_4$ alkylsulfonyl, C$_1$–C$_4$ alkylthio, or C$_1$–C$_4$ alkylsulfinyl);

and all other variables are as defined previously;

and pharmaceutically acceptable salts thereof.

In one embodiment of the present invention is a compound of the formula (IV):

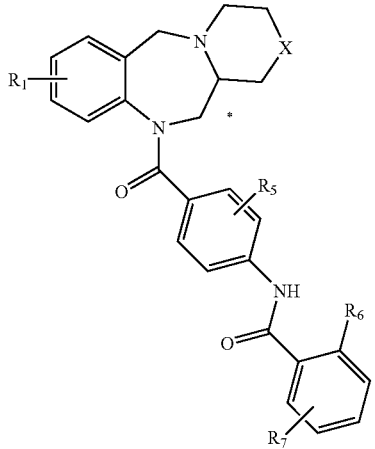

Formula (IV)

wherein

X is selected from CH$_2$, S or O;

R₁ is one to two substituents independently selected from hydrogen, $C_1$–$C_4$ alkyl, $C_1$–$C_4$ alkoxy, halogen, amino $C_1$–$C_4$ alkyl, oxo or nitro;

R₅ is selected from hydrogen, $C_1$–$C_4$ alkyl, $C_1$–$C_4$ alkoxy, chlorine, fluorine, hydroxy, dialkylamino (wherein the alkyl groups on the amino may be the same or different), trifluoromethyl or trifluoromethoxy;

R₆ is selected from the group consisting of hydrogen, $C_1$–$C_4$ alkyl, $C_1$–$C_4$ alkoxy, phenyl (wherein the phenyl is optionally substituted with from one to two substituents independently selected from $C_1$–$C_4$ alkyl, $C_1$–$C_4$ alkoxy, fluorinated $C_1$–$C_4$ alkyl, fluorinated $C_1$–$C_4$ alkoxy, halogen, cyano, hydroxy, amino, nitro, $C_1$–$C_4$ alkylamino, $C_1$–$C_4$ dialkylamino (wherein the alkyl groups on the amino may be the same or different), $C_1$–$C_4$ alkylsulfonyl, $C_1$–$C_4$ alkylthio, or $C_1$–$C_4$ alkylsulfinyl); aralkyl (wherein the alkyl or aryl portions are optionally independently substituted and the alkyl portion may be substituted with at least one fluorine (preferably one) and/or the aryl portion may be independently substituted with from one to two substituents selected from halogen (preferably fluorine or chlorine), $C_1$–$C_4$ alkyl (preferably $C_1$–$C_2$ alkyl), $C_1$–$C_6$ alkylthio (preferably a $C_1$–$C_4$) or hydroxyl), aralkoxy (wherein the alkoxy or aryl portions are optionally independently substituted and the alkoxy portion may be substituted with at least one fluorine (preferably one) and/or the aryl portion may be independently substituted with from one to two substituents selected from halogen (preferably fluorine or chlorine), $C_1$–$C_4$ alkyl (preferably $C_1$–$C_2$ alkyl), $C_1$–$C_6$ alkylthio (preferably a $C_1$–$C_4$) or hydroxyl), heteroaryl (optionally substituted with one to two substituents independently selected from $C_1$–$C_4$ alkyl or halogen), heteroaryl($C_1$–$C_8$)alkyl (wherein the heteroaryl portion is optionally substituted with one to two substituents selected from $C_1$–$C_8$ alkyl), (halo)$_{1-3}$($C_1$–$C_4$) alkylthio and halogen; and R₇ is independently selected from the group consisting of hydrogen, fluorine, chlorine, iodine, hydroxyl, $C_1$–$C_6$ alkyl (preferably $C_1$–$C_4$, and more preferably $C_1$–$C_2$), $C_1$–$C_6$ alkoxy (preferably $C_1$–$C_4$ and more preferably $C_1$–$C_2$), fluorinated $C_1$–$C_6$ alkyl (preferably $C_1$–$C_4$ and more preferably $C_1$–$C_2$) and combinations thereof, wherein R₇ may be one to four independently selected groups;

all other variables are as defined previously; and pharmaceutically acceptable salts thereof.

In one embodiment of the present invention is a compound of the formula (IVa):

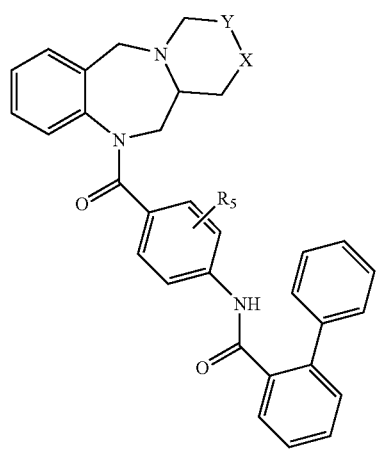

Formula (IVa)

wherein
Y is selected from $CH_2$ or CH as part of an olefin;
X is selected from $CH_2$, CH as part of an olefin, S or O;
with the proviso that if Y is CH as part of an olefin, then X is CH as part of an olefin;
R₅ is one to two substituents independently selected from hydrogen, $C_1$–$C_4$ alkyl, $C_1$–$C_4$ alkoxy, chlorine, fluorine, hydroxyl, dialkylamino (wherein the alkyl groups may be the same or different), trifluoromethyl or trifluoromethoxy;

and pharmaceutically acceptable salts thereof.

The following compounds are additional embodiments of the present invention:

10-[4-[[(2-Biphenyl)carbonyl]amino]benzoyl]-10,11-dihydro-5H-piperidino[2,1-c][1,4]benzodiazepine;

10-[4-[[(2-Biphenyl)carbonyl]amino]benzoyl]-10,11-dihydro-5H-(tetrahydropyridino)[2,1-c][1,4]benzodiazepine;

(RS)-2-Phenyl-N-[4-(1,3,4,12a-tetrahydro-6H-[1,4]thiazino[4,3-a][1,4]-benzodiazepin-11(12H)-yl-carbonyl)phenyl]benzamide;

(S)-2-Phenyl-N-[3-chloro-4-(1,3,4,12a-tetrahydro-6H-[1,4]oxazino[4,3-a][1,4]-benzodiazepin-11(12H)-yl-carbonyl)phenyl]benzamide;

(S)-2-(4-Hydroxyphenyl)-N-[3-chloro-4-(1,3,4,12a-tetrahydro-6H-[1,4]oxazino[4,3-a][1,4]-benzodiazepin-11 (12H)-yl-carbonyl)phenyl]benzamide;

(S)-2-Phenyl-4-hydroxy-N-[3-chloro-4-(1,3,4,12a-tetrahydro-6H-[1,4]oxazino[4,3-a][1,4]-benzodiazepin-11 (12H)-yl-carbonyl)phenyl]benzamide;

(S)-2-(3-Hydroxyphenyl)-N-[3-chloro-4-(1,3,4,12a-tetrahydro-6H-[1,4]oxazino[4,3-a][1,4]-benzodiazepin-11 (12H)-yl-carbonyl)phenyl]benzamide;

(S)-2-Phenyl-5-hydroxy-N-[3-chloro-4-(1,3,4,12a-tetrahydro-6H-[1,4]oxazino[4,3-a][1,4]-benzodiazepin-11 (12H)-yl-carbonyl)phenyl]benzamide;

(RS)-2-(4-Methyl-2-thienyl)-4-fluoro-N-[3-chloro-4-(1,3,4,12a-tetrahydro-6H-[1,4]oxazino[4,3-a][1,4]-benzodiazepin-11(12H)-yl-carbonyl)phenyl]benzamide;

(RS)-2,6-Dimethyl-N-[3-chloro-4-(1,3,4,12a-tetrahydro-6H-[1,4]oxazino[4,3-a][1,4]-benzodiazepin-11(12H)-yl-carbonyl)phenyl]benzamide;

(RS)-2,3-Dimethyl-N-[3-chloro-4-(1,3,4,12a-tetrahydro-6H-[1,4]oxazino[4,3-a][1,4]-benzodiazepin-11(12H)-yl-carbonyl)phenyl]benzamide;

(RS)-2-(4-Methyl-phenyl)-N-[4-(1,3,4,12a-tetrahydro-6H-[1,4]oxazino[4,3-a][1,4]-benzodiazepin-11(12H)-yl-carbonyl)phenyl]benzamide;

(R)-2-Phenyl-N-[3-chloro-4-(1,3,4,12a-tetrahydro-6H-[1,4]oxazino[4,3-a][1,4]-benzodiazepin-11(12H)-yl-carbonyl)phenyl]benzamide;

(RS)-2-Phenyl-N-[3-methoxy-4-(1,3,4,12a-tetrahydro-6H-[1,4]oxazino[4,3-a][1,4]-benzodiazepin-11(12H)-yl-carbonyl)phenyl]benzamide;

(RS)-2-Phenyl-N-[2-methoxy-4-(1,3,4,12a-tetrahydro-6H-[1,4]oxazino[4,3-a][1,4]-benzodiazepin-11(12H)-yl-carbonyl)phenyl]benzamide;

(RS)-2,3,4,5-Tetrafluoro-N-[3-chloro-4-(1,3,4,12a-tetrahydro-6H-[1,4]oxazino[4,3-a][1,4]-benzodiazepin-11 (12H)-yl-carbonyl)phenyl]benzamide;

(RS)-2-Chloro-5-trifluoromethyl-N-[3-chloro-4-(1,3,4,12a-tetrahydro-6H-[1,4]oxazino[4,3-a][1,4]-benzodiazepin-11(12H)-yl-carbonyl)phenyl]benzamide;

(RS)-2-Fluoro-3-chloro-N-[3-chloro-4-(1,3,4,12a-tetrahydro-6H-[1,4]oxazino[4,3-a][1,4]-benzodiazepin-11 (12H)-yl-carbonyl)phenyl]benzamide;

(RS)-2-(Difluoromethylthio)-N-[3-chloro-4-(1,3,4,12a-tetrahydro-6H-[1,4]oxazino[4,3-a][1,4]-benzodiazepin-11(12H)-yl-carbonyl)phenyl]benzamide;

(RS)-2-Phenyl-N-[4-(1,3,4,12a-tetrahydro-6H-[1,4]oxazino[4,3-a][1,4]-benzodiazepin-11(12H)-yl-carbonyl)phenyl]benzamide;

(RS)-2-Phenyl-N-[3-chloro-4-(1,3,4,12a-tetrahydro-6H-[1,4]oxazino[4,3-a][1,4]-5-oxo-benzodiazepin-11(12H)-yl-carbonyl)phenyl]benzamide;

(RS)-2-Phenyl-N-[2-hydroxy-4-(1,3,4,12a-tetrahydro-6H-[1,4]oxazino[4,3-a][1,4]-benzodiazepin-11(12H)-yl-carbonyl)phenyl]benzamide;

(RS)-2-Phenyl-N-[3-hydroxy-4-(1,3,4,12a-tetrahydro-6H-[1,4]oxazino[4,3-a][1,4]-benzodiazepin-11(12H)-yl-carbonyl)phenyl]benzamide;

(RS)-2-Methyl-N-[3-chloro-4-(1,3,4,12a-tetrahydro-6H-[1,4]oxazino[4,3-a][1,4]-benzodiazepin-11(12H)-yl-carbonyl)phenyl]benzamide;

(RS)-2-(4-Methyl-phenyl)-N-[3-chloro-4-(1,3,4,12a-tetrahydro-6H-[1,4]oxazino[4,3-a][1,4]-benzodiazepin-11(12H)-yl-carbonyl)phenyl]benzamide;

(RS)-2-Methyl-N-[4-(1,3,4,12a-tetrahydro-6H-[1,4]oxazino[4,3-a][1,4]-benzodiazepin-11(12H)-yl-carbonyl)phenyl]benzamide;

(RS)-2-Methyl-N-[3-methyl-4-(1,3,4,12a-tetrahydro-6H-[1,4]oxazino[4,3-a][1,4]-benzodiazepin-11(12H)-yl-carbonyl)phenyl]benzamide;

(RS)-2-(4-Methyl-phenyl)-N-[3-methyl-4-(1,3,4,12a-tetrahydro-6H-[1,4]oxazino[4,3-a][1,4]-benzodiazepin-11(12H)-yl-carbonyl)phenyl]benzamide;

(RS)-2-Phenyl-N-[3-methyl-4-(1,3,4,12a-tetrahydro-6H-[1,4]oxazino[4,3-a][1,4]-benzodiazepin-11(12H)-yl-carbonyl)phenyl]benzamide;

(RS)-2-(4-Methyl-phenyl)-N-[3-fluoro-4-(1,3,4,12a-tetrahydro-6H-[1,4]oxazino[4,3-a][1,4]-benzodiazepin-11(12H)-yl-carbonyl)phenyl]benzamide;

(RS)-2-Phenyl-N-[4-(8-methoxy-1,3,4,12a-tetrahydro-6H-[1,4]thiazino[4,3-a][1,4]-benzodiazepin-11(12H)-yl-carbonyl)phenyl]benzamide;

(RS)-2-Phenyl-N-[4-(8-fluoro-1,3,4,12a-tetrahydro-6H-[1,4]thiazino[4,3-a][1,4]-benzodiazepin-11(12H)-yl-carbonyl)phenyl]benzamide;

(RS)-2-Phenyl-N-[4-(8,9-dimethoxy-1,3,4,12a-tetrahydro-6H-[1,4]thiazino[4,3-a][1,4]-benzodiazepin-11(12H)-yl-carbonyl)phenyl]benzamide;

(RS)-2-Phenyl-N-[4-(9-chloro-1,3,4,12a-tetrahydro-6H-[1,4]thiazino[4,3-a][1,4]-benzodiazepin-11(12H)-yl-carbonyl)phenyl]benzamide;

(RS)-2-Phenyl-N-[4-(8,9-difluoro-1,3,4,12a-tetrahydro-6H-[1,4]thiazino[4,3-a][1,4]-benzodiazepin-11(12H)-yl-carbonyl)phenyl]benzamide;

(RS)-2-Phenyl-N-[4-(8-methyl-1,3,4,12a-tetrahydro-6H-[1,4]thiazino[4,3-a][1,4]-benzodiazepin-11(12H)-yl-carbonyl)phenyl]benzamide;

(RS)-2-Phenyl-N-[4-(8-chloro-1,3,4,12a-tetrahydro-6H-[1,4]thiazino[4,3-a][1,4]-benzodiazepin-11(12H)-yl-carbonyl)phenyl]benzamide;

(RS)-2-Phenyl-N-[3-chloro-4-(8-fluoro-1,3,4,12a-tetrahydro-6H-[1,4]thiazino[4,3-a][1,4]-benzodiazepin-11(12H)-yl-carbonyl)phenyl]benzamide;

(RS)-2-Phenyl-N-[4-(10-methyl-1,3,4,12a-tetrahydro-6H-[1,4]thiazino[4,3-a][1,4]-benzodiazepin-11(12H)-yl-carbonyl)phenyl]benzamide;

(RS)-2-Phenyl-N-[4-(10-methoxy-1,3,4,12a-tetrahydro-6H-[1,4]thiazino[4,3-a][1,4]-benzodiazepin-11(12H)-yl-carbonyl)phenyl]benzamide;

(RS)-3,5-Dimethyl-N-[3-chloro-4-(1,3,4,12a-tetrahydro-6H-[1,4]thiazino[4,3-a][1,4]-benzodiazepin-11(12H)-yl-carbonyl)phenyl]benzamide;

(RS)-2-Iodo-3-methyl-N-[3-chloro-4-(1,3,4,12a-tetrahydro-6H-[1,4]thiazino[4,3-a][1,4]-benzodiazepin-11(12H)-yl-carbonyl)phenyl]benzamide;

(RS)-3,5-Dichloro-N-[3-chloro-4-(1,3,4,12a-tetrahydro-6H-[1,4]thiazino[4,3-a][1,4]-benzodiazepin-11(12H)-yl-carbonyl)phenyl]benzamide;

(RS)-2-Methyl-3-iodo-N-[3-chloro-4-(1,3,4,12a-tetrahydro-6H-[1,4]thiazino[4,3-a][1,4]-benzodiazepin-11(12H)-yl-carbonyl)phenyl]benzamide;

(RS)-2-(2-Fluoro-phenyl)-N-[4-(1,3,4,12a-tetrahydro-6H-[1,4]thiazino[4,3-a][1,4]-benzodiazepin-11(12H)-yl-carbonyl)phenyl]benzamide;

(S)-2-Phenyl-N-[3-dimethylamino-4-(1,3,4,12a-tetrahydro-6H-[1,4]thiazino[4,3-a][1,4]-benzodiazepin-11(12H)-yl-carbonyl)phenyl]benzamide;

(S)-2-Phenyl-N-[3-chloro-4-(1,3,4,12a-tetrahydro-6H-[1,4]thiazino[4,3-a][1,4]-benzodiazepin-11(12H)-yl-carbonyl)phenyl]benzamide;

and pharmaceutically acceptable salts thereof.

Additional exemplified embodiments of the present invention include the compounds:

10-[4-[[(2-Biphenyl)carbonyl]amino]benzoyl]-10,11-dihydro-1,2-methanopyrrolidino[2,1-c][1,4]benzodiazepine;

(RS)-2-(3-Thienyl)-N-[4-(1,3,4,12a-tetrahydro-6H-[1,4]thiazino[4,3-a][1,4]-benzodiazepin-11(12H)-yl-carbonyl)phenyl]benzamide;

(RS)-2-(3-Thienyl)-N-[3-chloro-4-(1,3,4,12a-tetrahydro-6H-[1,4]thiazino[4,3-a][1,4]-benzodiazepin-11(12H)-yl-carbonyl)phenyl]benzamide;

(RS)-2-(3-Thienyl)-N-[3-fluoro-4-(1,3,4,12a-tetrahydro-6H-[1,4]thiazino[4,3-a][1,4]-benzodiazepin-11(12H)-yl-carbonyl)phenyl]benzamide;

(RS)-2-(2-Thienyl)-N-[4-(1,3,4,12a-tetrahydro-6H-[1,4]thiazino[4,3-a][1,4]-benzodiazepin-11(12H)-yl-carbonyl)phenyl]benzamide;

(RS)-2-(4-Methyl-2-thienyl)-N-[4-(1,3,4,12a-tetrahydro-6H-[1,4]thiazino[4,3-a][1,4]-benzodiazepin-11(12H)-yl-carbonyl)phenyl]benzamide;

(RS)-2-(4-Methyl-2-thienyl)-N-[4-(1,3,4,12a-tetrahydro-6H-[1,4]oxazino[4,3-a][1,4]-benzodiazepin-11(12H)-yl-carbonyl)phenyl]benzamide;

(RS)-2-Phenyl-N-[4-(1,3,4,12a-tetrahydro-2,2-dioxo-6H-[1,4]thiazino[4,3-a][1,4]-benzodiazepin-11(12H)-yl-carbonyl)phenyl]benzamide;

(RS)-2-Phenyl-N-[3-chloro-4-(1,3,4,12a-tetrahydro-2-methyl-6H-[1,4]pyrazino[4,3-a][1,4]-benzodiazepin-11(12H)-yl-carbonyl)phenyl]benzamide;

(RS)-2-Phenyl-N-[4-(1,3,4,12a-tetrahydro-2-benzyl-6H-[1,4]pyrazino[4,3-a][1,4]-benzodiazepin-11(12H)-yl-carbonyl)phenyl]benzamide;

(RS)-2-Phenyl-N-[4-(1,3,4,12a-tetrahydro-6H-[1,4]pyrazino[4,3-a][1,4]-benzodiazepin-11(12H)-yl-carbonyl)phenyl]benzamide;

(RS)-2-Phenyl-N-[4-(1,3,4,12a-tetrahydro-2-formyl-6H-[1,4]pyrazino[4,3-a][1,4]-benzodiazepin-11(12H)-yl-carbonyl)phenyl]benzamide;

(RS)-2-Phenyl-N-[3-chloro-4-(1,3,4,12a-tetrahydro-2-isopropyl-6H-[1,4]pyrazino[4,3-a][1,4]-benzodiazepin-11(12H)-yl-carbonyl)phenyl]benzamide;

(RS)-2-Methyl-N-[3-chloro-4-(1,3,4,12a-tetrahydro-2-methyl-6H-[1,4]pyrazino[4,3-a][1,4]-benzodiazepin-11(12H)-yl-carbonyl)phenyl]benzamide;

(RS)-2,3-Dimethyl-N-[3-chloro-4-(1,3,4,12a-tetrahydro-2-methyl-6H-[1,4]pyrazino[4,3-a][1,4]-benzodiazepin-11(12H)-yl-carbonyl)phenyl]benzamide;
(RS)-2,6-Dimethyl-N-[3-chloro-4-(1,3,4,12a-tetrahydro-2-methyl-6H-[1,4]pyrazino[4,3-a][1,4]-benzodiazepin-11(12H)-yl-carbonyl)phenyl]benzamide;
(RS)-2-Fluoro-N-[3-chloro-4-(1,3,4,12a-tetrahydro-2-methyl-6H-[1,4]pyrazino[4,3-a][1,4]-benzodiazepin-11(12H)-yl-carbonyl)phenyl]benzamide;
(RS)-2-Fluoro-3-chloro-N-[3-chloro-4-(1,3,4,12a-tetrahydro-2-methyl-6H-[1,4]pyrazino[4,3-a][1,4]-benzodiazepin-11(12H)-yl-carbonyl)phenyl]benzamide;
(RS)-2-(4-Methyl-phenyl)-N-[3-chloro-4-(1,3,4,12a-tetrahydro-2-methyl-6H-[1,4]pyrazino[4,3-a][1,4]-benzodiazepin-11(12H)-yl-carbonyl)phenyl]benzamide;
(RS)-2-(4-Methoxy-phenyl)-N-[3-chloro-4-(1,3,4,12a-tetrahydro-2-methyl-6H-[1,4]pyrazino[4,3-a][1,4]-benzodiazepin-11(12H)-yl-carbonyl)phenyl]benzamide;
(RS)-2-(3-Methoxy-phenyl)-N-[3-chloro-4-(1,3,4,12a-tetrahydro-2-methyl-6H-[1,4]pyrazino[4,3-a][1,4]-benzodiazepin-11(12H)-yl-carbonyl)phenyl]benzamide;
(RS)-2-Phenyl-N-[4-(1,3,4,12a-tetrahydro-2-methyl-6H-[1,4]pyrazino[4,3-a][1,4]-benzodiazepin-11(12H)-yl-carbonyl)phenyl]benzamide;
(RS)-2-Phenyl-N-[3-fluoro-4-(1,3,4,12a-tetrahydro-2-methyl-6H-[1,4]pyrazino[4,3-a][1,4]-benzodiazepin-11(12H)-yl-carbonyl)phenyl]benzamide;
(RS)-2-Methyl-N-[2-methoxy-4-(1,3,4,12a-tetrahydro-2-methyl-6H-[1,4]pyrazino[4,3-a][1,4]-benzodiazepin-11(12H)-yl-carbonyl)phenyl]benzamide;
(RS)-2-Phenyl-N-[2-methoxy-4-(1,3,4,12a-tetrahydro-2-methyl-6H-[1,4]pyrazino[4,3-a][1,4]-benzodiazepin-11(12H)-yl-carbonyl)phenyl]benzamide;
(RS)-2-(4-Methyl-phenyl)-N-[2-methoxy-4-(1,3,4,12a-tetrahydro-2-methyl-6H-[1,4]pyrazino[4,3-a][1,4]-benzodiazepin-11(12H)-yl-carbonyl)phenyl]benzamide;
(RS)-2-Methyl-N-[3-trifluoromethyl-4-(1,3,4,12a-tetrahydro-2-methyl-6H-[1,4]pyrazino[4,3-a][1,4]-benzodiazepin-11(12H)-yl-carbonyl)phenyl]benzamide;
(RS)-2-Phenyl-N-[3-trifluoromethyl-4-(1,3,4,12a-tetrahydro-2-methyl-6H-[1,4]pyrazino[4,3-a][1,4]-benzodiazepin-11(12H)-yl-carbonyl)phenyl]benzamide;
(RS)-2-(4-Methyl-phenyl)-N-[3-trifluoromethyl-4-(1,3,4,12a-tetrahydro-2-methyl-6H-[1,4]pyrazino[4,3-a][1,4]-benzodiazepin-11(12H)-yl-carbonyl)phenyl]benzamide;
(RS)-2-Methyl-N-[2-methyl-4-(1,3,4,12a-tetrahydro-2-methyl-6H-[1,4]pyrazino[4,3-a][1,4]-benzodiazepin-11(12H)-yl-carbonyl)phenyl]benzamide;
(RS)-2-Phenyl-N-[2-methyl-4-(1,3,4,12a-tetrahydro-2-methyl-6H-[1,4]pyrazino[4,3-a][1,4]-benzodiazepin-11(12H)-yl-carbonyl)phenyl]benzamide;
(RS)-2-(4-Methyl-phenyl)-N-[2-methyl-4-(1,3,4,12a-tetrahydro-2-methyl-6H-[1,4]pyrazino[4,3-a][1,4]-benzodiazepin-11(12H)-yl-carbonyl)phenyl]benzamide;
(RS)-2-Methyl-N-[2,6-dimethyl-4-(1,3,4,12a-tetrahydro-2-methyl-6H-[1,4]pyrazino[4,3-a][1,4]-benzodiazepin-11(12H)-yl-carbonyl)phenyl]benzamide;
(RS)-2-Phenyl-N-[2,6-dimethyl-4-(1,3,4,12a-tetrahydro-2-methyl-6H-[1,4]pyrazino[4,3-a][1,4]-benzodiazepin-11(12H)-yl-carbonyl)phenyl]benzamide;
(RS)-2-(4-Methyl-phenyl)-N-[2,6-dimethyl-4-(1,3,4,12a-tetrahydro-2-methyl-6H-[1,4]pyrazino[4,3-a][1,4]-benzodiazepin-11(12H)-yl-carbonyl)phenyl]benzamide;
(RS)-2-Methyl-N-[3-methoxy-4-(1,3,4,12a-tetrahydro-2-methyl-6H-[1,4]pyrazino[4,3-a][1,4]-benzodiazepin-11(12H)-yl-carbonyl)phenyl]benzamide;
(RS)-2-Phenyl-N-[3-methoxy-4-(1,3,4,12a-tetrahydro-2-methyl-6H-[1,4]pyrazino[4,3-a][1,4]-benzodiazepin-11(12H)-yl-carbonyl)phenyl]benzamide;
(RS)-2-(4-Methyl-phenyl)-N-[3-methoxy-4-(1,3,4,12a-tetrahydro-2-methyl-6H-[1,4]pyrazino[4,3-a][1,4]-benzodiazepin-11(12H)-yl-carbonyl)phenyl]benzamide;
(RS)-2-Methyl-N-[4-(1,3,4,12a-tetrahydro-2-methyl-6H-[1,4]pyrazino[4,3-a][1,4]-benzodiazepin-11(12H)-yl-carbonyl)phenyl]benzamide;
(RS)-2-Methyl-N-[3-fluoro-4-(1,3,4,12a-tetrahydro-2-methyl-6H-[1,4]pyrazino[4,3-a][1,4]-benzodiazepin-11(12H)-yl-carbonyl)phenyl]benzamide;
(RS)-2-Methyl-N-[3-methyl-4-(1,3,4,12a-tetrahydro-2-methyl-6H-[1,4]pyrazino[4,3-a][1,4]-benzodiazepin-11(12H)-yl-carbonyl)phenyl]benzamide;
(RS)-2-Phenyl-N-[3-methyl-4-(1,3,4,12a-tetrahydro-2-methyl-6H-[1,4]pyrazino[4,3-a][1,4]-benzodiazepin-11(12H)-yl-carbonyl)phenyl]benzamide;
(RS)-2-Methyl-N-[3-chloro-4-(1,3,4,12a-tetrahydro-2-(2,2,2-trifluoroethyl)-6H-[1,4]pyrazino[4,3-a][1,4]-benzodiazepin-11(12H)-yl-carbonyl)phenyl]benzamide;
(RS)-2-Phenyl-N-[3-chloro-4-(1,3,4,12a-tetrahydro-2-(2,2,2-trifluoroethyl)-6H-[1,4]pyrazino[4,3-a][1,4]-benzodiazepin-11(12H)-yl-carbonyl)phenyl]benzamide;
(RS)-2-Chloro-N-[3-chloro-4-(1,3,4,12a-tetrahydro-2-methyl-6H-[1,4]pyrazino[4,3-a][1,4]-benzodiazepin-11(12H)-yl-carbonyl)phenyl]benzamide;
(RS)-2,3,4,5-Tetrafluoro-N-[3-chloro-4-(1,3,4,12a-tetrahydro-2-methyl-6H-[1,4]pyrazino[4,3-a][1,4]-benzodiazepin-11(12H)-yl-carbonyl)phenyl]benzamide;
(RS)-2-Methyl-5-fluoro-N-[3-chloro-4-(1,3,4,12a-tetrahydro-2-methyl-6H-[1,4]pyrazino[4,3-a][1,4]-benzodiazepin-11(12H)-yl-carbonyl)phenyl]benzamide;
(RS)-2-Methyl-3-chloro-N-[3-chloro-4-(1,3,4,12a-tetrahydro-2-methyl-6H-[1,4]pyrazino[4,3-a][1,4]-benzodiazepin-11(12H)-yl-carbonyl)phenyl]benzamide;
(RS)-2-Fluoro-5-methyl-N-[3-chloro-4-(1,3,4,12a-tetrahydro-2-methyl-6H-[1,4]pyrazino[4,3-a][1,4]-benzodiazepin-11(12H)-yl-carbonyl)phenyl]benzamide;
(RS)-2,3-Dichloro-N-[3-chloro-4-(1,3,4,12a-tetrahydro-2-methyl-6H-[1,4]pyrazino[4,3-a][1,4]-benzodiazepin-11(12H)-yl-carbonyl)phenyl]benzamide;
(RS)-2,6-Dichloro-N-[3-chloro-4-(1,3,4,12a-tetrahydro-2-methyl-6H-[1,4]pyrazino[4,3-a][1,4]-benzodiazepin-11(12H)-yl-carbonyl)phenyl]benzamide;
(RS)-2,6-Difluoro-N-[3-chloro-4-(1,3,4,12a-tetrahydro-2-methyl-6H-[1,4]pyrazino[4,3-a][1,4]-benzodiazepin-11(12H)-yl-carbonyl)phenyl]benzamide;
(RS)-2-Phenyl-5-fluoro-N-[3-chloro-4-(1,3,4,12a-tetrahydro-2-methyl-6H-[1,4]pyrazino[4,3-a][1,4]-benzodiazepin-11(12H)-yl-carbonyl)phenyl]benzamide;
(RS)-2,3-Difluoro-N-[3-chloro-4-(1,3,4,12a-tetrahydro-2-methyl-6H-[1,4]pyrazino[4,3-a][1,4]-benzodiazepin-11(12H)-yl-carbonyl)phenyl]benzamide;
(RS)-2-Methyl-3-fluoro-N-[3-chloro-4-(1,3,4,12a-tetrahydro-2-methyl-6H-[1,4]pyrazino[4,3-a][1,4]-benzodiazepin-11(12H)-yl-carbonyl)phenyl]benzamide;
(RS)-2-Methyl-5-fluoro-N-[3-chloro-4-(1,3,4,12a-tetrahydro-6H-[1,4]thiazino[4,3-a][1,4]-benzodiazepin-11(12H)-yl-carbonyl)phenyl]benzamide;
(RS)-2-Phenyl-5-fluoro-N-[3-chloro-4-(1,3,4,12a-tetrahydro-6H-[1,4]thiazino[4,3-a][1,4]-benzodiazepin-11(12H)-yl-carbonyl)phenyl]benzamide;
(RS)-2-Phenyl-4-fluoro-N-[3-chloro-4-(1,3,4,12a-tetrahydro-6H-[1,4]thiazino[4,3-a][1,4]-benzodiazepin-11(12H)-yl-carbonyl)phenyl]benzamide;

(RS)-2-Phenyl-N-[3-fluoro-4-(1,3,4,12a-tetrahydro-6H-[1,4]thiazino[4,3-a][1,4]-benzodiazepin-11(12H)-yl-carbonyl)phenyl]benzamide;

(RS)-2-Phenyl-N-[3-methyl-4-(1,3,4,12a-tetrahydro-6H-[1,4]thiazino[4,3-a][1,4]-benzodiazepin-11(12H)-yl-carbonyl)phenyl]benzamide;

(RS)-2-Phenyl-N-[3-methoxy-4-(1,3,4,12a-tetrahydro-6H-[1,4]thiazino[4,3-a][1,4]-benzodiazepin-11(12H)-yl-carbonyl)phenyl]benzamide;

(RS)-2-Phenyl-N-[3-hydroxy-4-(1,3,4,12a-tetrahydro-6H-[1,4]thiazino[4,3-a][1,4]-benzodiazepin-11(12H)-yl-carbonyl)phenyl]benzamide;

(RS)-2-Methyl-5-fluoro-N-[3-chloro-4-(1,3,4,12a-tetrahydro-6H-[1,4]oxazino[4,3-a][1,4]-benzodiazepin-11(12H)-yl-carbonyl)phenyl]benzamide;

(RS)-2-Phenyl-5-fluoro-N-[3-chloro-4-(1,3,4,12a-tetrahydro-6H-[1,4]oxazino[4,3-a][1,4]-benzodiazepin-11(12H)-yl-carbonyl)phenyl]benzamide;

(RS)-2-(4-Methoxy-phenyl)-N-[3-chloro-4-(1,3,4,12a-tetrahydro-6H-[1,4]oxazino[4,3-a][1,4]-benzodiazepin-11(12H)-yl-carbonyl)phenyl]benzamide;

(RS)-2-(3-Methoxy-phenyl)-N-[3-chloro-4-(1,3,4,12a-tetrahydro-6H-[1,4]oxazino[4,3-a][1,4]-benzodiazepin-11(12H)-yl-carbonyl)phenyl]benzamide;

(RS)-2-Phenyl-4-fluoro-N-[3-chloro-4-(1,3,4,12a-tetrahydro-6H-[1,4]oxazino[4,3-a][1,4]-benzodiazepin-11(12H)-yl-carbonyl)phenyl]benzamide;

(RS)-2-Phenyl-4-methoxy-N-[3-chloro-4-(1,3,4,12a-tetrahydro-6H-[1,4]oxazino[4,3-a][1,4]-benzodiazepin-11(12H)-yl-carbonyl)phenyl]benzamide;

(RS)-2-Phenyl-5-methoxy-N-[3-chloro-4-(1,3,4,12a-tetrahydro-6H-[1,4]oxazino[4,3-a][1,4]-benzodiazepin-11(12H)-yl-carbonyl)phenyl]benzamide;

and pharmaceutically acceptable salts thereof.

Another embodiment of the present invention is an intermediate compound of the formula (V):

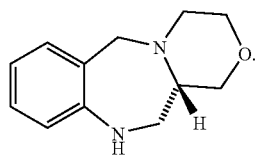

(V)

Yet another embodiment of the present invention is an intermediate compound of the formula (VI):

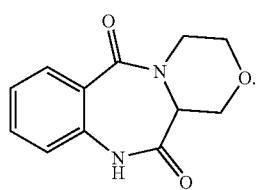

(VI)

Illustrative of the invention is a pharmaceutical composition comprising a pharmaceutically acceptable carrier and any of the compounds described above. Illustrating the invention is a pharmaceutical composition made by mixing any of the compounds described above and a pharmaceutically acceptable carrier. An illustration of the invention is a process for making a pharmaceutical composition comprising mixing any of the compounds described above and pharmaceutically acceptable carrier.

An example of the invention is a method of treating congestive heart failure in a subject in need thereof comprising administering to the subject a therapeutically effective amount of any of the compounds or pharmaceutical compositions described above.

Further exemplifying the invention is the method of treating congestive heart failure, wherein the therapeutically effective amount of the compound is about 0.1 to about 300 mg/kg/day.

An additional illustration of the invention is a method of treating a condition selected from hypertension, congestive heart failure, cardiac insufficiency, coronary vasospasm, cardiac ischemia, liver cirrhosis, renal vasospasm, renal failure, cerebral edema and ischemia, stroke, thrombosis, or water retention in a subject in need thereof comprising administering to the subject a therapeutically effective amount of any of the compounds or pharmaceutical compositions described above. Preferably, the therapeutically effective amount of the compound administered for treating any of these conditions is about 0.1 to about 300 mg/kg/day.

Also included in the invention is the use of any of the compounds described above for the preparation of a medicament for treating a condition selected from hypertension, congestive heart failure, cardiac insufficiency, coronary vasospasm, cardiac ischemia, liver cirrhosis, renal vasospasm, renal failure, cerebral edema and ischemia, stroke, thrombosis, or water retention in a subject in need thereof.

DETAILED DESCRIPTION OF THE INVENTION

The present invention provides tricyclic benzodiazepine compounds which are useful as antagonists of vasopressin. More particularly, the compounds of formula (I) and (II) inhibit the binding of vasopressin to V-1 and V-2 receptors, and are therefore useful in treating conditions with increased vascular resistance. Examples of conditions with increased vascular resistance include, but are not limited to, congestive heart failure, edema, water retaining states, etc. More particularly, the present invention is directed to compounds of the formulas (I) and (II):

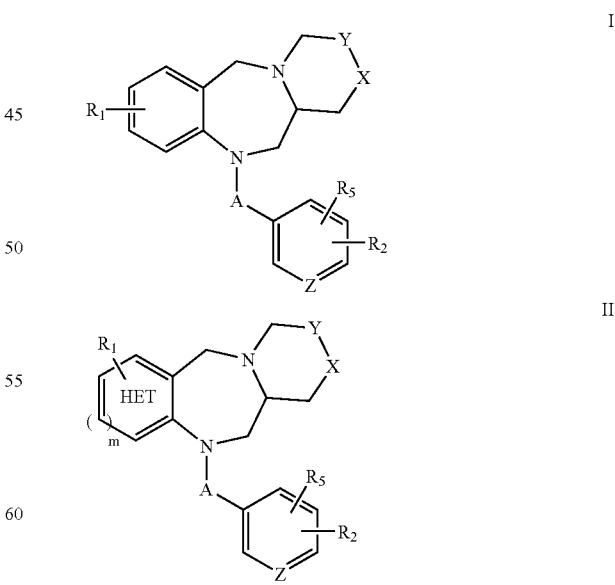

and pharmaceutically acceptable salts thereof;

wherein HET, A, X, Y, Z, $R_1$, $R_2$, $R_5$ and m are as previously defined.

Embodiments of compounds of the present invention further include those compounds of formula (I) wherein Y is selected from $CH_2$ or CH as part of an olefin; X is selected from $CH_2$, CH as part of an olefin, $NR_3$, S, O or $SO_2$; with the proviso that if Y is CH as part of an olefin, then X is CH as part of an olefin.

Embodiments of compounds of the present invention further include those compounds of formula (I) wherein, preferably, $R_1$ is one to two substituents independently selected from hydrogen, $C_1$–$C_4$ alkyl, $C_1$–$C_4$ alkoxy, halogen or oxo.

More preferably, $R_1$ is one to two substituents independently selected from hydrogen, methyl, methoxy, chlorine, fluorine or oxo.

Embodiments of compounds of the present invention further include those compounds of formula (I) wherein, preferably, Ar is phenyl optionally substituted with from one to four substituents independently selected from $C_1$–$C_8$ alkyl, $C_1$–$C_8$ alkoxy, fluorinated $C_1$–$C_8$ alkyl, fluorinated $C_1$–$C_8$ alkoxy, $C_1$–$C_8$ aralkyl (wherein the alkyl portion is optionally substituted with at least one fluorine and the aryl portion is optionally substituted with from one to two substituents independently selected from halogen, $C_1$–$C_4$ alkyl, $C_1$–$C_6$ alkylthio or hydroxy), $C_1$–$C_8$ aralkoxy (wherein the alkoxy portion is optionally substituted with at least one fluorine and the aryl portion is optionally substituted with from one to two substituents independently selected from halogen, $C_1$–$C_4$ alkyl, $C_1$–$C_6$ alkylthio or hydroxy), halogen, cyano, hydroxy, amino, nitro, $C_1$–$C_8$ alkylamino, $C_1$–$C_4$ dialkylamino (wherein the alkyl groups on the amino may be the same or different), $C_1$–$C_8$ alkylsulfonyl, $C_1$–$C_8$ alkylthio, $(halo)_{1-3}(C_1$–$C_8)$alkylthio, $C_1$–$C_8$ alkylsulfinyl, heteroaryl (optionally substituted with one to two substituents independently selected from $C_1$–$C_8$ alkyl or halogen), heteroaryl($C_1$–$C_8$)alkyl (wherein the heteroaryl portion is optionally substituted with one to two substituents independently selected from $C_1$–$C_8$ alkyl) or phenyl (optionally substituted with from one to two substituents independently selected from $C_1$–$C_4$ alkyl, $C_1$–$C_4$ alkoxy, fluorinated $C_1$–$C_4$ alkyl, fluorinated $C_1$–$C_4$ alkoxy, halogen, cyano, hydroxy, amino, nitro, $C_1$–$C_4$ alkylamino, $C_1$–$C_4$ dialkylamino (wherein the alkyl groups on the amino may be the same or different), $C_1$–$C_4$ alkylsulfonyl, $C_1$–$C_4$ alkylthio or $C_1$–$C_4$ alkylsulfinyl).

More preferably, Ar is phenyl optionally substituted with from one to four substituents independently selected from $C_1$–$C_8$ alkyl, $C_1$–$C_8$ alkoxy, fluorinated $C_1$–$C_8$ alkyl, halogen, hydroxy, $(halo)_{1-3}(C_1$–$C_8)$alkylthio, heteroaryl (optionally substituted with one to two substituents independently selected from $C_1$–$C_8$ alkyl or halogen) or phenyl (optionally substituted with from one to two substituents independently selected from $C_1$–$C_4$ alkyl, $C_1$–$C_4$ alkoxy, halogen or hydroxy).

Most preferably, Ar is phenyl optionally substituted with from one to four substituents independently selected from $C_1$–$C_4$ alkyl, $C_1$–$C_4$ alkoxy, fluorinated $C_1$–$C_4$ alkyl, halogen, hydroxy, $(halo)_{1-3}(C_1$–$C_4)$alkylthio, heteroaryl (optionally substituted with one to two substituents independently selected from $C_1$–$C_4$ alkyl or halogen) or phenyl (optionally substituted with from one to two substituents independently selected from $C_1$–$C_4$ alkyl, $C_1$–$C_4$ alkoxy, halogen or hydroxy).

Embodiments of compounds of the present-invention further include those compounds of formula (I) wherein, $R_3$ is selected from hydrogen, acyl, alkyl, aralkyl, alkoxycarbonyl, alkylsulfonyl, fluorinated alkyl or arylsulfonyl.

Preferably, $R_3$ is selected from hydrogen, acyl, $C_1$–$C_8$ alkyl, ar($C_1$–$C_8$)alkyl, $C_1$–$C_8$ alkoxycarbonyl, $C_1$–$C_8$ alkylsulfonyl, fluorinated($C_1$–$C_8$) alkyl or arylsulfonyl.

More preferably, $R_3$ is selected from hydrogen, acyl, $C_1$–$C_4$ alkyl, ar($C_1$–$C_4$)alkyl or trifluoro($C_1$–$C_4$)alkyl.

Most preferably, $R_3$ is selected from hydrogen, formyl, methyl, isopropyl, benzyl or trifluoroethyl.

Embodiments of compounds of the present invention further include those compounds of formula (I) wherein, preferably, $R_5$ is one to two substituents independently selected from hydrogen, $C_1$–$C_4$ alkyl, $C_1$–$C_4$ alkoxy, chlorine, fluorine, hydroxy, dialkylamino (wherein the alkyl groups on the amino may be the same or different), trifluoromethyl or trifluoromethoxy;

More preferably, $R_5$ is one to two substituents independently selected from hydrogen, methyl, methoxy, chlorine, fluorine, hydroxy, dimethylamino or trifluoromethyl.

Embodiments of compounds of the present invention further include those compounds of formula (IV) wherein, preferably, $R_6$ is selected from the group consisting of hydrogen, $C_1$–$C_4$ alkyl, $C_1$–$C_4$ alkoxy, phenyl (wherein the phenyl is optionally substituted with from one to two substituents independently selected from $C_1$–$C_4$ alkyl, $C_1$–$C_4$ alkoxy, fluorinated $C_1$–$C_4$ alkyl, fluorinated $C_1$–$C_4$ alkoxy, halogen, cyano, hydroxy, amino, nitro, $C_1$–$C_4$ alkylamino, $C_1$–$C_4$ dialkylamino (wherein the alkyl groups on the amino may be the same or different), $C_1$–$C_4$ alkylsulfonyl, $C_1$–$C_4$ alkylthio, or $C_1$–$C_4$ alkylsulfinyl); heteroaryl (optionally substituted with one to two substituents independently selected from $C_1$–$C_4$ alkyl or halogen), heteroaryl ($C_1$–$C_8$)alkyl (wherein the heteroaryl portion is optionally substituted with one to two substituents independently selected from $C_1$–$C_8$ alkyl), $(halo)_{1-3}(C_1$–$C_4)$alkylthio and halogen.

More preferably, $R_6$ is selected from the group consisting of hydrogen, $C_1$–$C_4$ alkyl, phenyl (optionally substituted with from one to two substituents independently selected from $C_1$–$C_4$ alkyl, $C_1$–$C_4$ alkoxy, halogen or hydroxy), heteroaryl (optionally substituted with one to two substituents independently selected from $C_1$–$C_4$ alkyl), $(halo)_{1-3}(C_1$–$C_4)$alkylthio and halogen.

Most preferably, $R_6$ is selected from hydrogen, methyl, phenyl (optionally substituted with from one to two substituents independently selected from methyl, methoxy, fluorine or hydroxy), thienyl (optionally substituted with methyl), difluoromethylthio, fluorine, chlorine or iodine.

Embodiments of compounds of the present invention further include those compounds of formula (IV) wherein $R_7$ is one to three substituents independently selected from the group consisting of hydrogen, fluorine, chlorine, iodine, hydroxy, $C_1$–$C_6$ alkyl, $C_1$–$C_6$ alkoxy or fluorinated $C_1$–$C_6$ alkyl.

Preferably, $R_7$ is one to three substituents independently selected from the group consisting of hydrogen, fluorine, chlorine, iodine, hydroxy, $C_1$–$C_4$ alkyl, $C_1$–$C_4$ alkoxy or fluorinated $C_1$–$C_4$ alkyl.

More preferably, $R_7$ is one to three substituents independently selected from the group consisting of hydrogen, fluorine, chlorine, iodine, hydroxy, $C_1$–$C_2$ alkyl, $C_1$–$C_2$ alkoxy or fluorinated $C_1$–$C_2$ alkyl.

Most preferably, $R_7$ is one to three substituents independently selected from the group consisting of hydrogen, fluorine, chlorine, iodine, hydroxy, methyl, methoxy or trifluoromethyl.

Embodiments of the present invention further include an intermediate compound of the formula (VII):

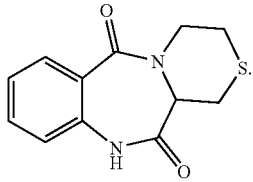

Formula (VII)

Embodiments of the present invention further include an intermediate compound of the formula (VIII):

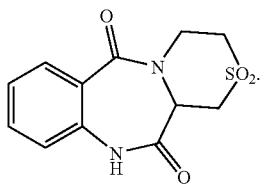

Formula (VIII)

Embodiments of the present invention further include an intermediate compound of the formula (IX):

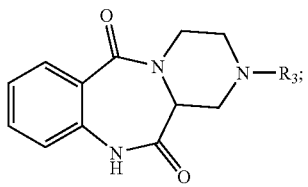

Formula (IX)

wherein $R_3$ is selected from hydrogen, acyl, alkyl, aralkyl, alkoxycarbonyl, alkylsulfonyl, fluorinated alkyl or arylsulfonyl.

Preferably, $R_3$ is selected from hydrogen, acyl, alkyl, aralkyl or trifluoroalkyl.

More preferably, $R_3$ is selected from hydrogen, formyl, methyl, isopropyl, benzyl or trifluoroethyl.

The tricyclic benzodiazepine compounds of the present invention are vasopressin receptor antagonists, in a preferred embodiment, the compounds are orally active. As demonstrated by the results of the pharmacological studies described hereinafter, the compounds show the ability to block vasopressin binding to recombinant V-1 and V-2, and decrease arginine vasopressin-elevated blood pressure in animal models.

The compounds of the present invention may also be present in the form of pharmaceutically acceptable salts. For use in medicine, the salts of the compounds of this invention refer to non-toxic "pharmaceutically acceptable salts." Other salts may, however, be useful in the preparation of compounds according to this invention or of their pharmaceutically acceptable salts. Representative organic or inorganic acids include, but are not limited to, hydrochloric, hydrobromic, hydriodic, perchloric, sulfuric, nitric, phosphoric, acetic, propionic, glycolic, lactic, succinic, maleic, fumaric, malic, tartaric, citric, benzoic, mandelic, methanesulfonic, hydroxyethanesulfonic, benezenesulfonic, oxalic, pamoic, 2-naphthalenesulfonic, p-toluenesulfonic, cyclohexanesulfamic, salicylic, saccharinic or trifluoroacetic acid.

Where the compounds according to this invention have at least one chiral center, they may accordingly exist as enantiomers. Where the compounds possess two or more chiral centers, they may additionally exist as diastereomers. It is to be understood that all such isomers and mixtures thereof are encompassed within the scope of the present invention. Furthermore, some of the crystalline forms for the compounds may exist as polymorphs and as such are intended to be included in the present invention. In addition, some of the compounds may form solvates with water (i.e., hydrates) or common organic solvents, and such solvates are also intended to be encompassed within the scope of this invention.

The term "subject" as used herein, refers to an animal, preferably a mammal, most preferably a human, who has been the object of treatment, observation or experiment.

The term "therapeutically effective amount" as used herein, means that amount of active compound or pharmaceutical agent that elicits the biological or medicinal response in a tissue system, animal or human that is being sought by a researcher, veterinarian, medical doctor or other clinician, which includes alleviation of the symptoms of the disease or disorder being treated.

As used herein, unless otherwise noted alkyl and alkoxy whether used alone or as part of a substituent group, include straight and branched chains having 1 to 8 carbon atoms, or any number within this range. For example, alkyl radicals include methyl, ethyl, n-propyl, isopropyl, n-butyl, isobutyl, sec-butyl, t-butyl, n-pentyl, 3-(2-methyl)butyl, 2-pentyl, 2-methylbutyl, neopentyl, n-hexyl, 2-hexyl and 2-methylpentyl. Alkoxy radicals are oxygen ethers formed from the previously described straight and branched chain or cyclic alkyl groups. Cycloalkyl and cycloalkoxy groups contain 3 to 8 ring carbons and preferably 5 to 7 ring carbons. Similarly, alkenyl and alkynyl groups include straight and branched chains having 2 to 8 carbon atoms, or any number within this range. Cycloalkenyl and cycloalkynyl groups contain 3 to 8 ring carbons, or any number within this range.

The terms "Ar" and "aryl" as used herein are synonymous and refer to an unsubstituted or substituted aromatic group such as phenyl and naphthyl. When the Ar or aryl group is substituted, it may have one to four substituents, which are independently selected from $C_1$–$C_8$ alkyl, $C_1$–$C_8$ alkoxy, fluorinated $C_1$–$C_8$ alkyl (e.g., trifluoromethyl), fluorinated $C_1$–$C_8$ alkoxy (e.g., trifluoromethoxy), halogen, cyano, hydroxy, amino, nitro, $C_1$–$C_4$ alkylamino (i.e., —NH—$C_1$–$C_4$ alkyl), $C_1$–$C_4$ dialkylamino (i.e., —N—($C_1$–$C_4$ alkyl)$_2$ wherein the alkyl groups on the amino can be the same or different). When Ar is phenyl, the phenyl is optionally substituted with from one to four substituents independently selected from $C_1$–$C_8$ alkyl, $C_1$–$C_8$ alkoxy, fluorinated $C_1$–$C_8$ alkyl, fluorinated $C_1$–$C_8$ alkoxy, $C_1$–$C_8$ aralkyl (wherein optionally the alkyl or aryl portions are independently substituted and the alkyl portion may be substituted with at least one fluorine and/or the aryl portion may be independently substituted with from one to two substituents selected from halogen, $C_1$–$C_6$ alkylthio or hydroxyl), $C_1$–$C_8$ aralkoxy (wherein optionally the alkoxy or aryl portions are independently substituted and the alkoxy portion may be substituted with at least one fluorine and/or the aryl portion may be independently substituted with from one to two substituents selected from halogen, $C_1$–$C_6$ alkylthio or hydroxyl), halogen, cyano, hydroxy, amino, nitro, $C_1$–$C_8$ alkylamino, $C_1$–$C_4$ dialkylamino (wherein the alkyl groups on the amino may be the same or different), (halo)$_{1-3}$($C_1$–$C_8$)

alkylthio, $C_1$–$C_8$ alkylsulfonyl, $C_1$–$C_8$ alkylthio, $C_1$–$C_8$ alkylsulfinyl, heteroaryl (optionally substituted with one to two substituents independently selected from $C_1$–$C_8$ alkyl) or phenyl (optionally substituted with from one to two substituents independently selected from $C_1$–$C_4$ alkyl, $C_1$–$C_4$ alkoxy, fluorinated $C_1$–$C_4$ alkyl, fluorinated $C_1$–$C_4$ alkoxy, halogen, cyano, hydroxy, amino, nitro, $C_1$–$C_4$ alkylamino, $C_1$–$C_4$ dialkylamino (wherein the alkyl groups on the amino may be the same or different), $C_1$–$C_4$ alkylsulfonyl, $C_1$–$C_4$ alkylthio, or $C_1$–$C_4$ alkylsulfinyl);

The term "HET" or "heteroaryl" as used herein represents a stable unsubstituted or substituted five- or six-membered monocyclic aromatic ring system or a nine- or ten-membered benzo-fused heteroaromatic ring system which consists of carbon atoms and from one to three heteroatoms selected from N, O or S. The heteroaryl group may be attached at any heteroatom or carbon atom, which results in the creation of a stable structure. Examples of heteroaryl groups include, but are not limited to pyridinyl, pyrazinyl, pyridazinyl, pyrimidinyl, thiophenyl (also referred to as thienyl), furanyl (also referred to as furyl), imidazolyl, isoxazolyl, oxazolyl, pyrazolyl, pyrrolyl, thiazolyl, thiadiazolyl, triazolyl, benzimidazolyl, benzofuranyl, benzothienyl, benzisoxazolyl, benzoxazolyl, benzopyrazolyl, indolyl, benzothiazolyl, benzothiadiazolyl, benzotriazolyl or quinolinyl. Preferred heteroaryl groups include pyridinyl, thiophenyl, furanyl and quinolinyl. When the heteroaryl group is substituted, the heteroaryl group may have one to three substituents, which are independently selected from $C_1$–$C_8$ alkyl, halogen, aryl, heteroaryl, alkoxy, alkylamino, dialkylamino, arylamino, nitro, hydroxy.

The term "aralkyl" means an alkyl group substituted with an aryl group (e.g., benzyl, phenylethyl). Similarly, the term "aralkoxy" indicates an alkoxy group substituted with an aryl group (e.g., benzyloxy). The term aminoalkyl refers to an alkyl group substituted with an amino group (i.e., -alkyl-$NH_2$). The term "alkylamino" refers to an amino group substituted with an alkyl group (i.e., —NH-alkyl). The term "dialkylamino" refers to an amino group which is disubstituted with alkyl groups wherein the alkyl groups can be the same or different (i.e., —N-(alkyl)$_2$). The term "alkylthio" means an alkyl thiol ether group (i.e. —S-alkyl).

The term "acyl" as used herein means an organic radical having 2 to 6 carbon atoms (branched or straight chain) derived from an organic acid by removal of the hydroxyl group.

The term "hydroxyl" is used equivalently with the term "hydroxy" and herein refers to the organic —OH radical.

The term "halogen" shall include iodine, bromine, chlorine and fluorine.

Whenever the term "alkyl" or "aryl" or either of their prefix roots appear in a name of a substituent (e.g., aralkyl, dialkylamino) it shall be interpreted as including those limitations given above for "alkyl" and "aryl." Designated numbers of carbon atoms (e.g., $C_1$–$C_6$) shall refer independently to the number of carbon atoms in an alkyl or cycloalkyl moiety or to the alkyl portion of a larger substituent in which alkyl appears as its prefix root.

It is intended that the definition of any substituent or variable at a particular location in a molecule be independent of its definitions elsewhere in that molecule. It is understood that substituents and substitution patterns on the compounds of this invention can be selected by one of ordinary skill in the art to provide compounds that are chemically stable and that can be readily synthesized by techniques know in the art as well as those methods set forth herein.

In one embodiment of the present invention is a compound of the formula (IV):

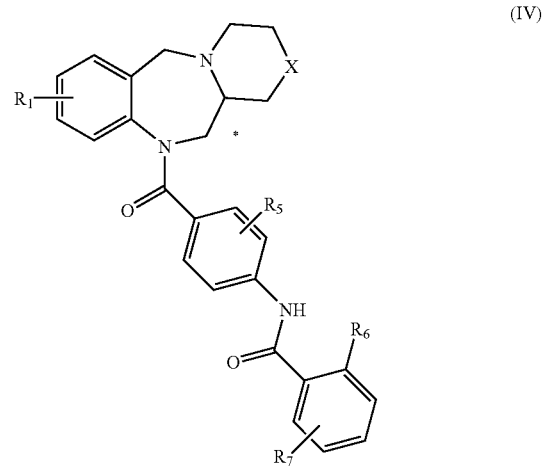

(IV)

wherein
$R_6$ is selected from the group consisting of phenyl (wherein the phenyl is optionally substituted with from one to two substituents independently selected from $C_1$–$C_4$ alkyl, $C_1$–$C_4$ alkoxy, fluorinated $C_1$–$C_4$ alkyl, fluorinated $C_1$–$C_4$ alkoxy, halogen, cyano, hydroxy, amino, nitro, $C_1$–$C_4$ alkylamino, $C_1$–$C_4$ dialkylamino (wherein the alkyl groups may be the same or different), $C_1$–$C_4$ alkylsulfonyl, $C_1$–$C_4$ alkylthio, or $C_1$–$C_4$ alkylsulfinyl); aralkyl (wherein the alkyl or aryl portions are optionally independently substituted and the alkyl portion may be substituted with at least one fluorine (preferably one) and/or the aryl portion may be independently substituted with from one to two substituents selected from halogen (preferably fluorine or chlorine), $C_1$–$C_4$ alkyl (preferably $C_1$–$C_2$ alkyl), $C_1$–$C_6$ alkylthio (preferably a $C_1$–$C_4$) or hydroxyl), and aralkoxy (wherein the alkoxy or aryl portions are optionally independently substituted and the alkoxy portion may be substituted with at least one fluorine (preferably one) and/or the aryl portion may be independently substituted with from one to two substituents selected from halogen (preferably fluorine or chlorine), $C_1$–$C_4$ alkyl (preferably $C_1$–$C_2$ alkyl), $C_1$–$C_6$ alkylthio (preferably a $C_1$–$C_4$) or hydroxyl); and
$R_7$ is independently selected from the group consisting of hydrogen, fluorine, chlorine, hydroxyl, $C_1$–$C_6$ alkyl (preferably $C_1$–$C_4$, and more preferably $C_1$–$C_2$), $C_1$–$C_6$ alkoxy (preferably $C_1$–$C_4$ and more preferably $C_1$–$C_2$) and combinations thereof, wherein $R_7$ maybe one to four independently selected groups.

As used herein, the term "composition" is intended to encompass a product comprising the specified ingredients in the specified amounts, as well as any product which results, directly or indirectly, from combinations of the specified ingredients in the specified amounts.

The utility of the compounds to treat disorders of increased vascular resistance can be determined according to the procedures described herein. The present invention, therefore provides, a method of treating vascular resistance disorders in a subject in need thereof which comprises administering any of the compounds as defined herein in a quantity effective to treat vascular resistance disorders. A compound may be administered to a patient in need of treatment by any conventional route of administration including, but not limited to oral, nasal, sublingual, ocular, transdermal, rectal, vaginal and parenteral (i.e. subcutaneous, intramuscular, intradermal, intravenous etc.).

The present invention also provides pharmaceutical compositions comprising one or more compounds of this invention in association with a pharmaceutically acceptable carrier.

To prepare the pharmaceutical compositions of this invention, one or more compounds of formula (I) or (II) or salt thereof as the active ingredient, is intimately admixed with a pharmaceutical carrier according to conventional pharmaceutical compounding techniques, which carrier may take a wide variety of forms depending of the form of preparation desired for administration (e.g. oral or parenteral such as intramuscular). Suitable pharmaceutically acceptable carriers are well known in the art. Descriptions of some of these pharmaceutically acceptable carriers may be found in *The Handbook of Pharmaceutical Excipients*, published by the American Pharmaceutical Association and the Pharmaceutical Society of Great Britain.

Methods of formulating pharmaceutical compositions have been described in numerous publications such as *Pharmaceutical Dosage Forms: Tablets, Second Edition, Revised and Expanded*, Volumes 1–3, edited by Lieberman et al; *Pharmaceutical Dosage Forms: Parenteral Medications*, Volumes 1–2, edited by Avis et al; and *Pharmaceutical Dosage Forms: Disperse Systems*, Volumes 1–2, edited by Lieberman et al; published by Marcel Dekker, Inc.

In preparing a pharmaceutical composition of the present invention in liquid dosage form for oral, topical and parenteral administration, any of the usual pharmaceutical media or excipients may be employed. Thus, for liquid dosage forms, such as suspensions (i.e. colloids, emulsions and dispersions) and solutions, suitable carriers and additives include but are not limited to pharmaceutically acceptable wetting agents, dispersants, flocculation agents, thickeners, pH control agents (i.e. buffers), osmotic agents, coloring agents, flavors, fragrances, preservatives (i.e. to control microbial growth, etc.) and a liquid vehicle may be employed. Not all of the components listed above will be required for each liquid dosage form.

In solid oral preparations such as, for example, powders, granules, capsules, caplets, gelcaps, pills and tablets (each including immediate release, timed release and sustained release formulations), suitable carriers and additives include but are not limited to diluents, granulating agents, lubricants, binders, glidants, disintegrating agents and the like. Because of their ease of administration, tablets and capsules represent the most advantageous oral dosage unit form, in which case solid pharmaceutical carriers are obviously employed. If desired, tablets may be sugar coated, gelatin coated, film coated or enteric coated by standard techniques.

The pharmaceutical compositions herein will contain, per dosage unit, e.g., tablet, capsule, powder, injection, teaspoonful and the like, an amount of the active ingredient necessary to deliver an effective dose as described above. The pharmaceutical compositions herein will contain, per unit dosage unit, e.g., tablet, capsule, powder, injection, suppository, teaspoonful and the like, of from about 0.03 mg to 100 mg/kg (preferably from about 0.1–30 mg/kg) and may be given at a dosage of from about 0.1–300 mg/kg/day (preferably about 1–50 mg/kg/day and more preferably about 0.03 to 10 mg/kg/day). Preferably, for the method of treating vascular resistance disorders described in the present invention using any of the compounds as defined herein, the dosage form will contain a pharmaceutically acceptable carrier containing between about 0.01 mg and 100 mg, more preferably about 5 to 50 mg, of the compound, and may be constituted into any form suitable for the mode of administration selected. The dosages, however, may be varied depending upon the requirement of the patients, the severity of the condition being treated and the compound being employed. The use of either daily administration or post-periodic dosing may be employed.

Preferably these compositions are in unit dosage forms from such as tablets, pills, capsules, powders, granules, lozenges, sterile parenteral solutions or suspensions, metered aerosol or liquid sprays, drops, ampoules, autoinjector devices or suppositories; for administration by oral, intranasal, sublingual, intraocular, transdermal, parenteral, rectal, vaginal, inhalation or insufflation means. Alternatively, the composition may be presented in a form suitable for once-weekly or once-monthly administration; for example, an insoluble salt of the active compound, such as the decanoate salt, may be adapted to provide a depot preparation for intramuscular injection.

For preparing solid pharmaceutical compositions such as tablets, the principal active ingredient is mixed with a pharmaceutical carrier, e.g. conventional tableting ingredients such as diluents, binders, adhesives, disintegrants, lubricants, antiadherents and glidants. Suitable diluents include, but are not limited to, starch (i.e. corn, wheat, or potato starch, which may be hydrolized), lactose (granulated, spray dried or anhydrous), sucrose, sucrose-based diluents (confectioner's sugar; sucrose plus about 7 to 10 weight percent invert sugar; sucrose plus about 3 weight percent modified dextrins; sucrose plus invert sugar, about 4 weight percent invert sugar, about 0.1 to 0.2 weight percent cornstarch and magnesium stearate), dextrose, inositol, mannitol, sorbitol, microcrystalline cellulose (i.e. AVICEL™ microcrystalline cellulose available from FMC Corp.), dicalcium phosphate, calcium sulfate dihydrate, calcium lactate trihydrate and the like. Suitable binders and adhesives include, but are not limited to accacia gum, guar gum, tragacanth gum, sucrose, gelatin, glucose, starch, and cellulosics (i.e. methylcellulose, sodium carboxymethycellulose, ethylcellulose, hydroxypropylmethylcellulose, hydroxypropylcellulose, and the like), water soluble or dispersible binders (i.e. alginic acid and salts thereof, magnesium aluminum silicate, hydroxyethylcellulose (i.e. TYLOSE™ available from Hoechst Celanese), polyethylene glycol, polysaccharide acids, bentonites, polyvinylpyrrolidone, polymethacrylates and pregelatinized starch) and the like. Suitable disintegrants include, but are not limited to, starches (corn, potato, etc.), sodium starch glycolates, pregelatinized starches, clays (magnesium aluminum silicate), celluloses (such as crosslinked sodium carboxymethylcellulose and microcrystalline cellulose), alginates, pregelatinized starches (i.e. corn starch, etc.), gums (i.e. agar, guar, locust bean, karaya, pectin, and tragacanth gum), cross-linked polyvinylpyrrolidone and the like. Suitable lubricants and antiadherents include, but are not limited to, stearates (magnesium, calcium and sodium), stearic acid, talc waxes, stearowet, boric acid, sodium chloride, DL-leucine, carbowax 4000, carbowax 6000, sodium oleate, sodium benzoate, sodium acetate, sodium lauryl sulfate, magnesium lauryl sulfate and the like. Suitable gildants include, but are not limited to, talc, cornstarch, silica (i.e. CAB-O-SIL™ silica available from Cabot, SYLOID™ silica available from W. R. Grace/Davison, and AEROSIL™ silica available from Degussa) and the like. Sweeteners and flavorants may be added to chewable solid dosage forms to improve the palatability of the oral dosage form. Additionally, colorants and coatings may be added or applied to the solid dosage form for ease of identification of the drug or for aesthetic purposes. These carriers are formulated with the pharmaceutical active to provide a accurate, appropriate dose of the pharmaceutical active with a therapeutic release profile.

Generally these carriers are mixed with the pharmaceutical active to form a solid preformulation composition containing a homogeneous mixture of the pharmaceutical active of the present invention, or a pharmaceutically acceptable salt thereof. Generally the preformulation will be formed by one of three common methods: (a) wet granulation, (b) dry granulation and (c) dry blending. When referring to these preformulation compositions as homogeneous, it is meant that the active ingredient is dispersed evenly throughout the composition so that the composition may be readily subdivided into equally effective dosage forms such as tablets, pills and capsules. This solid preformulation composition is then subdivided into unit dosage forms of the type described above containing from about 0.1 mg to about 500 mg of the active ingredient of the present invention. The tablets or pills containing the novel compositions may also be formulated in multilayer tablets or pills to provide a sustained or provide dual-release products. For example, a dual release tablet or pill can comprise an inner dosage and an outer dosage component, the latter being in the form of an envelope over the former. The two components can be separated by an enteric layer, which serves to resist disintegration in the stomach and permits the inner component to pass intact into the duodenum or to be delayed in release. A variety of materials can be used for such enteric layers or coatings, such materials including a number of polymeric materials such as shellac, cellulose acetate (i.e. cellulose acetate phthalate, cellulose acetate trimetllitate), polyvinyl acetate phthalate, hydroxypropyl methylcellulose phthalate, hydroxypropyl methylcellulose acetate succinate, methacrylate and ethylacrylate copolymers, methacrylate and methyl methacrylate copolymers and the like. Sustained release tablets may also be made by film coating or wet granulation using slightly soluble or insoluble substances in solution (which for a wet granulation acts as the binding agents) or low melting solids a molten form (which in a wet granulation may incorporate the active ingredient). These materials include natural and synthetic polymers waxes, hydrogenated oils, fatty acids and alcohols (i.e. beeswax, carnauba wax, cetyl alcohol, cetylstearyl alcohol, and the like), esters of fatty acids metallic soaps, and other acceptable materials that can be used to granulate, coat, entrap or otherwise limit the solubility of an active ingredient to achieve a prolonged or sustained release product.

The liquid forms in which the novel compositions of the present invention may be incorporated for administration orally or by injection include, but are not limited to aqueous solutions, suitably flavored syrups, aqueous or oil suspensions, and flavored emulsions with edible oils such as cottonseed oil, sesame oil, coconut oil or peanut oil, as well as elixirs and similar pharmaceutical vehicles. Suitable suspending agents for aqueous suspensions, include synthetic and natural gums such as, acacia, agar, alginate (i.e. propylene alginate, sodium alginate and the like), guar, karaya, locust bean, pectin, tragacanth, and xanthan gum, cellulosics such as sodium carboxymethylcellulose, methylcellulose, hydroxymethylcellulose, hydroxyethylcellulose, hydroxypropyl cellulose and hydroxypropyl methylcellulose, and combinations thereof, synthetic polymers such as polyvinyl pyrrolidone, carbomer (i.e. carboxypolymethylene), and polyethylene glycol; clays such as bentonite, hectorite, attapulgite or sepiolite; and other pharmaceutically acceptable suspending agents such as lecithin, gelatin or the like. Suitable surfactants include but are not limited to sodium docusate, sodium lauryl sulfate, polysorbate, octoxynol-9, nonoxynol-10, polysorbate 20, polysorbate 40, polysorbate 60, polysorbate 80, polyoxamer 188, polyoxamer 235 and combinations thereof. Suitable deflocculating or dispersing agent include pharmaceutical grade lecithins. Suitable flocculating agent include but are not limited to simple neutral electrolytes (i.e. sodium chloride, potassium, chloride, and the like), highly charged insoluble polymers and polyelectrolyte species, water soluble divalent or trivalent ions (i.e. calcium salts, alums or sulfates, citrates and phosphates (which can be used jointly in formulations as pH buffers and flocculating agents). Suitable preservatives include but are not limited to parabens (i.e. methyl, ethyl, propyl and butyl), sorbic acid, thimerosal, quaternary ammonium salts, benzyl alcohol, benzoic acid, chlorhexidine gluconate, phenylethanol and the like. There are many liquid vehicles that may be used in liquid pharmaceutical dosage forms, however, the liquid vehicle that is used in a particular dosage form must be compatible with the suspending agent(s). For example, nonpolar liquid vehicles such as fatty esters and oils liquid vehicles are best used with suspending agents such as low HLB (Hydrophile-Lipophile Balance) surfactants, stearalkonium hectorite, water insoluble resins, water insoluble film forming polymers and the like. Conversely, polar liquids such as water, alcohols, polyols and glycols are best used with suspending agents such as higher HLB surfactants, clays silicates, gums, water soluble cellulosics, water soluble polymers and the like. For parenteral administration, sterile suspensions and solutions are desired. Liquid forms useful for parenteral administration include sterile solutions, emulsions and suspensions. Isotonic preparations which generally contain suitable preservatives are employed when intravenous administration is desired.

Furthermore, compounds of the present invention can be administered in intranasal form via topical use of suitable intranasal vehicles, or via transdermal skin patches the composition of which are well known to those of ordinary skill in that art. To be administered in the form of a transdermal delivery system, the administration of a therapeutic dose will, of course, be continuous rather than intermittent throughout the dosage regimen.

Compounds of the present invention can also be administered in the form of liposome delivery systems, such as small unilamellar vesicles, large unilamellar vesicles, multilamellar vesicles and the like. Liposomes can be formed from a variety of phospholipids, such as cholesterol, stearylamine, phosphatidylcholines and the like.

Compounds of the present invention may also be delivered by the use of monoclonal antibodies as individual carriers to which the compound molecules are coupled. The compounds of the present invention may also be coupled with soluble polymers as targetable drug carriers. Such polymers can include, but are not limited to polyvinylpyrrolidone, pyran copolymer, polyhydroxypropylmethacrylamidephenol, polyhydroxy-ethylaspartamidephenol, or polyethyl eneoxidepolylysine substituted with palmitoyl residue. Furthermore, the compounds of the present invention may be coupled to a class of biodegradable polymers useful in achieving controlled release of a drug, for example, to homopolymers and copolymers (which means polymers containing two or more chemically distinguishable repeating units) of lactide (which includes lactic acid d-, I- and meso lactide), glycolide (including glycolic acid), ε-caprolactone, p-dioxanone (1,4-dioxan-2-one), trimethylene carbonate (1,3-dioxan-2-one), alkyl derivatives of trimethylene carbonate, δ-valerolactone, β-butyrolactone, γ-butyrolactone, ε-decalactone, hydroxybutyrate, hydroxyvalerate, 1,4-dioxepan-2-one (including its dimer 1,5,8,12-tetraoxacyclotetradecane-7,14-dione), 1,5-dioxepan-2-one, 6,6-dimethyl-1,4-dioxan-2-one, polyorthoesters, polyacetals, polydihydropyrans, polycyanoacrylates and cross-linked or amphipathic block copolymers of hydrogels and blends thereof.

Where the processes for the preparation of the compounds according to the invention give rise to mixtures of stereoisomers, these isomers may be separated by conventional techniques such as preparative chromatography. The compounds may be prepared in racemic form or individual enantiomers may be prepared either by enantiospecific synthesis or by resolution. The compounds may, for example, be resolved into their component enantiomers by standard techniques, such as the formation of diastereomeric pairs by salt formation. The compounds may also be resolved by formation of diastereomeric esters or amides, followed by chromatographic separation and removal of the chiral auxiliary. Alternatively, the compounds may be resolved using a chiral HPLC column.

During any of the processes for preparation of the compounds of the present invention, it may be necessary and/or desirable to protect sensitive or reactive groups on any of the molecules concerned. This may be achieved by means of conventional protecting groups, such as those described in *Protective Groups in Organic Chemistry*, ed. J. F. W. McOmie, Plenum Press, 1973; and T. W. Greene & P. G. M. Wuts, *Protective Groups in Organic Synthesis*, John Wiley & Sons, 1991. The protecting groups may be removed at a convenient subsequent stage using methods known in the art.

Compounds of this invention may be administered in any of the foregoing compositions and according to dosage regimens established in the art whenever treatment of disorders of vascular resistance is required for a subject.

The daily dose of a pharmaceutical composition of the present invention may be varied over a wide range from about 0.01 to 30,000 mg per adult human per day, however the dose will preferably be in the range of from about 0.01 to about 1,000 mg per adult human per day. For oral administration, the compositions are preferably provided in the form of tablets containing, 0.01, 0.05, 0.1, 0.5, 1.0, 2.5, 5.0, 10.0, 15.0, 25.0, 50.0, 100, 150, 200, 250 and 500 milligrams of the active ingredient for the symptomatic adjustment of the dosage to the subject to be treated. An effective amount of the drug is ordinarily supplied at a dosage level of from about 0.01 mg/kg to about 300 mg/kg of body weight per day. Preferably, the range is from about 0.03 to about 100 mg/kg of body weight per day, most preferably, from about 0.03 to about 10 mg/kg of body weight per day. The compounds may be administered on a regimen of 1 to 4 times per day.

Optimal dosages to be administered may be readily determined by those skilled in the art, and will vary with the particular compound used, the mode of administration, the strength of the preparation, and the advancement of the disease condition. In addition, factors associated with the particular subject being treated, including subject age, weight, diet and time of administration, will result in the need to adjust the dose to an appropriate therapeutic level.

Abbreviations used in the instant specification, particularly the Schemes and Examples, are as follows:
Bn or Bzl=Benzyl
Boc=t-Butoxycarbonyl
BOP-Cl=Bis(2-oxo-3-oxazolidinyl)-phosphinic chloride
CBZ=Benzyloxycarbonyl
Config=Stereochemical configuration
CP or Cpd=Compound
DCM=Dichloromethane
DIC=Diisopropylcarbodiimide
DIEA=Diisopropylethylamine
DMAP=4-Dimethylaminopyridine
DMF=N,N-Dimethylformamide
DMSO=Dimethylsulfoxide
EDC=Ethyl dimethylaminopropyl-carbodiimide
Et$_2$O=Diethyl ether
EtOAc=Ethyl acetate
EtOH=Ethanol
HBTU=2-(1H-Benzotriazole-1-yl)-1,1,3,3-tetramethyluronium hexafluorophosphate
HOBT=Hydroxybenzotriazole
HPLC=High Performance Liquid Chromatography
i-Pr=Isopropyl
LAH=Lithium aluminum hydride
Me=Methyl
MeOH=Methanol
MPK=Milligrams per kilogram
NMM=N-Methylmorpholine
NT=Not tested
Ph=Phenyl
PPT=Precipitate
RT or rt=Room temperature
Sat'd=Saturated
TEA=Triethylamine
THF=Tetrahydrofuran
TFA=Trifluoroacetic acid
Z=Benzyloxycarbonyl The method of naming compounds of the present invention follow accepted nomenclature rules. Where it is noted, the letter "R" or "S" indicates the absolute configuration (Cahn-Ingold-Prelog rules). For example, structure names are generally derived according to the following system:

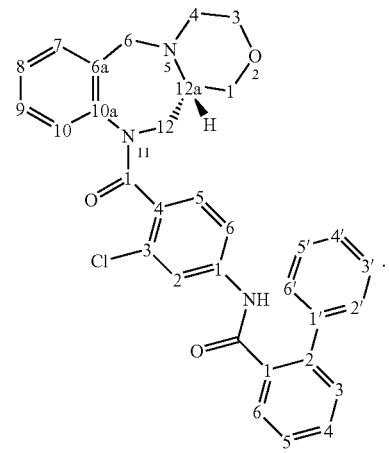

Thus, the name representing Compound 4 is: (S)-2-Phenyl-N-[3-chloro-4-(1,3,4,12a-tetrahydro-6H-[1,4]oxazino[4,3-a][1,4]-benzodiazepin-11(12H)-yl-carbonyl)phenyl]benzamide.

Particularly preferred compounds of the present invention include those compounds of formula (IVa) shown in Table I.

TABLE I

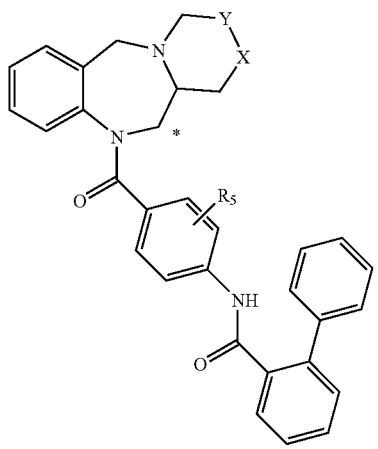

Formula (IVa)

wherein X, Y and $R_5$ are dependently selected from:

| Example # | X | Y | $R_5$ | *Config. |
|---|---|---|---|---|
| 1 | $CH_2$ | $CH_2$ | H | RS |
| 2 | CH | CH | H | RS |
| 3 | S | $CH_2$ | H | RS |
| 4 | O | $CH_2$ | 3-Cl | S |
| 48 | — | $CH_2$ | H | RS |

As in Table I, the compounds of the invention of formula (IVa), wherein X and Y are methylene may be prepared as shown in Scheme AA. Isatoic anhydride AA2 and pipecolic acid AA1 were condensed at high temperature in DMF to afford intermediate amide AA3. Amide AA3 was reduced with lithium aluminum hydride in refluxing THF, and then coupled with acid chloride AA5 to afford 4-nitrobenzamide AA6. The nitro group can be reduced to the corresponding amine AA7 with zinc, and then coupled with acid chloride AA8 to afford the final product AA9.

As shown in Tables II and III, for compounds of formula (IV), wherein X is O or S and Y is methylene, the cyclic amino acid intermediate corresponding to AA1 can be prepared as published (U. Larsson and R. Carlson, *Acta Chimica Scandinavica* 1994, 48, 517–525).

As shown in Table IV, for compounds of formula (X), wherein X is $NR_3$ and Y is methylene, the carboxylate intermediate corresponding to AD1 can be prepared as published (Bigge, C. F.; Hays, S. J.; Novak, P. M.; Drummond, J. T.; Johnson, G.; Bobovski, T. P.; *Tet. Lett.,* 1989, 30(39), 5193).

As shown in Table I, for compounds of formula (IVa), wherein X is CH and Y is CH (olefin), the cyclic amino acid intermediate corresponding to AA1 can be prepared as published (F. Rutjes, *Tetrahedron Lett.* 1997, 38, 677–680).

TABLE II

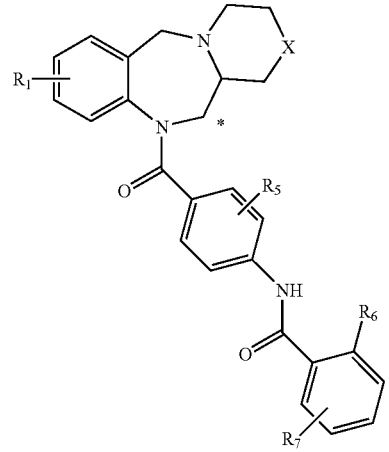

Formula (IV)

wherein X, $R_1$, $R_5$, $R_6$ and $R_7$ are dependently selected from:

| Ex # | X | $R_1$ | $R_5$ | $R_6$ | $R_7$ | *Config. |
|---|---|---|---|---|---|---|
| 5 | O | H | 3-Cl | 4'-OH—Ph | H | S |
| 6 | O | H | 3-Cl | Ph | 4-OH | S |
| 7 | O | H | 3-Cl | 3'-OH—Ph | H | S |
| 8 | O | H | 3-Cl | Ph | 5-OH | S |
| 9 | O | H | 3-Cl | 4-Me-2-thienyl | 4-F | RS |
| 10 | O | H | 3-Cl | Me | 6-Me | RS |
| 11 | O | H | 3-Cl | Me | 3-Me | RS |
| 12 | O | H | H | 4'-Me—Ph | H | RS |
| 13 | O | H | 3-Cl | Ph | H | R |
| 14 | O | H | 3-OMe | Ph | H | RS |
| 15 | O | H | 2-OMe | Ph | H | RS |
| 16 | O | H | 3-Cl | F | 3,4,5-$F_3$ | RS |
| 17 | O | H | 3-Cl | Cl | 5-$CF_3$ | RS |
| 18 | O | H | 3-Cl | F | 3-Cl | RS |
| 19 | O | H | 3-Cl | $SCHF_2$ | H | RS |
| 20 | O | H | H | Ph | H | RS |
| 21 | O | 5-oxo | 3-Cl | Ph | H | RS |
| 22 | O | H | 2-OH | Ph | H | RS |
| 23 | O | H | 3-OH | Ph | H | RS |
| 24 | O | H | 3-Cl | Me | H | RS |
| 25 | O | H | 3-Cl | 4'-Me—Ph | H | RS |
| 26 | O | H | H | Me | H | RS |
| 27 | O | H | 3-Me | Me | H | RS |
| 28 | O | H | 3-Me | 4'-Me—Ph | H | RS |
| 29 | O | H | 3-Me | Ph | H | RS |
| 30 | O | H | 3-F | 4'-Me—Ph | H | RS |
| 54 | O | H | H | 4-Me-2-thienyl | H | RS |
| 110 | O | H | 3-Cl | Me | 5-F | RS |
| 111 | O | H | 3-Cl | Ph | 5-F | RS |
| 112 | O | H | 3-Cl | 4-MeO—Ph | H | RS |
| 113 | O | H | 3-Cl | 3-MeO—Ph | H | RS |
| 114 | O | H | 3-Cl | Ph | 4-F | RS |
| 115 | O | H | 3-Cl | Ph | 4-OMe | RS |
| 116 | O | H | 3-Cl | Ph | 5-OMe | RS |

TABLE III

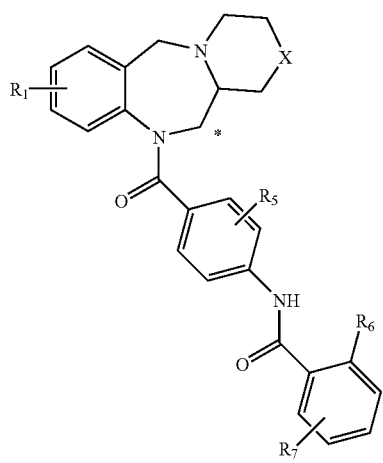

Formula (IV)

wherein X, $R_1$, $R_5$, $R_6$ and $R_7$ are dependently selected from:

| Ex # | X | $R_1$ | $R_5$ | $R_6$ | $R_7$ | *Config. |
|---|---|---|---|---|---|---|
| 3 | S | H | H | Ph | H | RS |
| 31 | S | 8-OMe | H | Ph | H | RS |
| 32 | S | 8-F | H | Ph | H | RS |
| 33 | S | 8,9-(OMe)$_2$ | H | Ph | H | RS |
| 34 | S | 9-Cl | H | Ph | H | RS |
| 35 | S | 8,9-(F)$_2$ | H | Ph | H | RS |
| 36 | S | 8-Me | H | Ph | H | RS |
| 37 | S | 8-Cl | H | Ph | H | RS |
| 38 | S | 8-F | 3-Cl | Ph | H | RS |
| 39 | S | 10-Me | H | Ph | H | RS |
| 40 | S | 10-OMe | H | Ph | H | RS |
| 41 | S | H | 3-Cl | H | 3,5-Me | RS |
| 42 | S | H | 3-Cl | I | 3-Me | RS |
| 43 | S | H | 3-Cl | H | 3,5-Cl$_2$ | RS |
| 44 | S | H | 3-Cl | Me | 3-I | RS |
| 45 | S | H | H | 2'-F-Ph | H | RS |
| 46 | S | H | 3-NMe$_2$ | Ph | H | S |
| 47 | S | H | 3-Cl | Ph | H | S |
| 49 | S | H | H | 3-Thienyl | H | RS |
| 50 | S | H | 3-Cl | 3-Thienyl | H | RS |
| 51 | S | H | 3-F | 3-Thienyl | H | RS |
| 52 | S | H | H | 2-Thienyl | H | RS |
| 53 | S | H | H | 4-Me-2-thienyl | H | RS |
| 55 | SO$_2$ | H | H | Ph | H | RS |
| 103 | S | H | 3-Cl | Me | 5-F | RS |
| 104 | S | H | 3-Cl | Ph | 5-F | RS |
| 105 | S | H | 3-Cl | Ph | 4-F | RS |
| 106 | S | H | 3-F | Ph | H | RS |
| 107 | S | H | 3-Me | Ph | H | RS |
| 108 | S | H | 3-OMe | Ph | H | RS |
| 109 | S | H | 3-OH | Ph | H | RS |

TABLE IV

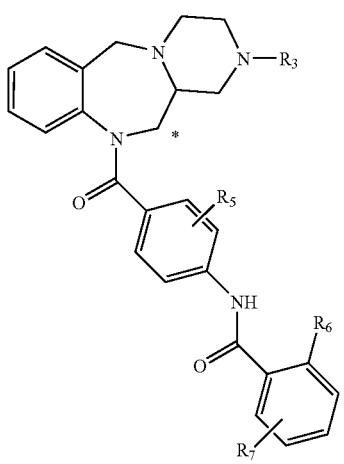

Formula (X)

wherein X, R₃, R₅, R₆ and R₇ are dependently selected from:

| Ex # | R₃ | R₅ | R₆ | R₇ | *Config. |
|---|---|---|---|---|---|
| 56 | Me | 3-Cl | Ph | H | RS |
| 57 | Bzl | H | Ph | H | RS |
| 58 | H | H | Ph | H | RS |
| 59 | Formyl | H | Ph | H | RS |
| 60 | i-Pr | 3-Cl | Ph | H | RS |
| 61 | Me | 3-Cl | Me | H | RS |
| 62 | Me | 3-Cl | Me | 3-Me | RS |
| 63 | Me | 3-Cl | Me | 6-Me | RS |
| 64 | Me | 3-Cl | F | H | RS |
| 65 | Me | 3-Cl | F | 3-Cl | RS |
| 66 | Me | 3-Cl | 4-Me—Ph | H | RS |
| 67 | Me | 3-Cl | 4-MeO—Ph | H | RS |
| 68 | Me | 3-Cl | 3-MeO—Ph | H | RS |
| 69 | Me | H | Ph | H | RS |
| 70 | Me | 3-F | Ph | H | RS |
| 71 | Me | 2-MeO | Me | H | RS |
| 72 | Me | 2-MeO | Ph | H | RS |
| 73 | Me | 2-MeO | 4-Me—Ph | H | RS |
| 74 | Me | 3-CF₃ | Me | H | RS |
| 75 | Me | 3-CF₃ | Ph | H | RS |
| 76 | Me | 3-CF₃ | 4-Me—Ph | H | RS |
| 77 | Me | 2-Me | Me | H | RS |
| 78 | Me | 2-Me | Ph | H | RS |
| 79 | Me | 2-Me | 4-Me—Ph | H | RS |
| 80 | Me | 2,6-Me | Me | H | RS |
| 81 | Me | 2,6-Me | Ph | H | RS |
| 82 | Me | 2,6-Me | 4-Me—Ph | H | RS |
| 83 | Me | 3-MeO | Me | H | RS |
| 84 | Me | 3-MeO | Ph | H | RS |
| 85 | Me | 3-MeO | 4-Me—Ph | H | RS |
| 86 | Me | H | Me | H | RS |
| 87 | Me | 3-F | Me | H | RS |
| 88 | Me | 3-Me | Me | H | RS |
| 89 | Me | 3-Me | Ph | H | RS |
| 90 | CH₂CF₃ | 3-Cl | Me | H | RS |
| 91 | CH₂CF₃ | 3-Cl | Ph | H | RS |
| 92 | Me | 3-Cl | Cl | H | RS |
| 93 | Me | 3-Cl | F | 3,4,5-F | RS |
| 94 | Me | 3-Cl | Me | 5-F | RS |
| 95 | Me | 3-Cl | Me | 3-Cl | RS |
| 96 | Me | 3-Cl | F | 5-Me | RS |
| 97 | Me | 3-Cl | Cl | 3-Cl | RS |
| 98 | Me | 3-Cl | Cl | 6-Cl | RS |
| 99 | Me | 3-Cl | F | 6-F | RS |
| 100 | Me | 3-Cl | Ph | 5-F | RS |
| 101 | Me | 3-Cl | F | 3-F | RS |
| 102 | Me | 3-Cl | Me | 3-F | RS |

The compounds of formula (II) can be prepared as with (I) using the anthranilic acid derivatives, i.e. 2-amino-3-thiophene-carboxylic acid for five-membered HET rings or 2-amino-3-pyridine-carboxylic acid for six-membered HET rings, and regioisomers thereof. The anthranilic acid derivatives can be converted to the corresponding isatoic anhydride derivatives by standard methods (condensation with carbonyldiimidazole), and then used as shown in Scheme AA.

SCHEME AA

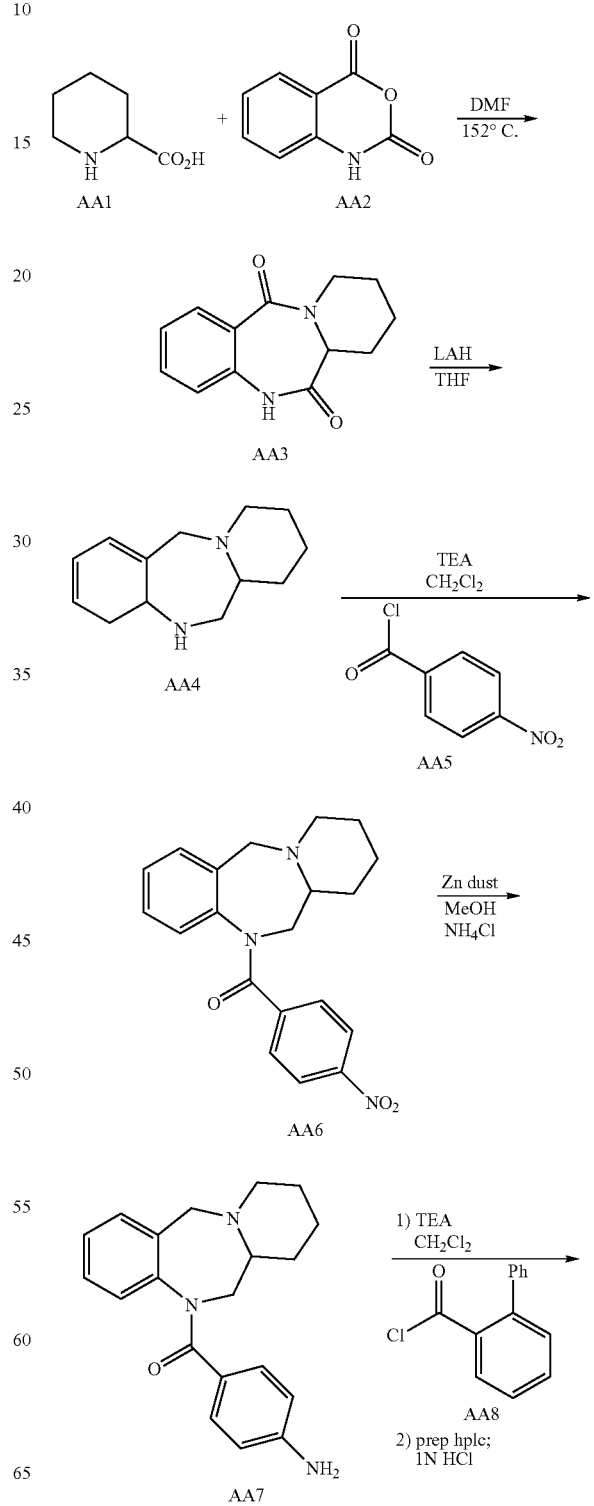

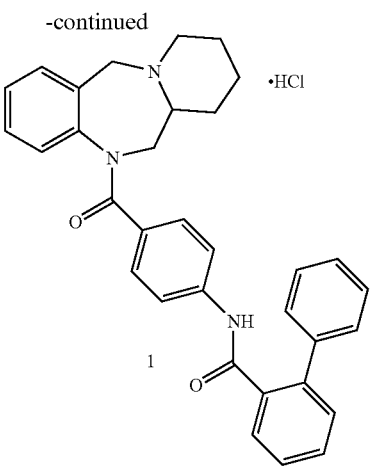

The compounds of the invention wherein X is O, Y is methylene and Q is an appropriate protecting substituent may be prepared as shown in Scheme AB. Aziridine AB1 was protected by the action of benzyl chloroformate to afford AB2, and then reacted with 2-chloroethanol to give serine derivative AB3. Compound AB3 was deprotected by hydrogenolysis and then cyclized in the presence of triethylamine to give morpholine AB5. Acylation of AB5 with 2-nitrobenzoyl chloride followed by iron-mediated reductive cyclization afforded benzodiazepinedione AB7. This bis-lactam was reduced with lithium aluminum hydride, resolved as its di-toluoyl tartrate salt, and acylated with 2-chloro-4-nitrobenzoyl chloride to produce AB9. Reduction of AB9 with zinc dust followed by acylation with 2-biphenyl carbonyl chloride afforded oxazine 4.

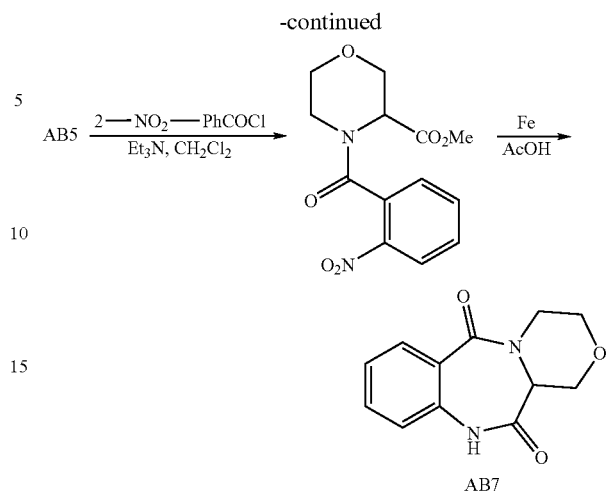

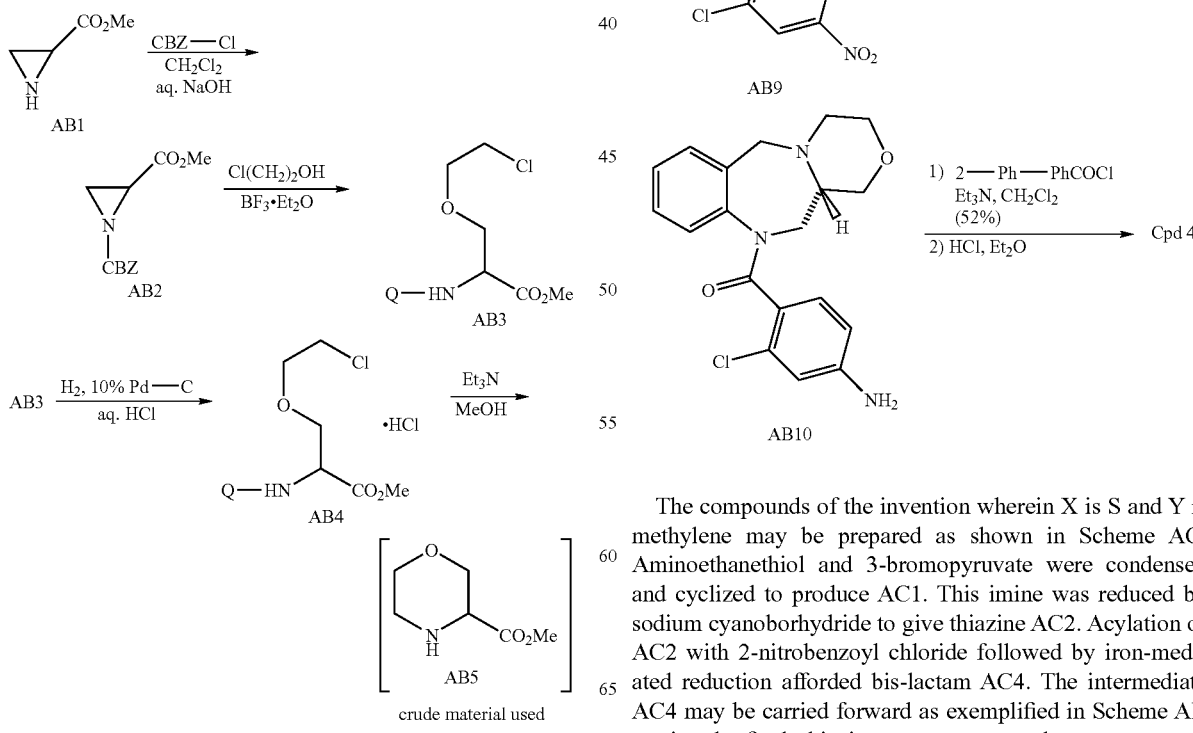

The compounds of the invention wherein X is S and Y is methylene may be prepared as shown in Scheme AC. Aminoethanethiol and 3-bromopyruvate were condensed and cyclized to produce AC1. This imine was reduced by sodium cyanoborhydride to give thiazine AC2. Acylation of AC2 with 2-nitrobenzoyl chloride followed by iron-mediated reduction afforded bis-lactam AC4. The intermediate AC4 may be carried forward as exemplified in Scheme AB to give the final, thiazine target compounds.

SCHEME AC

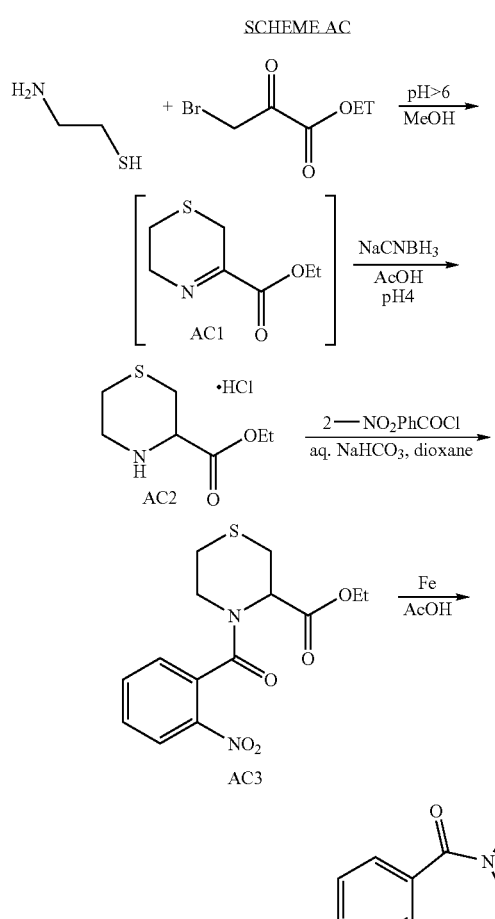

The compounds of the invention wherein X is NR$_3$, Y is methylene and Q is an appropriate protecting substituent may be prepared as shown in Scheme AD. Bis-protected piperazine AD1 was deprotected to produce AD2. Piperazine AD2 was reductively alkylated with formaldehyde to give N-methylpiperazine AD3. Deprotection using catalytic hydrogenation of AD3 provided piperazine AD4. Acylation of AD4 with 2-nitrobenzoyl chloride followed by iron-mediated reduction afforded bis-lactam AD6. The intermediate AD6 may be carried forward as exemplified in Scheme AB to give the final piperazine target compounds.

SCHEME AD

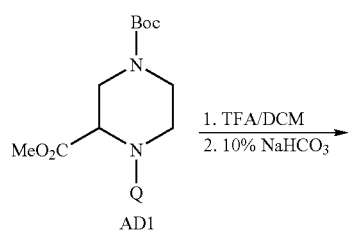

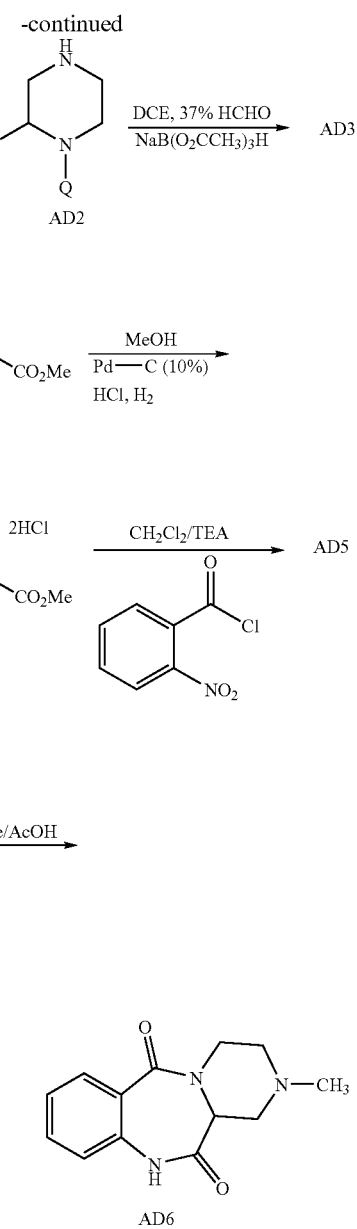

Reagents were purchased from Aldrich Chemical Company. High field $^1$H NMR spectra were recorded on a Bruker AC-360 spectrometer at 360 MHz, and coupling constants are given in Hertz. Melting points were determined on a Mel-Temp II melting point apparatus and are uncorrected. Microanalyses were performed at Robertson Microlit Laboratories, Inc., Madison, N.J. and are expressed in percentage by weight of each element per total molecular weight. In those cases where the product is obtained as a salt, the free base is obtained by methods known to those skilled in the art, e.g. by basic ion exchange purification. Nuclear magnetic resonance (NMR) spectra for hydrogen atoms were measured in the indicated solvent with tetramethylsilane (TMS) as the internal standard on a Bruker AM-360 (360 MHz) spectrometer. The values are expressed in parts per million down field from TMS. The mass spectra (MS) were determined on a Micromass/Hewlett Packard Series 1050 spectrometer (MH+), using electrospray ionization tech-

EXAMPLE 1

10-[4-[[(2-Biphenyl)carbonyl]amino]benzoyl]-10, 11-dihydro-5H-piperidino[2,1-c][1,4]benzodiazepine.HCl (1)

A mixture of isatoic anhydride (1.1 g, 0.0068 mol) and pipecolic acid (1.0 g, 0.0078 mol) in dimethylformamide (5 mL) was heated at 150° C. for 18 h, cooled to rt, and poured into ice water (10 mL). The white precipitate was filtered, washed with ice cold water, and dried in vacuo to give AA3 (1.0 g). A solution of AA3 in THF (10 mL) at rt was treated with lithium aluminum hydride (13.4 mL, 1.0 M in THF, 0.013 mol), heated at reflux for 4 h, and cooled to rt. This mixture was quenched slowly with water (5 mL) and sodium hydroxide (5 mL), and the product extracted with EtOAc (50 mL). The organic layer was washed with sat'd sodium bicarbonate (20 mL), dried (sodium sulfate), and evaporated to give AA4 as a solid (0.53 g). A solution of AA4, DCM (15 mL), and TEA (0.34 g, 0.0034 mol) at rt was treated with AA5 (0.54 g, 0.0029 mol) and stirred for 18 h. The reaction was diluted with DCM (50 mL), washed with sat'd sodium bicarbonate (15 mL), dried (sodium sulfate), and evaporated to give AA6 as a glass (0.83 g). A mixture of AA6, MeOH (29 mL), and ammonium chloride (0.75 g) was treated with zinc dust (5.2 g, 0.08 mol) and then heated at reflux for 2 h. The reaction was cooled to rt, filtered through celite, and the filtrate concentrated. The residue was treated with 10% acetic acid (1 mL), neutralized with sat'd sodium bicarbonate, and the product extracted with EtOAc (50 mL). The organic layer was washed with water (15 mL), dried (sodium sulfate), and evaporated to give AA7 as a white solid (0.59 g). A solution of AA7, DCM (9 mL), and TEA (0.24 g, 0.0024 mol) at rt was treated with AA8 (0.44 g, 0.002 mol) and stirred for 18 h. The reaction was diluted with DCM (50 mL), washed with sat'd sodium bicarbonate (20 mL), dried (sodium sulfate), and evaporated to a yellow solid. The solid was purified by reverse-phase HPLC (0.01% TFA/MeCN, C18 column) to afford a white solid. The solid was treated with HCl (1.0 N, 1.0 mL) and evaporated to afford AA9 as a tan powder: mp 191–193° C. $^1$H NMR (DMSO-$d_6$) δ 1.2 (m, 2 H), 1.6 (m, 5 H), 2.3 (t, J=4, 1 H), 2.4 (m, 1 H), 2.7 (t, J=4, 1 H), 2.9 (d, J=4, 1 H), 3.4 (d, J=6, 1 H), 3.8 (d, J=6, 1 H), 4.8 (d, J=6, 1 H), 6.4 (d, J=3, 1 H), 6.7–7.0 (m, 7 H), 7.1–7.4 (m, 8 H), 7.8 (d, J=3, 1 H); MS m/e 502.3 (MH+).

EXAMPLE 2

10-[4-[[(2-Biphenyl)carbonyl]amino]benzoyl]-10, 11-dihydro-5H-(tetrahydropyridino)[2,1-c][1,4]benzodiazepine (2)

$^1$H NMR (CDCl$_3$) δ 1.1 (m, 1 H), 2.9 (m, 1 H), 2.3 (m, 1 H), 2.7 (m, 1 H), 2.9 (m, 2 H), 3.1 (m, 1 H), 3.9 (m, 1 H), 4.7 (m, 1 H), 5.6 (br s, 2 H), 6.7 (m, 1 H), 7.1 (m, 4 H), 7.2–7.6 (m, 12 H), 10.31 (s, 1 H); MS m/e 500.3 (MH+).

EXAMPLE 3

(RS)-2-Phenyl-N-[4-(1,3,4,12a-tetrahydro-6H-[1,4] thiazino[4,3-a][1,4]-benzodiazepin-11(12H)-yl-carbonyl)phenyl]benzamide (3)

$^1$H NMR (DMSO-$d_6$) δ 2.5 (m, 5 H), 2.9 (m, 1 H), 3.2 (m, 2 H), 3.8 (d, J=6, 1 H), 4.1 (d, J=6, 1 H), 4.7 (m, 1 H), 6.7 (m, 1 H), 7.0–7.2 (m, 4 H), 7.3–7.6 (m, 11 H); MS m/e 520.5 (MH+).

EXAMPLE 4

(S)-2-Phenyl-N-[3-chloro-4-(1,3,4,12a-tetrahydro-6H-[1,4]oxazino[4,3-a][1,4]-benzodiazepin-11 (12H)-yl-carbonyl)phenyl]benzamide.HCl (4)

A solution of AB1 (49 g, 0.48 mol), DCM (1.0 L), and Et$_3$N (48.6 g, 1 eq) at 0° C. was treated with a solution of benzyl chloroformate (96 g, 1 eq) in DCM (100 mL) dropwise over 1 h. The ice bath was removed, and the mixture stirred for 20 h. The mixture was washed with water (200 mL), 20% citric acid (150 mL), and brine (100 mL). The organic layer was dried (Na$_2$SO$_4$), evaporated, and dried under high vacuum to give AB2 as an amber oil (87.4 g, 77%). A solution of AB2 (87.4 g), DCM (1.5 L), and 2-chloroethanol (225 mL, 10 eq) at rt was treated with BF$_3$.Et$_2$O (14 mL), stirred for 48 h, and diluted with water (1 L). The layers were separated, and the organic layer was dried (Na$_2$SO$_4$), evaporated, and dried under high vacuum to give AB3 as an amber oil (114 g, 99%). A mixture of AB3 (114 g, 0.36 mol), MeOH (2 L), HCl (1 N, 360 mL), and 10% Pd—C (10 g) was hydrogenated at 50 psig/rt in a Parr apparatus for 7 h. The mixture was filtered through celite and the filtrate evaporated and dried to give AB4 as white crystals (79.2 g, 99%). A mixture of AB4 (79.2 g), MeOH (8 L), and Et$_3$N (73 g, 2 eq) was heated at reflux for 7 h, cooled to rt, and evaporated to dryness. This residue was dissolved in DCM (1.2 L) and the organic layer washed with brine (2×300 mL), dried (Na$_2$SO$_4$), evaporated, and dried under high vacuum to give AB5 as a dark amber oil (29 g, 56%). A solution of AB5 (29 g, 0.20 mol), DCM (3 L), and Et$_3$N (26.3 g, 1.3 eq) at 0° C. was treated with a solution of 2-nitrobenzoyl chloride (45.4 g, 1.1 eq) in DCM (500 mL) dropwise over a 1 h period. The ice bath was removed and the mixture stirred for 18 h. This mixture was diluted with water (250 mL) and the layers separated. The organic layer was dried (Na$_2$SO$_4$), evaporated, and purified by silica gel flash chromatography (EtOAc) to give AB6 as a solid (53 g, 90%). A mixture of AB6 (50 g, 0.17 mol), AcOH (1 L), and iron (60 g, 5 eq) was heated at reflux for 20 h, cooled to rt, and filtered with AcOH wash. The filtrate was evaporated and the cooled, brown residue treated with ice-cold water (150 mL). This dark solid was filtered and dried to give AB7 as a tan solid (24.6 g, 62%). A solution of AB7 (20 g, 0.087 mol) and THF (600 mL) at 0° C. was treated with LAH (1 N in THF, Fluka, 270 mL, 3.1 eq) dropwise over a 1 h period, and the ice bath removed. The mixture was stirred for 18 h, cooled to 0° C., and treated sequentially with water (24 mL), NaOH (1 N, 36 mL), and THF (500 mL). This mixture was filtered, and the filtrate dried (Na$_2$SO$_4$), and evaporated to give an amber oil. The oil was purified by flash chromatography (1:1 hexane/EtOAc) to give the racemic tricyclic diamine product as pale yellow crystals (10.9 g, 61%). To a solution of the diamine product (6.2 g, 0.030 mol) in MeOH (40 mL) was added D-di-p-toluoyl-tartaric acid (5.8 g, 1 eq) with stirring. Once dissolution occurred, Et₂O (80 mL) was added to give a cloudy solution, and then MeOH was added dropwise until clarity was restored. The solution was capped and allowed to stand for three days to give crystals. The crystals were filtered, washed with cold Et₂O, and dried to give 3.4 g resolved salt (58%). This material was partitioned between EtOAc and NaOH (1 N), mixed thoroughly, and the layers separated. The organic layer was washed with water and brine, dried ($Na_2SO_4$), and evaporated to give AB8 as a white solid (1.52 g, 52%; no wrong enantiomer detected using Pirkle shift reagent NMR). A solution of compound AB8 (2.0 g, 0.0099 mol), DCM (20 mL), and Et₃N (1.8 mL, 1.3 eq) at 0° C. was treated with a solution of 2-chloro-4-nitrobenzoyl chloride (2.4 g, 1.1 eq) in DCM (10 mL), warmed to rt, and stirred for 1.5 h. The reaction was diluted with DCM, washed with water, dried ($Na_2SO_4$), evaporated, and purified by silica gel flash chromatography (0.1% NH₄OH/1% MeOH/DCM) to give AB9 as a white foam (3.8 g, 99%). A solution of the foam and MeOH (100 mL) was treated with NH₄Cl (2.6 g, 5 eq) and zinc dust (22.7 g, 35 eq), heated at reflux for 2 h, and cooled to rt. The mixture was filtered through celite, and the filtrate evaporated to a solid. The solid was partitioned between EtOAc and water, and the aqueous phase extracted once with EtOAc. The combined organics were washed with brine, dried ($Na_2SO_4$), and evaporated to give AB10 as a white solid (3.6 g, 99%). A solution of 2-biphenylcarboxylic acid (2.2 g, 0.011 mol), DCM (15 mL), DMF (0.1 mL), and oxalyl chloride (1.0 mL, 1 eq) was stirred for 2.5 h, and then added to a solution of AB10 (3.6), DCM (20 mL), and Et₃N (1.8 mL). This mixture was stirred for 3 h, diluted with DCM (100 mL), and washed with 10% NaHCO₃, water, and brine. The organic layer was dried ($Na_2SO_4$), evaporated, and purified by silica gel flash chromatography (0.1% NH₄OH/ 1% MeOH/DCM) to provide a white solid (ca. 2 g). The solid was dissolved in MeOH (25 mL), treated with HCl/ Et₂O (1 N, 15 mL), and the solvents evaporated to give 4 (1.0 HCl.1.3 $H_2O$.0.25Et₂O) as a white solid (2.5 g): mp>210° C. (dec.); MS m/e 538 and 540 (MH+); $[\alpha]^D_{23}$ +215.5° (c 0.278, MeOH). Anal. calcd. for $C_{32}H_{28}ClN_3O_3$.1.0 HCl.1.3 $H_2O$.0.25Et₂O (616.46): C, 64.30; H, 5.58; N, 6.82; Cl, 11.50. Found: C, 64.40; H, 5.44; N, 6.70; Cl, 11.90.

EXAMPLE 5

(S)-2-(4-Hydroxyphenyl)-N-[3-chloro-4-(1,3,4,12a-tetrahydro-6H-[1,4]oxazino[4,3-a][1,4]-benzodiazepin-11(12H)-yl-carbonyl)phenyl]benzamide.TFA (5)

White powder: ¹H NMR (CD₃OD) δ 2.61 (s, 1 H), 3.1 (m, 1 H), 3.3 (m, 3 H), 3.8 (dt, J=6 Hz, 2 H), 4.1 (m, 2 H), 4.4 (d, J=9 Hz, 1 H), 4.9 (m, 4 H), 6.7 (d, J=4 Hz, 1 H), 6.82 (s, 2 H), 7.0–7.7 (m, 12 H); MS m/e 554 and 556 (MH+).

EXAMPLE 6

(S)-2-Phenyl-4-hydroxy-N-[3-chloro-4-(1,3,4,12a-tetrahydro-6H-[1,4]oxazino[4,3-a][1,4]-benzodiazepin-11(12H)-yl-carbonyl)phenyl]benzamide.TFA (6)

White powder: ¹H NMR (CD₃OD) δ 2.59 (s, 1 H), 3.1 (m, 1 H), 3.3 (m, 3 H), 3.8 (dt, J=6 Hz, 2 H), 4.1 (m, 2 H), 4.4 (d, J=9 Hz, 1 H), 4.9 (m, 4 H), 6.8 (m, 2 H), 7.0–7.7 (m, 13 H); MS m/e 554 and 556 (MH+).

EXAMPLE 7

(S)-2-(3-Hydroxyphenyl)-N-[3-chloro-4-(1,3,4,12a-tetrahydro-6H-[1,4]oxazino[4,3-a][1,4]-benzodiazepin-11(12H)-yl-carbonyl)phenyl]benzamide.TFA (7)

White powder: ¹H NMR (CD₃OD) δ 2.60 (s, 1 H), 3.1 (m, 1 H), 3.3 (m, 3 H), 3.8 (dt, J=6 Hz, 2 H), 4.1 (m, 2 H), 4.3 (d, J=9 Hz, 1 H), 5.0 (m, 4 H), 6.7 (d, J=4 Hz, 1 H), 6.9 (d, J=4 Hz, 1 H), 7.1–7.7 (m, 13 H); MS m/e 554 and 556 (MH+).

EXAMPLE 8

(S)-2-Phenyl-5-hydroxy-N-[3-chloro-4-(1,3,4,12a-tetrahydro-6H-[1,4]oxazino[4,3-a][1,4]-benzodiazepin-11(12H)-yl-carbonyl)phenyl]benzamide.TFA (8)

White powder: ¹H NMR (CD₃OD) δ 2.59 (s, 1 H), 3.1 (m, 1 H), 3.3 (m, 3 H), 3.8 (dt, J=6 Hz, 2 H), 4.1 (m, 2 H), 4.4 (d, J=9 Hz, 1 H), 5.0 (m, 4 H), 6.9.1 (s, 2 H), 7.0 (d, J=4 Hz, 1 H), 7.12 (s, 1 H), 7.2–7.7 (m, 11 H); MS m/e 554 and 556 (MH+).

EXAMPLE 9

(RS)-2-(4-Methyl-2-thienyl)-4-fluoro-N-[3-chloro-4-(1,3,4,12a-tetrahydro-6H-[1,4]oxazino[4,3-a][1,4]-benzodiazepin-11(12H)-yl-carbonyl)phenyl]benzamide.TFA (9)

White powder: ¹H NMR (CD₃OD) δ 2.14 (s, 3 H), 2.59 (s, 1 H), 3.1 (m, 1 H), 3.3 (m, 3 H), 3.8 (dt, J=6 Hz, 2 H), 4.1 (m, 2 H), 4.4 (d, J=9 Hz, 1 H), 4.9 (m, 3 H), 6.9 (d, J=4 Hz, 2 H), 7.0–7.7 (m, 9 H), 7.62 (s, 1 H); MS m/e 576 and 578 (MH+).

EXAMPLE 10

(RS)-2,6-Dimethyl-N-[3-chloro-4-(1,3,4,12a-tetrahydro-6H-[1,4]oxazino[4,3-a][1,4]-benzodiazepin-11(12H)-yl-carbonyl)phenyl]benzamide.TFA (10)

White powder: ¹H NMR (CD₃OD) δ 1.4 (m, 1 H), 2.30 (s, 6 H), 3.2–4.1 (m, 7 H), 4.2 (d, J=9 Hz, 2 H), 4.5 (m, 1 H), 4.9 (m, 2 H), 6.9 (d, J=4 Hz, 2 H), 7.0–7.7 (m, 7 H), 7.83 (s, 1 H); MS m/e 490 and 492 (MH+).

EXAMPLE 11

(RS)-2,3-Dimethyl-N-[3-chloro-4-(1,3,4,12a-tetrahydro-6H-[1,4]oxazino[4,3-a][1,4]-benzodiazepin-11(12H)-yl-carbonyl)phenyl]benzamide.TFA (11)

White powder: ¹H NMR (CD₃OD) δ 2.28 (s, 3 H), 2.31 (s, 3 H), 3.1 (m, 1 H), 3.3–4.1 (m, 8 H), 4.4 (d, J=9 Hz, 1 H), 5.0 (m, 2 H), 7.0–7.5 (m, 8 H), 7.5 (d, J=4 Hz, 1 H), 7.6 (d, J=4 Hz, 1 H), 7.82 (s, 1 H); MS m/e 490 and 492 (MH+).

EXAMPLE 12

(RS)-2-(4-Methyl-phenyl)-N-[4-(1,3,4,12a-tetrahydro-6H-[1,4]oxazino[4,3-a][1,4]-benzodiazepin-11(12H)-yl-carbonyl)phenyl]benzamide.TFA (12)

White powder: $^1$H NMR (CD$_3$OD) δ 2.30 (s, 3 H), 3.0 (m, 1 H), 3.5 (m, 4 H), 3.8 (m, 2 H), 4.1 (m, 2 H), 4.5 (d, J=9 Hz, 1 H), 5.1 (m, 2 H), 6.9 (d, J=4 Hz, 1 H), 7.2–7.7 (m, 16 H); MS m/e 518 (MH+).

EXAMPLE 13

(R)-2-Phenyl-N-[3-chloro-4-(1,3,4,12a-tetrahydro-6H-[1,4]oxazino[4,3-a][1,4]-benzodiazepin-11(12H)-yl-carbonyl)phenyl]benzamide.HCl (13)

White powder: MS m/e 538 and 540 (MH+).

EXAMPLE 14

(RS)-2-Phenyl-N-[3-methoxy-4-(1,3,4,12a-tetrahydro-6H-[1,4]oxazino[4,3-a][1,4]-benzodiazepin-11(12H)-yl-carbonyl)phenyl]benzamide.HCl (14)

White powder: MS m/e 534.6 (MH+).

EXAMPLE 15

(RS)-2-Phenyl-N-[2-methoxy-4-(1,3,4,12a-tetrahydro-6H-[1,4]oxazino[4,3-a][1,4]-benzodiazepin-11(12H)-yl-carbonyl)phenyl]benzamide.HCl (15)

Tan powder: MS m/e 534.6 (MH+).

EXAMPLE 16

(RS)-2,3,4,5-Tetrafluoro-N-[3-chloro-4-(1,3,4,12a-tetrahydro-6H-[1,4]oxazino[4,3-a][1,4]-benzodiazepin-11(12H)-yl-carbonyl)phenyl]benzamide.TFA (16)

Yellow powder: MS m/e 535 and 537 (MH+).

EXAMPLE 17

(RS)-2-Chloro-5-trifluoromethyl-N-[3-chloro-4-(1,3,4,12a-tetrahydro-6H-[1,4]oxazino[4,3-a][1,4]-benzodiazepin-11(12H)-yl-carbonyl)phenyl]benzamide.TFA (17)

White powder: MS m/e 565 and 567 (MH+).

EXAMPLE 18

(RS)-2-Fluoro-3-chloro-N-[3-chloro-4-(1,3,4,12a-tetrahydro-6H-[1,4]oxazino[4,3-a][1,4]-benzodiazepin-11(12H)-yl-carbonyl)phenyl]benzamide.TFA (18)

White powder: MS m/e 514 and 516 (MH+).

EXAMPLE 19

(RS)-2-(Difluoromethylthio)-N-[3-chloro-4-(1,3,4,12a-tetrahydro-6H-[1,4]oxazino[4,3-a][1,4]-benzodiazepin-11(12H)-yl-carbonyl)phenyl]benzamide.TFA (19)

White powder: MS m/e 544 and 546 (MH+).

EXAMPLE 20

(RS)-2-Phenyl-N-[4-(1,3,4,12a-tetrahydro-6H-[1,4]oxazino[4,3-a][1,4]-benzodiazepin-11(12H)-yl-carbonyl)phenyl]benzamide.TFA (20)

White powder: MS m/e 504.6 (MH+).

EXAMPLE 21

(RS)-2-Phenyl-N-[3-chloro-4-(1,3,4,12a-tetrahydro-6H-[1,4]oxazino[4,3-a][1,4]-5-oxo-benzodiazepin-11(12H)-yl-carbonyl)phenyl]benzamide.TFA (21)

White powder: MS m/e 552 and 554 (MH+).

EXAMPLE 22

(RS)-2-Phenyl-N-[2-hydroxy-4-(1,3,4,12a-tetrahydro-6H-[1,4]oxazino[4,3-a][1,4]-benzodiazepin-11(12H)-yl-carbonyl)phenyl]benzamide.HCl (22)

Tan powder: MS m/e 520.6 (MH+); mp 188–195° C. (dec.).

EXAMPLE 23

(RS)-2-Phenyl-N-[3-hydroxy-4-(1,3,4,12a-tetrahydro-6H-[1,4]oxazino[4,3-a][1,4]-benzodiazepin-11(12H)-yl-carbonyl)phenyl]benzamide.HCl (23)

Tan powder: MS m/e 520.6 (MH+); mp 185–188° C. (dec.).

EXAMPLE 24

(RS)-2-Methyl-N-[3-chloro-4-(1,3,4,12a-tetrahydro-6H-[1,4]oxazino[4,3-a][1,4]-benzodiazepin-11(12H)-yl-carbonyl)phenyl]benzamide.TFA (24)

White powder: MS m/e 476 and 478 (MH+).

EXAMPLE 25

(RS)-2-(4-Methyl-phenyl)-N-[3-chloro-4-(1,3,4,12a-tetrahydro-6H-[1,4]oxazino[4,3-a][1,4]-benzodiazepin-11(12H)-yl-carbonyl)phenyl]benzamide. TFA (25)

White flakes: MS m/e 552 and 554 (MH+).

EXAMPLE 26

(RS)-2-Methyl-N-[4-(1,3,4,12a-tetrahydro-6H-[1,4]oxazino[4,3-a][1,4]-benzodiazepin-11(12H)-yl-carbonyl)phenyl]benzamide.TFA (26)

White powder: MS m/e 442.5 (MH+).

EXAMPLE 27

(RS)-2-Methyl-N-[3-methyl-4-(1,3,4,12a-tetrahydro-6H-[1,4]oxazino[4,3-a][1,4]-benzodiazepin-11(12H)-yl-carbonyl)phenyl]benzamide.TFA (27)

White powder: MS m/e 456.5 (MH+).

EXAMPLE 28

(RS)-2-(4-Methyl-phenyl)-N-[3-methyl-4-(1,3,4,12a-tetrahydro-6H-[1,4]oxazino[4,3-a][1,4]-benzodiazepin-11(12H)-yl-carbonyl)phenyl]benzamide.TFA (28)

Cream powder: MS m/e 532.6 (MH+).

EXAMPLE 29

(RS)-2-Phenyl-N-[3-methyl-4-(1,3,4,12a-tetrahydro-6H-[1,4]oxazino[4,3-a][1,4]-benzodiazepin-11(12H)-yl-carbonyl)phenyl]benzamide.TFA (29)

White powder: MS m/e 518.6 (MH+).

EXAMPLE 30

(RS)-2-(4-Methyl-phenyl)-N-[3-fluoro-4-(1,3,4,12a-tetrahydro-6H-[1,4]oxazino[4,3-a][1,4]-benzodiazepin-11(12H)-yl-carbonyl)phenyl]benzamide.TFA (30)

Cream flakes: MS m/e 536.6 (MH+).

Synthesis of AC4

A 1 L round-bottom flask was loaded with 2-aminoethanthiol hydrochloride (5.24 g, 0.046 mol), sodium bicarbonate (9.70 g, 2.5 equiv.), 4.0 g of 3 A molecular sieves (activated in the microwave oven) and 200 ml of dry methanol. Indicator—bromocresol purple, 50 mg—was added for pH monitoring, the reaction mixture was flushed by nitrogen and maintained in the nitrogen atmosphere. Ethyl bromopyruvate (10 g, 0.051 mol) was added by syringe pump with such a rate that pH of the reaction mixture was maintained above 6 (dark olive color of the reaction mixture). The addition took about 3 h. Reaction was kept for additional 30 min and sodium cyanoborohydride (5.8 g, 2 equiv.) was added as one portion.

The reaction was acidified to pH 4 and maintained at this pH for 3 h by careful addition of 6.0 M HCl. The color of the reaction mixture was yellow, the pH was monitored with Panpeha® indicator paper. Then the excess of hydrochloric acid was added to get pH 1–2, after gas evolution was ceased the reaction mixture was filtered through Celite® and evaporated in vacuum. The residue was dissolved in 200 ml of water and extracted one time with diethyl ether, the ether solution was discarded. The aqueous solution was made basic (pH 8–9) by addition of 6 N aqueous solution of sodium hydroxide and extracted 5 times by 50 ml portion of diethyl ether. Combined organic extracts were dried over magnesium sulfate and filtered. Saturation of this solution with gaseous HCl resulted the precipitation of the amino acid ester hydrochloride which was separated by filtration. The white crystals were dried in the vacuum oven providing 7.9 g (0.037 mol) of AC2 (spectral data are in accord with lit.(U. Larsson and R. Carlson, Acta Chem. Scand. 48(1994), 517–525). In a 100 ml flask, AC2 (8.66 g, 0.041 mol) was dissolved in 50 ml of dioxane containing 5 ml of water. Sodium bicarbonate (12.0 g, 0.14 mol) was added as one portion and 6.82 g (0.036 mol) of 2-nitrobenzoyl chloride was added dropwise, the addition took approximately 45 min. The system was kept 4 h at room temperature, diluted by 200 ml of brine and extracted by ether (4 times by 50 ml). Combined organic fractions were dried over anhydrous magnesium sulfate and evaporated providing 12.0 g (0.037 mol) of viscous yellow oil (AC3) which was used without further purification. A 200 ml flask with reflux condenser was loaded with AC3 (12.0 g, 0.037 mol) and 10 g of iron filings. The reaction was refluxed for 4 h and decanted into 500 ml of cold water. After 20 min of stirring the white solid was precipitated. It was filtered, washed with large amount of cold water and dried in the vacuum oven providing AC4 as white solid (7.0 g, 0.028 mol). $^1$H NMR (DMSO-$d_6$) δ 2.65 (dd, J=14.4 and 5.8 Hz, 1H) 2.74–2.91 (m, 2H), 3.16 (dt, J=12.6 and 4.7 Hz, 1H), 3.33–3.41 (m, 1H), 4.19 (dd, J=9.9 and 5.8 Hz, 1H), 4.58 (dd, J 14.1 and 4.3 Hz, 1H), 7.11 (d, J=8.0 Hz, 1H), 7.25 (t, J=7.7 Hz, 1H), 7.54 (t, J=7.2 Hz, 1H), 7.80 (d, J=8.0 Hz, 1H); MS m/e 249 (MH$^+$).

EXAMPLE 31

(RS)-2-Phenyl-N-[4-(8-methoxy-1,3,4,12a-tetrahydro-6H-[1,4]thiazino[4,3-a][1,4]-benzodiazepin-11(12H)-yl-carbonyl)phenyl]benzamide.HCl (31)

White powder: MS m/e 550.7 (MH+).

EXAMPLE 32

(RS)-2-Phenyl-N-[4-(8-fluoro-1,3,4,12a-tetrahydro-6H-[1,4]thiazino[4,3-a][1,4]-benzodiazepin-11(12H)-yl-carbonyl)phenyl]benzamide.HCl (32)

White flakes: MS m/e 538.6 (MH+); mp 177–180° C.

EXAMPLE 33

(RS)-2-Phenyl-N-[4-(8,9-dimethoxy-1,3,4,12a-tetrahydro-6H-[1,4]thiazino[4,3-a][1,4]-benzodiazepin-11(12H)-yl-carbonyl)phenyl]benzamide.HCl (33)

White powder: MS m/e 550.7 (MH+).

EXAMPLE 34

(RS)-2-Phenyl-N-[4-(9-chloro-1,3,4,12a-tetrahydro-6H-[1,4]thiazino[4,3-a][1,4]-benzodiazepin-11(12H)-yl-carbonyl)phenyl]benzamide.HCl (34)

White flakes: MS m/e 554 and 556 (MH+).

EXAMPLE 35

(RS)-2-Phenyl-N-[4-(8,9-difluoro-1,3,4,12a-tetrahydro-6H-[1,4]thiazino[4,3-a][1,4]-benzodiazepin-11(12H)-yl-carbonyl)phenyl]benzamide.HCl (35)

White powder: MS m/e 556.6 (MH+); mp 194–199° C.

EXAMPLE 36

(RS)-2-Phenyl-N-[4-(8-methyl-1,3,4,12a-tetrahydro-6H-[1,4]thiazino[4,3-a][1,4]-benzodiazepin-11(12H)-yl-carbonyl)phenyl]benzamide.HCl (36)

White flakes: MS m/e 534.7 (MH+); mp 191–196° C.

EXAMPLE 37

(RS)-2-Phenyl-N-[4-(8-chloro-1,3,4,12a-tetrahydro-6H-[1,4]thiazino[4,3-a][1,4]-benzodiazepin-11(12H)-yl-carbonyl)phenyl]benzamide.HCl (37)

White flakes: MS m/e 554 and 556 (MH+).

EXAMPLE 38

(RS)-2-Phenyl-N-[3-chloro-4-(8-fluoro-1,3,4,12a-tetrahydro-6H-[1,4]thiazino[4,3-a][1,4]-benzodiazepin-11(12H)-yl-carbonyl)phenyl]benzamide.HCl (38)

White flakes: MS m/e 572 and 574 (MH+).

EXAMPLE 39

(RS)-2-Phenyl-N-[4-(10-methyl-1,3,4,12a-tetrahydro-6H-[1,4]thiazino[4,3-a][1,4]-benzodiazepin-11(12H)-yl-carbonyl)phenyl]benzamide.HCl (39)

White powder: MS m/e 534.7 (MH+).

EXAMPLE 40

(RS)-2-Phenyl-N-[4-(10-methoxy-1,3,4,12a-tetrahydro-6H-[1,4]thiazino[4,3-a][1,4]-benzodiazepin-11(12H)-yl-carbonyl)phenyl]benzamide.HCl (40)

White powder: MS m/e 550.7 (MH+).

EXAMPLE 41

(RS)-3,5-Dimethyl-N-[3-chloro-4-(1,3,4,12a-tetrahydro-6H-[1,4]thiazino[4,3-a][1,4]-benzodiazepin-11(12H)-yl-carbonyl)phenyl]benzamide.HCl (41)

White powder: MS m/e 506 and 508 (MH+).

EXAMPLE 42

(RS)-2-Iodo-3-methyl-N-[3-chloro-4-(1,3,4,12a-tetrahydro-6H-[1,4]thiazino[4,3-a][1,4]-benzodiazepin-11(12H)-yl-carbonyl)phenyl]benzamide.HCl (42)

Yellow powder: MS m/e 618 and 620 (MH+).

EXAMPLE 43

(RS)-3,5-Dichloro-N-[3-chloro-4-(1,3,4,12a-tetrahydro-6H-[1,4]thiazino[4,3-a][1,4]-benzodiazepin-11(12H)-yl-carbonyl)phenyl]benzamide.HCl (43)

White powder: MS m/e 547 and 549 (MH+).

EXAMPLE 44

(RS)-2-Methyl-3-iodo-N-[3-chloro-4-(1,3,4,12a-tetrahydro-6H-[1,4]thiazino[4,3-a][1,4]-benzodiazepin-11(12H)-yl-carbonyl)phenyl]benzamide.HCl (44)

Tan powder: MS m/e 618 and 620 (MH+).

EXAMPLE 45

(RS)-2-(2-Fluoro-phenyl)-N-[4-(1,3,4,12a-tetrahydro-6H-[1,4]thiazino[4,3-a][1,4]-benzodiazepin-11(12H)-yl-carbonyl)phenyl]benzamide.HCl (45)

White powder: MS m/e 538.6 (MH+).

EXAMPLE 46

(S)-2-Phenyl-N-[3-dimethylamino-4-(1,3,4,12a-tetrahydro-6H-[1,4]thiazino[4,3-a][1,4]-benzodiazepin-11 (12H)-yl-carbonyl)phenyl]benzamide.HCl (46)

White powder: MS m/e 563.7 (MH+).

EXAMPLE 47

(S)-2-Phenyl-N-[3-chloro-4-(1,3,4,12a-tetrahydro-6H-[1,4]thiazino[4,3-a][1,4]-benzodiazepin-11(12H)-yl-carbonyl)phenyl]benzamide.HCl (47)

White powder: mp 192–197° C. MS m/e 554 and 556 (MH+); $[\alpha]^D_{23}$+173.4° (c 0.154, MeOH); mp 192–197° C. Anal. calcd. for $C_{32}H_{28}ClN_3O_2S.1.0$ HCl.1.0 $H_2O$(608.58): C, 63.15; H, 5.13; N, 6.90; Cl, 11.65. Found: C, 63.29; H, 4.99; N, 6.78; Cl, 11.40.

EXAMPLE 48

10-[4-[[(2-Biphenyl)carbonyl]amino]benzoyl]-10,11-dihydro-1,2-methanopyrrolidino[2,1-c][1,4]benzodiazepine.TFA (48)

White powder: MS m/e 500.3 (MH+).

EXAMPLE 49–55, 103–116

Using the procedures exemplified in the Synthesis of AC4 for the preparation of compounds wherein X is S and in Example 4 for the preparation of compounds wherein X is O, the following compounds were prepared using the appropriate starting materials and reagents:

| EX. | Name | MS (MH+) |
|---|---|---|
| 49 | (RS)-2-(3-Thienyl)-N-[4-(1,3,4,12a-tetrahydro-6H-[1,4]thiazino[4,3-a][1,4]-benzodiazepin-11(12H)-yl-carbonyl)phenyl]benzamide | 524.9 |
| 50 | (RS)-2-(3-Thienyl)-N-[3-chloro-4-(1,3,4,12a-tetrahydro-6H-[1,4]thiazino[4,3-a][1,4]-benzodiazepin-11(12H)-yl-carbonyl)phenyl]benzamide | 560.0 |
| 51 | (RS)-2-(3-Thienyl)-N-[3-fluoro-4-(1,3,4,12a-tetrahydro-6H-[1,4]thiazino[4,3-a][1,4]-benzodiazepin-11(12H)-yl-carbonyl)phenyl]benzamide | 544.0 |
| 52 | (RS)-2-(2-Thienyl)-N-[4-(1,3,4,12a-tetrahydro-6H-[1,4]thiazino[4,3-a][1,4]-benzodiazepin-11(12H)-yl-carbonyl)phenyl]benzamide | 526.0 |
| 53 | (RS)-2-(4-Methyl-2-thienyl)-N-[4-(1,3,4,12a-tetrahydro-6H-[1,4]thiazino[4,3-a][1,4]-benzodiazepin-11(12H)-yl-carbonyl)phenyl]benzamide | 540.1 |
| 54 | (RS)-2-(4-Methyl-2-thienyl)-N-[4-(1,3,4,12a-tetrahydro-6H-[1,4]oxazino[4,3-a][1,4]-benzodiazepin-11(12H)-yl-carbonyl)phenyl]benzamide | 524.0 |
| 55 | (RS)-2-Phenyl-N-[4-(1,3,4,12a-tetrahydro-2,2-dioxo-6H-[1,4]thiazino[4,3-a][1,4]-benzodiazepin-11(12H)-yl-carbonyl)phenyl]benzamide | 553.0 |
| 103 | (RS)-2-Methyl-5-fluoro-N-[3-chloro-4-(1,3,4,12a-tetrahydro-6H-[1,4]thiazino[4,3-a][1,4]-benzodiazepin-11(12H)-yl-carbonyl)phenyl]benzamide | 510.2 |
| 104 | (RS)-2-Phenyl-5-fluoro-N-[3-chloro-4-(1,3,4,12a-tetrahydro-6H-[1,4]thiazino[4,3-a][1,4]-benzodiazepin-11(12H)-yl-carbonyl)phenyl]benzamide | 572.2 |
| 105 | (RS)-2-Phenyl-4-fluoro-N-[3-chloro-4-(1,3,4,12a-tetrahydro-6H-[1,4]thiazino[4,3-a][1,4]-benzodiazepin-11(12H)-yl-carbonyl)phenyl]benzamide | 574.4 |
| 106 | (RS)-2-Phenyl-N-[3-fluoro-4-(1,3,4,12a-tetrahydro-6H-[1,4]thiazino[4,3-a][1,4]-benzodiazepin-11(12H)-yl-carbonyl)phenyl]benzamide | 538.1 |
| 107 | (RS)-2-Phenyl-N-[3-methyl-4-(1,3,4,12a-tetrahydro-6H-[1,4]thiazino[4,3-a][1,4]-benzodiazepin-11(12H)-yl-carbonyl)phenyl]benzamide | 534.1 |
| 108 | (RS)-2-Phenyl-N-[3-methoxy-4-(1,3,4,12a-tetrahydro-6H-[1,4]thiazino[4,3-a][1,4]-benzodiazepin-11(12H)-yl-carbonyl)phenyl]benzamide | 550.0 |
| 109 | (RS)-2-Phenyl-N-[3-hydroxy-4-(1,3,4,12a-tetrahydro-6H-[1,4]thiazino[4,3-a][1,4]-benzodiazepin-11(12H)-yl-carbonyl)phenyl]benzamide | 536.2 |
| 110 | (RS)-2-Methyl-5-fluoro-N-[3-chloro-4-(1,3,4,12a-tetrahydro-6H-[1,4]oxazino[4,3-a][1,4]-benzodiazepin-11(12H)-yl-carbonyl)phenyl]benzamide | 494.2 |
| 111 | (RS)-2-Phenyl-5-fluoro-N-[3-chloro-4-(1,3,4,12a-tetrahydro-6H-[1,4]oxazino[4,3-a][1,4]-benzodiazepin-11(12H)-yl-carbonyl)phenyl]benzamide | 556.3 |
| 112 | (RS)-2-(4-Methoxy-phenyl)-N-[3-chloro-4-(1,3,4,12a-tetrahydro-6H-[1,4]oxazino[4,3-a][1,4]-benzodiazepin-11(12H)-yl-carbonyl)phenyl]benzamide | 568.0 |
| 113 | (RS)-2-(3-Methoxy-phenyl)-N-[3-chloro-4-(1,3,4,12a-tetrahydro-6H-[1,4]oxazino[4,3-a][1,4]-benzodiazepin-11(12H)-yl-carbonyl)phenyl]benzamide | 568.0 |
| 114 | (RS)-2-Phenyl-4-fluoro-N-[3-chloro-4-(1,3,4,12a-tetrahydro-6H-[1,4]oxazino[4,3-a][1,4]-benzodiazepin-11(12H)-yl-carbonyl)phenyl]benzamide | 556.1 |
| 115 | (RS)-2-Phenyl-4-methoxy-N-[3-chloro-4-(1,3,4,12a-tetrahydro-6H-[1,4]oxazino[4,3-a][1,4]-benzodiazepin-11(12H)-yl-carbonyl)phenyl]benzamide | 568.1 |
| 116 | (RS)-2-Phenyl-5-methoxy-N-[3-chloro-4-(1,3,4,12a-tetrahydro-6H-[1,4]oxazino[4,3-a][1,4]-benzodiazepin-11(12H)-yl-carbonyl)phenyl]benzamide | 568.1 |

Synthesis of AD6

A solution of AD1 (58 g, 0.153 mol) and DCM (250 mL) at 0° C. was treated with trifluoroacetic acid (250 mL). The ice bath was removed, and the mixture stirred at rt for 20 h. The solvent was evaporated in vacuo and the residue was diluted with EtOAc (500 mL) and treated with 10% sodium bicarbonate. The aqueous phase was extracted with EtOAc (2×500 mL) and the organic extracts were combined, washed with water and brine. The organic layer was dried ($Na_2SO_4$), evaporated, and dried under vacuum to give AD2 as a clear oil (30 g, 70%). A solution of AD2 (15.5 g, 0.055 mol), 1,2-dichloroethane (200 mL), and 37% formaldehyde (5 mL, 3.2 eq) at rt was treated with sodium triacetoxyborohydride (16.5 g, 1.4 eq), stirred for 20 h, diluted with DCM and quenched with 1 N sodium hydroxide. The layers were separated, and the organic layer was washed with water and dried ($Na_2SO_4$), evaporated, and dried under vacuum to give AD3 as an oil (16.1 g, 99%). A mixture of AD3 (16 g, 0.055 mol), MeOH (150 mL), HCl (1 N, 5 mL), and 10% Pd—C (1.6 g) was hydrogenated at 1 atmosphere for 20 h. The mixture was filtered through celite and the filtrate evaporated and dried under vacuum to give AD4 as a white solid (12 g, 94%). A solution of AD4 (12 g, 0.051 mol), DCM (200 mL), and triethylamine (23.5 mL, 3.3 eq) at 0° C. was treated with a solution of 2-nitrobenzoyl chloride (8.0 mL, 1.2 eq) in DCM (40 mL) dropwise. The ice bath was removed, and the mixture stirred at rt for 20 h. The mixture was diluted with DCM and washed with H$_2$O and the organic layer was dried (Na$_2$SO$_4$), evaporated, and purified by silica gel flash chromatography (50:50 hexanes:EtOAc) to give AD5 as an oil (11.9 g, 76%). A mixture of AD5 (11.9 g), AcOH (200 mL), and iron (22 g, 10 eq) was heated at reflux for 7 h, cooled to rt, and filtered with AcOH wash. The filtrate was evaporated and the cooled, brown residue was partitioned between 10% sodium bicarbonate, brine, and EtOAc. The aqueous phase was extracted with EtOAc several times and the extracts combined and dried (MgSO$_4$). The inorganics were filtered and the solvent removed in vacuo to give AD6 as a white solid (5.54 g, 58%).

EXAMPLE 56–102

Using the procedures exemplified in the Synthesis of AD6 for the preparation of compounds wherein X is NR$_3$, the following compounds were prepared using appropriate starting materials and reagents:

| EX. | Name | MS (MH$^{+1}$) |
|---|---|---|
| 56 | (RS)-2-Phenyl-N-[3-chloro-4-(1,3,4,12a-tetrahydro-2-methyl-6H-[1,4]pyrazino[4,3-a][1,4]-benzodiazepin-11(12H)-yl-carbonyl)phenyl]benzamide | 551.3 |
| 57 | (RS)-2-Phenyl-N-[4-(1,3,4,12a-tetrahydro-2-benzyl-6H-[1,4]pyrazino[4,3-a][1,4]-benzodiazepin-11(12H)-yl-carbonyl)phenyl]benzamide | 593.01 |
| 58 | (RS)-2-Phenyl-N-[4-(1,3,4,12a-tetrahydro-6H-[1,4]pyrazino[4,3-a][1,4]-benzodiazepin-11(12H)-yl-carbonyl)phenyl]benzamide | 503.2 |
| 59 | (RS)-2-Phenyl-N-[4-(1,3,4,12a-tetrahydro-2-formyl-6H-[1,4]pyrazino[4,3-a][1,4]-benzodiazepin-11(12H)-yl-carbonyl)phenyl]benzamide | 531.01 |
| 60 | (RS)-2-Phenyl-N-[3-chloro-4-(1,3,4,12a-tetrahydro-2-isopropyl-6H-[1,4]pyrazino[4,3-a][1,4]-benzodiazepin-11(12H)-yl-carbonyl)phenyl]benzamide | 579.3 |
| 61 | (RS)-2-Methyl-N-[3-chloro-4-(1,3,4,12a-tetrahydro-2-methyl-6H-[1,4]pyrazino[4,3-a][1,4]-benzodiazepin-11(12H)-yl-carbonyl)phenyl]benzamide | 489.2 |
| 62 | (RS)-2,3-Dimethyl-N-[3-chloro-4-(1,3,4,12a-tetrahydro-2-methyl-6H-[1,4]pyrazino[4,3-a][1,4]-benzodiazepin-11(12H)-yl-carbonyl)phenyl]benzamide | 503.3 |
| 63 | (RS)-2,6-Dimethyl-N-[3-chloro-4-(1,3,4,12a-tetrahydro-2-methyl-6H-[1,4]pyrazino[4,3-a][1,4]-benzodiazepin-11(12H)-yl-carbonyl)phenyl]benzamide | 503.3 |
| 64 | (RS)-2-Fluoro-N-[3-chloro-4-(1,3,4,12a-tetrahydro-2-methyl-6H-[1,4]pyrazino[4,3-a][1,4]-benzodiazepin-11(12H)-yl-carbonyl)phenyl]benzamide | 493.2 |
| 65 | (RS)-2-Fluoro-3-chloro-N-[3-chloro-4-(1,3,4,12a-tetrahydro-2-methyl-6H-[1,4]pyrazino[4,3-a][1,4]-benzodiazepin-11(12H)-yl-carbonyl)phenyl]benzamide | 527.2 |
| 66 | (RS)-2-(4-Methyl-phenyl)-N-[3-chloro-4-(1,3,4,12a-tetrahydro-2-methyl-6H-[1,4]pyrazino[4,3-a][1,4]-benzodiazepin-11(12H)-yl-carbonyl)phenyl]benzamide | 565.3 |
| 67 | (RS)-2-(4-Methoxy-phenyl)-N-[3-chloro-4-(1,3,4,12a-tetrahydro-2-methyl-6H-[1,4]pyrazino[4,3-a][1,4]-benzodiazepin-11(12H)-yl-carbonyl)phenyl]benzamide | 581.3 |
| 68 | (RS)-2-(3-Methoxy-phenyl)-N-[3-chloro-4-(1,3,4,12a-tetrahydro-2-methyl-6H-[1,4]pyrazino[4,3-a][1,4]-benzodiazepin-11(12H)-yl-carbonyl)phenyl]benzamide | 581.3 |
| 69 | (RS)-2-Phenyl-N-[4-(1,3,4,12a-tetrahydro-2-methyl-6H-[1,4]pyrazino[4,3-a][1,4]-benzodiazepin-11(12H)-yl-carbonyl)phenyl]benzamide | 517.3 |
| 70 | (RS)-2-Phenyl-N-[3-fluoro-4-(1,3,4,12a-tetrahydro-2-methyl-6H-[1,4]pyrazino[4,3-a][1,4]-benzodiazepin-11(12H)-yl-carbonyl)phenyl]benzamide | 535.3 |
| 71 | (RS)-2-Methyl-N-[2-methoxy-4-(1,3,4,12a-tetrahydro-2-methyl-6H-[1,4]pyrazino[4,3-a][1,4]-benzodiazepin-11(12H)-yl-carbonyl)phenyl]benzamide | 485.3 |
| 72 | (RS)-2-Phenyl-N-[2-methoxy-4-(1,3,4,12a-tetrahydro-2-methyl-6H-[1,4]pyrazino[4,3-a][1,4]-benzodiazepin-11(12H)-yl-carbonyl)phenyl]benzamide | 547.2 |
| 73 | (RS)-2-(4-Methyl-phenyl)-N-[2-methoxy-4-(1,3,4,12a-tetrahydro-2-methyl-6H-[1,4]pyrazino[4,3-a][1,4]-benzodiazepin-11(12H)-yl-carbonyl)phenyl]benzamide | 561.3 |
| 74 | (RS)-2-Methyl-N-[3-trifluoromethyl-4-(1,3,4,12a-tetrahydro-2-methyl-6H-[1,4]pyrazino[4,3-a][1,4]-benzodiazepin-11(12H)-yl-carbonyl)phenyl]benzamide | 523.2 |

-continued

| EX. | Name | MS (MH$^{+1}$) |
|---|---|---|
| 75 | (RS)-2-Phenyl-N-[3-trifluoromethyl-4-(1,3,4,12a-tetrahydro-2-methyl-6H-[1,4]pyrazino[4,3-a][1,4]-benzodiazepin-11(12H)-yl-carbonyl)phenyl]benzamide | 585.3 |
| 76 | (RS)-2-(4-Methyl-phenyl)-N-[3-trifluoromethyl-4-(1,3,4,12a-tetrahydro-2-methyl-6H-[1,4]pyrazino[4,3-a][1,4]-benzodiazepin-11(12H)-yl-carbonyl)phenyl]benzamide | 599.3 |
| 77 | (RS)-2-Methyl-N-[2-methyl-4-(1,3,4,12a-tetrahydro-2-methyl-6H-[1,4]pyrazino[4,3-a][1,4]-benzodiazepin-11(12H)-yl-carbonyl)phenyl]benzamide | 469.2 |
| 78 | (RS)-2-Phenyl-N-[2-methyl-4-(1,3,4,12a-tetrahydro-2-methyl-6H-[1,4]pyrazino[4,3-a][1,4]-benzodiazepin-11(12H)-yl-carbonyl)phenyl]benzamide | 531.3 |
| 79 | (RS)-2-(4-Methyl-phenyl)-N-[2-methyl-4-(1,3,4,12a-tetrahydro-2-methyl-6H-[1,4]pyrazino[4,3-a][1,4]-benzodiazepin-11(12H)-yl-carbonyl)phenyl]benzamide | 545.3 |
| 80 | (RS)-2-Methyl-N-[2,6-dimethyl-4-(1,3,4,12a-tetrahydro-2-methyl-6H-[1,4]pyrazino[4,3-a][1,4]-benzodiazepin-11(12H)-yl-carbonyl)phenyl]benzamide | 483.4 |
| 81 | (RS)-2-Phenyl-N-[2,6-dimethyl-4-(1,3,4,12a-tetrahydro-2-methyl-6H-[1,4]pyrazino[4,3-a][1,4]-benzodiazepin-11(12H)-yl-carbonyl)phenyl]benzamide | 545.3 |
| 82 | (RS)-2-(4-Methyl-phenyl)-N-[2,6-dimethyl-4-(1,3,4,12a-tetrahydro-2-methyl-6H-[1,4]pyrazino[4,3-a][1,4]-benzodiazepin-11(12H)-yl-carbonyl)phenyl]benzamide | 559.4 |
| 83 | (RS)-2-Methyl-N-[3-methoxy-4-(1,3,4,12a-tetrahydro-2-methyl-6H-[1,4]pyrazino[4,3-a][1,4]-benzodiazepin-11(12H)-yl-carbonyl)phenyl]benzamide | 485.3 |
| 84 | (RS)-2-Phenyl-N-[3-methoxy-4-(1,3,4,12a-tetrahydro-2-methyl-6H-[1,4]pyrazino[4,3-a][1,4]-benzodiazepin-11(12H)-yl-carbonyl)phenyl]benzamide | 547.3 |
| 85 | (RS)-2-(4-Methyl-phenyl)-N-[3-methoxy-4-(1,3,4,12a-tetrahydro-2-methyl-6H-[1,4]pyrazino[4,3-a][1,4]-benzodiazepin-11(12H)-yl-carbonyl)phenyl]benzamide | 561.3 |
| 86 | (RS)-2-Methyl-N-[4-(1,3,4,12a-tetrahydro-2-methyl-6H-[1,4]pyrazino[4,3-a][1,4]-benzodiazepin-11(12H)-yl-carbonyl)phenyl]benzamide | 455.3 |
| 87 | (RS)-2-Methyl-N-[3-fluoro-4-(1,3,4,12a-tetrahydro-2-methyl-6H-[1,4]pyrazino[4,3-a][1,4]-benzodiazepin-11(12H)-yl-carbonyl)phenyl]benzamide | 473.3 |
| 88 | (RS)-2-Methyl-N-[3-methyl-4-(1,3,4,12a-tetrahydro-2-methyl-6H-[1,4]pyrazino[4,3-a][1,4]-benzodiazepin-11(12H)-yl-carbonyl)phenyl]benzamide | 469.2 |
| 89 | (RS)-2-Phenyl-N-[3-methyl-4-(1,3,4,12a-tetrahydro-2-methyl-6H-[1,4]pyrazino[4,3-a][1,4]-benzodiazepin-11(12H)-yl-carbonyl)phenyl]benzamide | 531.3 |
| 90 | (RS)-2-Methyl-N-[3-chloro-4-(1,3,4,12a-tetrahydro-2-(2,2,2-trifluoroethyl)-6H-[1,4]pyrazino[4,3-a][1,4]-benzodiazepin-11(12H)-yl-carbonyl)phenyl]benzamide | 557.3 |
| 91 | (RS)-2-Phenyl-N-[3-chloro-4-(1,3,4,12a-tetrahydro-2-(2,2,2-trifluoroethyl)-6H-[1,4]pyrazino[4,3-a][1,4]-benzodiazepin-11(12H)-yl-carbonyl)phenyl]benzamide | 619.2 |
| 92 | (RS)-2-Chloro-N-[3-chloro-4-(1,3,4,12a-tetrahydro-2-methyl-6H-[1,4]pyrazino[4,3-a][1,4]-benzodiazepin-11(12H)-yl-carbonyl)phenyl]benzamide | 509.1 |
| 93 | (RS)-2,3,4,5-Tetrafluoro-N-[3-chloro-4-(1,3,4,12a-tetrahydro-2-methyl-6H-[1,4]pyrazino[4,3-a][1,4]-benzodiazepin-11(12H)-yl-carbonyl)phenyl]benzamide | 547.2 |
| 94 | (RS)-2-Methyl-5-fluoro-N-[3-chloro-4-(1,3,4,12a-tetrahydro-2-methyl-6H-[1,4]pyrazino[4,3-a][1,4]-benzodiazepin-11(12H)-yl-carbonyl)phenyl]benzamide | 507.2 |
| 95 | (RS)-2-Methyl-3-chloro-N-[3-chloro-4-(1,3,4,12a-tetrahydro-2-methyl-6H-[1,4]pyrazino[4,3-a][1,4]-benzodiazepin-11(12H)-yl-carbonyl)phenyl]benzamide | 523.2 |
| 96 | (RS)-2-Fluoro-5-methyl-N-[3-chloro-4-(1,3,4,12a-tetrahydro-2-methyl-6H-[1,4]pyrazino[4,3-a][1,4]-benzodiazepin-11(12H)-yl-carbonyl)phenyl]benzamide | 507.2 |
| 97 | (RS)-2,3-Dichloro-N-[3-chloro-4-(1,3,4,12a-tetrahydro-2-methyl-6H-[1,4]pyrazino[4,3-a][1,4]-benzodiazepin-11(12H)-yl-carbonyl)phenyl]benzamide | 545.2 |
| 98 | (RS)-2,6-Dichloro-N-[3-chloro-4-(1,3,4,12a-tetrahydro-2-methyl-6H-[1,4]pyrazino[4,3-a][1,4]-benzodiazepin-11(12H)-yl-carbonyl)phenyl]benzamide | 543.2 |
| 99 | (RS)-2,6-Difluoro-N-[3-chloro-4-(1,3,4,12a-tetrahydro-2-methyl-6H-[1,4]pyrazino[4,3-a][1,4]-benzodiazepin-11(12H)-yl-carbonyl)phenyl]benzamide | 511.2 |

-continued

| EX. | Name | MS (MH$^{+1}$) |
|---|---|---|
| 100 | (RS)-2-Phenyl-5-fluoro-N-[3-chloro-4-(1,3,4,12a-tetrahydro-2-methyl-6H-[1,4]pyrazino[4,3-a][1,4]-benzodiazepin-11(12H)-yl-carbonyl)phenyl]benzamide | 569.3 |
| 101 | (RS)-2,3-Difluoro-N-[3-chloro-4-(1,3,4,12a-tetrahydro-2-methyl-6H-[1,4]pyrazinol[4,3-a][1,4]-benzodiazepin-11(12H)-yl-carbonyl)phenyl]benzamide | 511.11 |
| 102 | (RS)-2-Methyl-3-fluoro-N-[3-chloro-4-(1,3,4,12a-tetrahydro-2-methyl-6H-[1,4]pyrazino[4,3-a][1,4]-benzodiazepin-11(12H)-yl-carbonyl)phenyl]benzamide | 507.09 |

EXAMPLE 117

As a specific embodiment of an oral composition, 100 mg of the compound 9 of Example 1 is formulated with sufficient finely divided lactose to provide a total amount of 580 to 590 mg to fill a size 0 hard gel capsule.

EXAMPLE 118

In Vitro Recombinant Vasopressin Receptor Binding Assay.

Compounds were assessed for their ability to displace $^3$H-arginine vasopressin from the human V-1 or V-2 receptor in HEK-293 cells. Assay buffer is 50 mM Tris-Cl, 5 mM MgCl$_2$, 0.1% BSA (pH 7.5) containing 5 ug/ml of aprotinin, leupeptin, pepstatin, 50 ug/ml bacitracin, and 1 mM Pefabloc. $^3$H-vasopressin is $^3$H-arginine-8-vasopressin (68.5 Ci/mmol, final concentration in assay is 0.65–0.75 nM). Into wells of 96-well round bottom polypropylene plates were added buffer, test compound, membrane (containing cloned human V-1 or V-2 receptor), and $^3$H-vasopressin. The reaction plates were allowed to sit at room temperature for one hour. The samples were filtered through Unifilter GF/C plates (presoaked in 0.3 polyethyleneimine). The plates were washed 5 times with cold physiological saline containing 0.05% Tween 20. After drying, the bottom of the filter plates were sealed and 0.025 ml of Microscint-20 was added to each filter. The top of the plate was sealed, and the plate was counted. Non-specific binding was determined by the addition of 1.25 uM arginine-8-vasopressin in those wells.

EXAMPLE 119

Reversal of Vasopressin-Induced Hypertension in Rats.

The anti-hypertensive activity of compounds was screened in an anesthetized model of vasopressin-induced hypertension. Male Long Evans, normotensive rats of between 350 and 450 g in body weight were anesthetized with pentobarbital (35 mg/kg, ip) and maintained throughout the procedure with an ip infusion of 10 mg/kg/hr. Arginine vasopressin was infused at 30 ng/kg/min, iv, to induce a stable hypertensive state (ca. 50 mmHg increase in mean arterial blood pressure). Compounds of interest were administered in an ascending dose fashion and the maximum decrease in mean arterial blood pressure was recorded. An ED$_{50}$ was determined from the linear portion of the dose-response relationship for each animal.

This model was modified slightly to assess the bioavailability of compounds of interest. Rather than dosing the animals iv in an ascending dose fashion, a single dose per animal was administered directly into the duodenum. The anti-hypertensive effects were then monitored for 60 minutes and the maximum percent reversal was calculated.

TABLE V

In Vitro Results

| Cmpd | V2 Bdg IC$_{50}$ (nM) | V1 Bdg (% inh, 0.1 uM) | V2 cAMP IC$_{50}$ (uM) |
|---|---|---|---|
| 1 | 9 | 31% | 0.21 |
| 2 | 14 | 29% | 0.46 |
| 3 | 10 | 42% | 0.71 |
| 4 | 2 | (0.082 uM) | 0.011 |
| 5 | 9 | 29% | NT |
| 6 | 3 | 49% | NT |
| 7 | 11 | 1% | NT |
| 8 | 27 | 32% | NT |
| 9 | 11 | 18% | NT |
| 10 | 9 | 15% | NT |
| 11 | 8 | 11% | NT |
| 12 | 6 | (0.030 uM) | NT |
| 13 | 32 | (2.8 uM) | NT |
| 14 | 9 | 36% | NT |
| 15 | 13 | 69% | NT |
| 16 | 25 | 20% | NT |
| 17 | (63%/0.1 uM) | 13% | NT |
| 18 | 18 | 15% | NT |
| 19 | 27 | 24% | NT |
| 20 | 8 | 69% | NT |
| 21 | (59%/0.1 uM) | 2% | NT |
| 22 | 6 | 67% | NT |
| 23 | 10 | 33% | NT |
| 24 | 16 | 34% | NT |
| 25 | 12 | 60% | NT |
| 26 | (65%/0.1 uM) | 58% | NT |
| 27 | 13 | 7% | NT |
| 28 | 10 | 14% | NT |
| 29 | 6 | 3% | NT |
| 30 | 14 | 74% | NT |
| 31 | 43 | 27%/10 uM | NT |
| 32 | 20 | 44%/10 uM | NT |
| 33 | (19%/0.1 uM) | 6%/10 uM | NT |
| 34 | (41%/0.1 uM) | 1%/10 uM | NT |
| 35 | 38 | 15%/10 uM | NT |
| 36 | 18 | 76% | NT |
| 37 | 22 | 75% | NT |
| 38 | 18 | 9% | NT |
| 39 | (37%/0.1 uM) | (0.77 uM) | NT |
| 40 | (12%/0.1 uM) | (4.3 uM) | NT |
| 41 | (38%/0.1 uM) | 5% | NT |
| 42 | (62%/0.1 uM) | 0% | NT |
| 43 | (47%/0.1 uM) | 11% | NT |
| 44 | (43%/0.1 uM) | 2% | NT |
| 45 | (69%/0.1 uM) | 15% | NT |
| 46 | 47 | 8% | NT |
| 47 | 11 | (0.85 uM) | NT |
| 49 | (59%/0.1 uM) | NT | NT |
| 50 | 40 | NT | NT |
| 51 | (62%/0.1 uM) | NT | NT |
| 52 | (36%/0.1 uM) | NT | NT |
| 53 | 15 | NT | NT |
| 54 | (57%/0.1 uM) | (0.065 uM) | NT |
| 55 | 140 | NT | NT |
| 56 | 35/54/(71%/0.1 uM) | IA | NT |
| 57 | (25%/0.1 uM) | IA | NT |

TABLE V-continued

In Vitro Results

| Cmpd | V2 Bdg IC$_{50}$ (nM) | V1 Bdg (% inh, 0.1 uM) | V2 cAMP IC$_{50}$ (uM) |
|---|---|---|---|
| 58 | (33%/0.1 uM) | IA | NT |
| 59 | (29%/0.1 uM) | (17%/10 uM) | NT |
| 60 | (25%/0.1 uM) | IA | NT |
| 61 | (28%/0.1 uM) | (21%/1 uM) | NT |
| 62 | (28%/48%/0.1 uM) | (11%/33%/1 uM) | NT |
| 63 | (9%/0.1 uM) | (0%/26%/1 uM) | NT |
| 64 | (0%/5%/0.1 uM) | (1%/12%/1 uM) | NT |
| 65 | (17%/0.1 uM) | IA | NT |
| 66 | (82%/0.1 uM) | IA | NT |
| 67 | (36%/0.1 uM) | (14%/1 uM) | NT |
| 68 | (37%/0.1 uM) | (7%/1 uM) | NT |
| 69 | (38%/0.1 uM) | (22%/1 uM) | NT |
| 70 | (44%/0.1 uM) | (9%/1 uM) | NT |
| 71 | IA | (12%/1 uM) | NT |
| 72 | (48%/0.1 uM) | (6%/1 uM) | NT |
| 73 | 43/(73%/0.1 uM) | IA | NT |
| 74 | (4%/0.1 uM) | IA | NT |
| 75 | (2%/0.1 uM) | IA | NT |
| 76 | (50%/0.1 uM) | (18%/1 uM) | NT |
| 77 | IA | IA | NT |
| 78 | (5%/0.1 uM) | (2%/1 uM) | NT |
| 79 | (33%/0.1 uM) | IA | NT |
| 80 | (6%/0.1 uM) | (19%/1 uM) | NT |
| 81 | IA | IA | NT |
| 82 | IA | IA | NT |
| 83 | (10%/0.1 uM) | (44%/1 uM) | NT |
| 84 | (36%/0.1 uM) | (10%/1 uM) | NT |
| 85 | (54%/0.1 uM) | (19%/1 uM) | NT |
| 86 | (1%/0.1 uM) | (33%/1 uM) | NT |
| 87 | IA | IA | NT |
| 88 | IA | IA | NT |
| 89 | (56%/0.1 uM) | (51%/1 uM) | NT |
| 90 | IA | IA | NT |
| 91 | (31%/0.1 uM) | (2%/1 uM) | NT |
| 92 | IA | IA | NT |
| 93 | (24%/0.1 uM) | (49%/1 uM) | NT |
| 94 | (39%/0.1 uM) | IA | NT |
| 95 | (38%/0.1 uM) | (10%/1 uM) | NT |
| 96 | (3%/0.1 uM) | (9%/1 uM) | NT |
| 97 | (9%/0.1 uM) | (21%/1 uM) | NT |
| 98 | (12%/0.1 uM) | (26%/1 uM) | NT |
| 99 | (10%/0.1 uM) | (12%/1 uM) | NT |
| 100 | 37/(72%/0.1 uM) | (6%/1 uM) | NT |
| 101 | IA | (6%/1 uM) | NT |
| 102 | (20%/0.1 uM) | (12%/1 uM) | NT |
| 103 | IA | IA | NT |
| 104 | 79 | IA | NT |
| 105 | 8 | (1.4 uM) | NT |
| 106 | 22 | IA | NT |
| 107 | 21 | IA | NT |
| 108 | 32 | IA | NT |
| 109 | 7 | (0.38 uM) | NT |
| 110 | 6 | ~1000 | NT |
| 111 | 23 | ~1000 | NT |
| 112 | 6 | IA | NT |
| 113 | 8 | IA | NT |
| 114 | 4 | IA | NT |
| 115 | 9 | IA | NT |
| 116 | 37 | IA | NT |

IA = Inactive;
NT = not tested.

TABLE VI

In Vivo Blood Pressure Reduction Results

| Cmpd # | I.D. Dose (mg/kg) | BP Reduction (%) |
|---|---|---|
| 1 | 10 | 67% |
| 3 | 10 | 100% |
| 4 | 10 | 100% |

While the foregoing specification teaches the principles of the present invention, with examples provided for the purpose of illustration, it will be understood that the practice of the invention encompasses all of the usual variations, adaptations and/or modifications as come within the scope of the following claims and their equivalents.

What is claimed is:
1. A solid oral dosage form comprising
   (a) a compound of the formula (I) or (II):

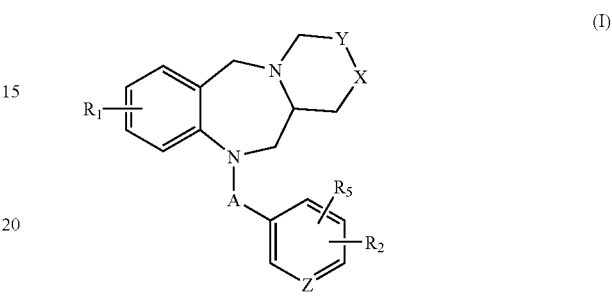

(I)

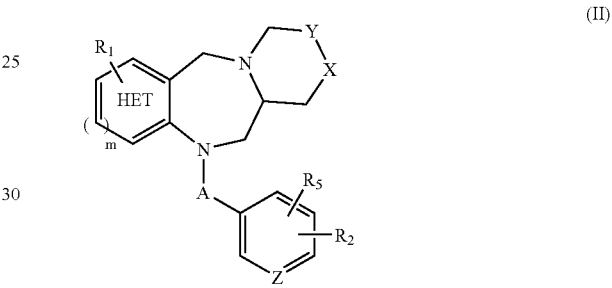

(II)

wherein m is an integer from 0 to 1;

with the proviso that if m is 0 or 1, then

"HET" in the compound of formula (II) is a stable five- or six-membered monocyclic aromatic ring system composed of carbon atoms and one heteroatom, wherein the heteroatom is selected from the group consisting of N, O and S which may occupy any position in the ring whereby the resulting ring system is stable;

A is selected from the group consisting of —C(O)—, SO$_2$ and CH$_2$;

Y is selected from the group consisting of CH$_2$ and CH as part of an olefin;

X is selected from the group consisting of CH$_2$, CH as part of an olefin, NR$_3$, S and O;

with the proviso that if Y is CH as part of an olefin, then X is CH as part of an olefin;

Z is selected from the group consisting of N and CH;

R$_1$ is one to two substituents independently selected from the group consisting of hydrogen, alkyl, alkoxy, halogen, aminoalkyl and nitro;

Ar is selected from naphthyl, wherein naphthyl is optionally substituted with from one to four substituents independently selected from C$_1$–C$_8$ alkyl, C$_1$–C$_8$ alkoxy, fluorinated C$_1$–C$_8$ alkyl, fluorinated C$_1$–C$_8$ alkoxy, halogen, cyano, hydroxy, amino, nitro, C$_1$–C$_4$ alkylamino and C$_1$–C$_4$ dialkylamino (wherein the alkyl groups on the amino may be the same or different); or phenyl, wherein phenyl is optionally substituted with from one to four substituents independently selected from C$_1$–C$_8$ alkyl, C$_1$–C$_8$ alkoxy, fluorinated C$_1$–C$_8$ alkyl, fluorinated C$_1$–C$_8$ alkoxy, C$_1$–C$_1$–C$_8$ aralkyl (wherein optionally the alkyl or aryl portions are independently substituted and the alkyl portion may be substituted with at least one fluorine and/or the aryl portion may be independently substituted with from one to two substituents selected from halogen, $C_1$–$C_4$ alkyl, $C_1$–$C_6$ alkylthio and hydroxyl), $C_1$–$C_8$ aralkoxy (wherein optionally the alkoxy or aryl portions are independently substituted and the alkoxy portion may be substituted with at least one fluorine and/or the aryl portion may be independently substituted with from one to two substituents selected from halogen, $C_1$–$C_4$ alkyl, $C_1$–$C_6$ alkylthio and hydroxyl), halogen, cyano, hydroxy, amino, nitro, $C_1$–$C_8$ alkylamino, $C_1$–$C_4$ dialkylamino (wherein the alkyl groups on the amino may be the same or different), $(halo)_{1-3}(C_1$–$C_8)$alkylthio, $C_1$–$C_8$ alkylsulfonyl, $C_1$–$C_8$ alkylthio, $C_1$–$C_8$ alkylsulfinyl, heteroaryl (optionally substituted with one to two substituents independently selected from $C_1$–$C_8$ alkyl) and phenyl (optionally substituted with from one to two substituents independently selected from $C_1$–$C_4$ alkyl, $C_1$–$C_4$ alkoxy, fluorinated $C_1$–$C_4$ alkyl, fluorinated $C_1$–$C_4$ alkoxy, halogen, cyano, hydroxy, amino, nitro, $C_1$–$C_4$ alkylamino, $C_1$–$C_4$ dialkylamino (wherein the alkyl groups on the amino may be the same or different), $C_1$–$C_4$ alkylsulfonyl, $C_1$–$C_4$ alkylthio, and $C_1$–$C_4$ alkylsulfinyl);

$R_2$ is selected from the group consisting of $NR_4COAr$, $NR_4CO$-heteroaryl, $NR_4Ar$, CH=CH—Ar, CF=CH—Ar, CH=CF—Ar, CCl=CH—Ar, CH=CCl—Ar, CH=CH-heteroaryl, CF=CH-heteroaryl, CH=CF-heteroaryl, —CCl=CH-heteroaryl, CH=CCl-heteroaryl, $OCH_2$—Ar, $OCH_2$-heteroaryl, $SCH_2$—Ar and $NR_4CH_2Ar$;

$R_3$ is selected from the group consisting of hydrogen, acyl, alkyl, alkoxycarbonyl, alkylsulfonyl and arylsulfonyl;

$R_4$ is selected from the group consisting of hydrogen and $C_1$–$C_4$ alkyl;

$R_5$ is selected from the group consisting of hydrogen, $C_1$–$C_4$ alkyl, $C_1$–$C_4$ alkoxy, chlorine, fluorine, hydroxy, dialkylamino (wherein the alkyl groups on the amino may be the same or different), trifluoromethyl and trifluoromethoxy;

and pharmaceutically acceptable salts thereof; and (b) pharmaceutically acceptable carriers.

2. The solid oral dosage form of claim 1 wherein "HET" of formula II is selected from the group consisting of thiophene, furan, pyrrole and pyridine;

A is —C(O)—;

Ar is naphthyl, wherein naphthyl is optionally substituted with from one to four substituents independently selected from trifluoromethyl, trifluoromethoxy, —NH—$C_1$–$C_4$ alkyl and —N—$(C_1$–$C_4$ alkyl$)_2$ (wherein the alkyl groups on the amino may be the same or different);

$R_2$ is $NR_4COAr$;

$R_4$ is selected from the group consisting of hydrogen and methyl.

3. The solid oral dosage form of claim 1 wherein $R_4$ is hydrogen.

4. The solid oral dosage form of claim 1 wherein the compound is of formula (III):

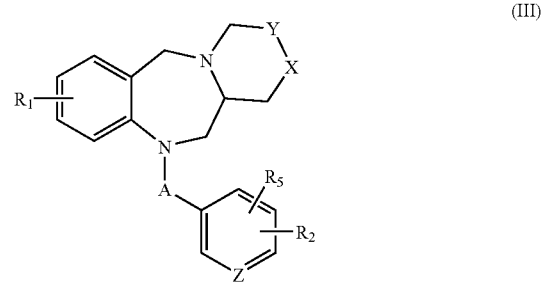

(III)

wherein

Y is selected from the group consisting of $CH_2$ and CH as part of an olefin;

X is selected from the group consisting of $CH_2$, CH as part of an olefin, $NR_3$, S and O;

with the proviso that if Y is CH as part of an olefin, then X is CH as part of an olefin;

$R_1$ is one to two substituents independently selected from the group consisting of hydrogen, $C_1$–$C_4$ alkyl, $C_1$–$C_4$ alkoxy, halogen, amino $C_1$–$C_4$ alkyl, and nitro;

$R_2$ is NHCOAr;

$R_3$ is selected from the group consisting of hydrogen, acyl, $C_1$–$C_4$ alkyl, $C_1$–$C_4$ alkylsulfonyl and arylsulfonyl;

$R_5$ is selected from the group consisting of hydrogen, $C_1$–$C_4$ alkyl, $C_1$–$C_4$ alkoxy, chlorine, fluorine, hydroxy, dialkylamino (wherein the alkyl groups on the amino may be the same or different), trifluoromethyl and trifluoromethoxy;

and (b) a pharmaceutically acceptable carrier.

5. The solid oral dosage form of claim 4 wherein Y is selected from the group consisting of $CH_2$ and CH as part of an olefin;

X is selected from the group consisting of $CH_2$, CH as part of an olefin, O and S;

with the proviso that if Y is CH as part of an olefin, then X is CH as part of an olefin;

A is —C(O)—;

Z is CH;

Ar is phenyl, wherein phenyl is optionally substituted with from one to four substituents independently selected from $C_1$–$C_8$ alkyl, $C_1$–$C_8$ alkoxy, fluorinated $C_1$–$C_8$ alkyl, fluorinated $C_1$–$C_8$ alkoxy, $C_1$–$C_8$ aralkyl (wherein optionally the alkyl or aryl portions are independently substituted and the alkyl portion may be substituted with at least one fluorine and/or the aryl portion may be independently substituted with from one to two substituents selected from halogen, $C_1$–$C_4$ alkyl, $C_1$–$C_6$ alkylthio and hydroxyl), $C_1$–$C_8$ aralkoxy (wherein optionally the alkoxy or aryl portions are independently substituted and the alkoxy portion may be substituted with at least one fluorine and/or the aryl portion may be independently substituted with from one to two substituents selected from halogen, $C_1$–$C_4$ alkyl, $C_1$–$C_6$ alkylthio and hydroxyl), halogen, cyano, hydroxy, amino, nitro, $C_1$–$C_8$ alkylamino, $C_1$–$C_4$ dialkylamino (wherein the alkyl groups on the amino may be the same or different), $(halo)_{1-3}(C_1$–$C_8)$alkylthio, $C_1$–$C_8$ alkylsulfonyl, $C_1$–$C_8$ alkylthio, $C_1$–$C_8$ alkylsulfinyl, heteroaryl (optionally substituted with one to two substituents independently selected from $C_1-C_8$ alkyl) and phenyl (optionally substituted with from one to two substituents independently selected from $C_1-C_4$ alkyl, $C_1-C_4$ alkoxy, fluorinated $C_1-C_4$ alkyl, fluorinated $C_1-C_4$ alkoxy, halogen, cyano, hydroxy, amino, nitro, $C_1-C_4$ alkylamino, $C_1-C_4$ dialkylamino (wherein the alkyl groups on the amino may be the same or different), $C_1-C_4$ alkylsulfonyl, $C_1-C_4$ alkylthio, and $C_1-C_4$ alkylsulfinyl);

and (b) a pharmaceutically acceptable carrier.

6. A solid oral dosage form comprising (a) a compound of the formula (IV):

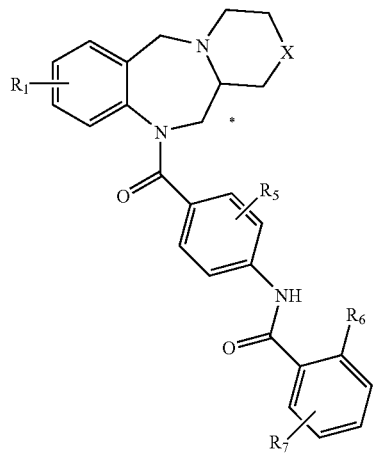

X is selected from the group consisting of $CH_2$, S and O;

$R_1$ is one to two substituents independently selected from the group consisting of hydrogen, $C_1-C_4$ alkyl, $C_1-C_4$ alkoxy, halogen, amino $C_1-C_4$ alkyl and nitro;

$R_5$ is selected from the group consisting of hydrogen, $C_1-C_4$ alkyl, $C_1-C_4$ alkoxy, chlorine, fluorine, hydroxy, dialkylamino (wherein the alkyl groups on the amino may be the same or different), trifluoromethyl and trifluoromethoxy;

$R_6$ is selected from the group consisting of hydrogen, $C_1-C_4$ alkyl, $C_1-C_4$ alkoxy, phenyl (wherein the phenyl is optionally substituted with from one to two substituents independently selected from $C_1-C_4$ alkyl, $C_1-C_4$ alkoxy, fluorinated $C_1-C_4$ alkyl, fluorinated $C_1-C_4$ alkoxy, halogen, cyano, hydroxy, amino, nitro, $C_1-C_4$ alkylamino, $C_1-C_4$ dialkylamino (wherein the alkyl groups on the amino may be the same or different), $C_1-C_4$ alkylsulfonyl, $C_1-C_4$ alkylthio, and $C_1-C_4$ alkylsulfinyl); aralkyl (wherein the alkyl or aryl portions are optionally independently substituted and the alkyl portion may be substituted with at least one fluorine and/or the aryl portion may be independently substituted with from one to two substituents selected from halogen, $C_1-C_4$ alkyl, $C_1-C_6$ alkylthio and hydroxyl), aralkoxy (wherein the alkoxy or aryl portions are optionally independently substituted and the alkoxy portion may be substituted with at least one fluorine and/or the aryl portion may be independently substituted with from one to two substituents selected from halogen, $C_1-C_4$ alkyl, $C_1-C_6$ alkylthio and hydroxyl), heteroaryl (optionally substituted with one to two substituents independently selected from $C_1-C_4$ alkyl and halogen), heteroaryl($C_1-C_8$)alkyl (wherein the heteroaryl portion is optionally substituted with one to two substituents selected from $C_1-C_8$ alkyl), (halo)$_{1-3}$($C_1-C_4$)alkylthio and halogen; and $R_7$ is independently selected from the group consisting of hydrogen, fluorine, chlorine, iodine, hydroxyl, $C_1-C_6$ alkyl, $C_1-C_6$ alkoxy, fluorinated $C_1-C_6$ alkyl and combinations thereof, wherein $R_7$ represent one to four independently selected groups; and (b) pharmaceutically acceptable carrier.

7. The solid oral dosage form of claim 6 wherein the carrier is selected from the group consisting of diluents, granulating agents, lubricants, binders, glidants, and disintegrating agents.

8. A solid oral dosage form comprising (a) a compound of formula (IVa):

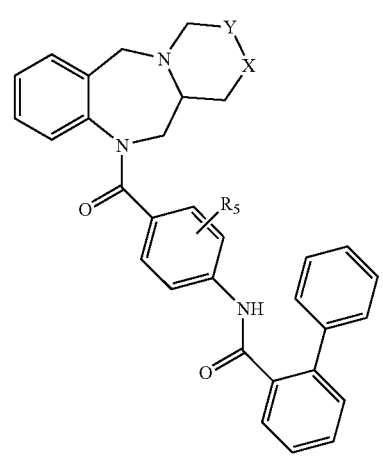

Formula (IVa)

wherein

Y is selected from the group consisting of $CH_2$ and CH as part of an olefin;

X is selected from the group consisting of $CH_2$, CH as part of an olefin, S and O;

with the proviso that if Y is CH as part of an olefin, then X is CH as part of an olefin;

$R_5$ is one to two substituents independently selected from the group consisting of hydrogen, $C_1-C_4$ alkyl, $C_1-C_4$ alkoxy, chlorine, fluorine, hydroxy, dialkylamino (wherein the alkyl groups may be the same or different), trifluoromethyl and trifluoromethoxy; and (b) pharmaceutically acceptable carrier.

9. The solid oral dosage form of claim 8 wherein the carrier is selected from the group consisting of diluents, granulating agents, lubricants, binders, glidants, and disintegrating agents.

10. A solid oral dosage form comprising (a) a compound of formula (I):

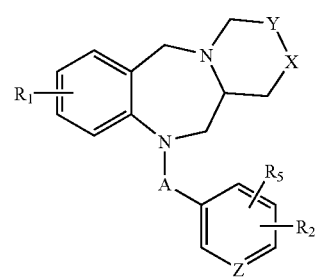

(I)

wherein
A is selected from the group consisting of —C(O)—, SO$_2$ and CH$_2$;
Y is selected from the group consisting of CH$_2$ and CH as part of an olefin;
X is selected from the group consisting of CH$_2$, CH as part of an olefin, NR$_3$, S, O and SO$_2$;
with the proviso that if Y is CH as part of an olefin, then X is CH as part of an olefin;
Z is selected from the group consisting of N and CH;
R$_1$ is one to two substituents independently selected from the group consisting of hydrogen, alkyl, alkoxy, halogen, aminoalkyl, and nitro;
R$_2$ is selected from the group consisting of NR$_4$COAr, NR$_4$CO-heteroaryl, NR$_4$Ar, CH=CH—Ar, CF=CH—Ar, CH=CF—Ar, CCl=CH—Ar, CH=CCl—Ar, CH=CH-heteroaryl, CF=CH-heteroaryl, CH=CF-heteroaryl, —CCl=CH-heteroaryl, CH=CCl-heteroaryl, OCH$_2$—Ar, OCH$_2$-heteroaryl, SCH$_2$—Ar and NR$_4$CH$_2$Ar;
R$_3$ is selected from the group consisting of hydrogen, acyl, alkyl, aralkyl, alkoxycarbonyl, alkylsulfonyl, fluorinated alkyl and arylsulfonyl;
Ar is selected from the group consisting of naphthyl, wherein naphthyl is optionally substituted with from one to four substituents independently selected from the group consisting of C$_1$–C$_8$ alkyl, C$_1$–C$_8$ alkoxy, fluorinated C$_1$–C$_8$ alkyl, fluorinated C$_1$–C$_8$ alkoxy, halogen, cyano, hydroxy, amino, nitro, C$_1$–C$_4$ alkylamino and C$_1$–C$_4$ dialkylamino (wherein the alkyl groups on the amino may be the same or different); and phenyl, wherein phenyl is optionally substituted with from one to four substituents independently selected from C$_1$–C$_8$ alkyl, C$_1$–C$_8$ alkoxy, fluorinated C$_1$–C$_8$ alkyl, fluorinated C$_1$–C$_8$ alkoxy, C$_1$–C$_8$ aralkyl (wherein the alkyl portion is optionally substituted with at least one fluorine and the aryl portion is optionally substituted with from one to two substituents selected from the group consisting of halogen, C$_1$–C$_4$ alkyl, C$_1$–C$_6$ alkylthio and hydroxy), C$_1$–C$_8$ aralkoxy (wherein the alkoxy portion is optionally substituted with at least one fluorine and the aryl portion is optionally substituted with from one to two substituents selected from the group consisting of halogen, C$_1$–C$_4$ alkyl, C$_1$–C$_6$ alkylthio and hydroxy), halogen, cyano, hydroxy, amino, nitro, C$_1$–C$_8$ alkylamino, C$_1$–C$_4$ dialkylamino (wherein the alkyl groups on the amino may be the same or different), C$_1$–C$_8$ alkylsulfonyl, C$_1$–C$_8$ alkylthio, (halo)$_{1-3}$(C$_1$–C$_8$)alkylthio, C$_1$–C$_8$ alkylsulfinyl, heteroaryl (optionally substituted with one to two substituents independently selected from the group consisting of C$_1$–C$_8$ alkyl and halogen), heteroaryl(C$_1$–C$_8$)alkyl (wherein the heteroaryl portion is optionally substituted with one to two substituents independently selected from C$_1$–C$_8$ alkyl) and phenyl (optionally substituted with from one to two substituents independently selected from the group consisting of C$_1$–C$_4$ alkyl, C$_1$–C$_4$ alkoxy, fluorinated C$_1$–C$_4$ alkyl, fluorinated C$_1$–C$_4$ alkoxy, halogen, cyano, hydroxy, amino, nitro, C$_1$–C$_4$ alkylamino, C$_1$–C$_4$ dialkylamino (wherein the alkyl groups on the amino may be the same or different), C$_1$–C$_4$ alkylsulfonyl, C$_1$–C$_4$ alkylthio and C$_1$–C$_4$ alkylsulfinyl);
R$_4$ is selected from the group consisting of hydrogen and C$_1$–C$_4$ alkyl;
R$_5$ is one to two substituents independently selected from the group consisting of hydrogen, C$_1$–C$_4$ alkyl, C$_1$–C$_4$ alkoxy, chlorine, fluorine, hydroxy, dialkylamino (wherein the alkyl groups on the amino may be the same or different), trifluoromethyl and trifluoromethoxy;
and (b) a pharmaceutically acceptable carrier.

11. The solid oral dosage form of claim 10 wherein the carrier is selected from the group consisting of diluents, granulating agents, lubricants binders, glidants, and disintegrating agents.

12. The solid oral dosage form of claim 10 wherein A is —C(O)—.

13. The solid oral dosage form compound of claim 10 wherein Z is CH.

14. The solid oral dosage form of claim 10 wherein R$_1$ is one to two substituents independently selected from the group consisting of hydrogen, C$_1$–C$_4$ alkyl, C$_1$–C$_4$ alkoxy, and halogen.

15. The solid oral dosage form of claim 10 wherein R$_1$ is one to two substituents independently selected from the group consisting of hydrogen, methyl, methoxy, chlorine, and fluorine.

16. The solid oral dosage form of claim 10 wherein Ar is phenyl optionally substituted with from one to four substituents independently selected from the group consisting of C$_1$–C$_8$ alkyl, C$_1$–C$_8$ alkoxy, fluorinated C$_1$–C$_8$ alkyl, fluorinated C$_1$–C$_8$ alkoxy, C$_1$–C$_8$ aralkyl (wherein the alkyl portion is optionally substituted with at least one fluorine and the aryl portion is optionally substituted with from one to two substituents independently selected from the group consisting of halogen, C$_1$–C$_4$ alkyl, C$_1$–C$_6$ alkylthio and hydroxy), C$_1$–C$_8$ aralkoxy (wherein the alkoxy portion is optionally substituted with at least one fluorine and the aryl portion is optionally substituted with from one to two substituents independently selected from the group consisting of halogen, C$_1$–C$_4$ alkyl, C$_1$–C$_6$ alkylthio and hydroxy), halogen, cyano, hydroxy, amino, nitro, C$_1$–C$_8$ alkylamino, C$_1$–C$_4$ dialkylamino (wherein the alkyl groups on the amino may be the same or different), C$_1$–C$_8$ alkylsulfonyl, C$_1$–C$_8$ alkylthio, (halo)$_{1-3}$(C$_1$–C$_8$)alkylthio, C$_1$–C$_8$ alkylsulfinyl, heteroaryl (optionally substituted with one to two substituents independently selected from the group consisting of C$_1$–C$_8$ alkyl and halogen), heteroaryl(C$_1$–C$_8$)alkyl (wherein the heteroaryl portion is optionally substituted with one to two substituents independently selected from C$_1$–C$_8$ alkyl) and phenyl (optionally substituted with from one to two substituents independently selected from the group consisting of C$_1$–C$_4$ alkyl, C$_1$–C$_4$ alkoxy, fluorinated C$_1$–C$_4$ alkyl, fluorinated C$_1$–C$_4$ alkoxy, halogen, cyano, hydroxy, amino, nitro, C$_1$–C$_4$ alkylamino, C$_1$–C$_4$ dialkylamino (wherein the alkyl groups on the amino may be the same or different), C$_1$–C$_4$ alkylsulfonyl, C$_1$–C$_4$ alkylthio and C$_1$–C$_4$ alkylsulfinyl).

17. The solid oral dosage form of claim 10 wherein Ar is phenyl optionally substituted with from one to four substituents independently selected from the group consisting of C$_1$–C$_8$ alkyl, C$_1$–C$_8$ alkoxy, fluorinated C$_1$–C$_8$ alkyl, halogen, hydroxy, (halo)$_{1-3}$(C$_1$–C$_8$)alkylthio, heteroaryl (optionally substituted with one to two substituents independently selected from the group consisting of C$_1$–C$_8$ alkyl and halogen) and phenyl (optionally substituted with from one to two substituents independently selected from the group consisting of C$_1$–C$_4$ alkyl, C$_1$–C$_4$ alkoxy, halogen and hydroxy).

18. The solid oral dosage form of claim 10 wherein Ar is phenyl optionally substituted with from one to four substituents independently selected from the group consisting of C$_1$–C$_4$ alkyl, C$_1$–C$_4$ alkoxy, fluorinated C$_1$–C$_4$ alkyl, halogen, hydroxy, (halo)$_{1-3}$(C$_1$–C$_4$)alkylthio, heteroaryl (optionally substituted with one to two substituents independently selected from the group consisting of C$_1$–C$_4$ alkyl and halogen) and phenyl (optionally substituted with from one to two substituents independently selected from the group consisting of C$_1$–C$_4$ alkyl, C$_1$–C$_4$ alkoxy, halogen and hydroxy).

19. The solid oral dosage from of claim 10 wherein Ar is phenyl optionally substituted with from one to four substituents independently selected from the group consisting of C$_1$–C$_4$ alkyl, C$_1$–C$_4$ alkoxy, fluorinated C$_1$–C$_4$ alkyl, halogen, hydroxy and (halo)$_{1-3}$(C$_1$–C$_4$)alkylthio, heteroaryl (optionally substituted with one to two substituents independently selected from the group consisting of C$_1$–C$_4$ alkyl and halogen) and phenyl (optionally substituted with from one to two substituents independently selected from the group consisting of C$_1$–C$_4$ alkyl, C$_1$–C$_4$ alkoxy, halogen and hydroxy).

20. The solid oral dosage form of claim 10 wherein R$_2$ is selected from the group consisting of NR$_4$COAr, NR$_4$CO-heteroaryl, NR$_4$Ar, CH=CH—Ar, CF=CH—Ar, CH=CF—Ar, CCl=CH—Ar, CH=CCl—Ar, CH=CH-heteroaryl, CF=CH-heteroaryl, CH=CF-heteroaryl, —CCl=CH-heteroaryl, CH=CCl-heteroaryl and NR$_4$CH$_2$Ar.

21. The solid oral dosage form of claim 10 wherein R$_2$ is selected from NR$_4$COAr.

22. The solid oral dosage form of claim 10 wherein R$_2$ is selected from NHCOAr.

23. The solid oral dosage of claim 10 wherein R$_3$ is selected from the group consisting of hydrogen, acyl, C$_1$–C$_8$ alkyl, ar(C$_1$–C$_8$)alkyl, C$_1$–C$_8$ alkoxycarbonyl, C$_1$–C$_8$ alkylsulfonyl, fluorinated(C$_1$–C$_8$) alkyl and arylsulfonyl.

24. The solid oral dosage of claim 10 wherein R$_3$ is selected from the group consisting of hydrogen, acyl, C$_1$–C$_4$ alkyl, ar(C$_1$–C$_4$)alkyl and trifluoro(C$_1$–C$_4$)alkyl.

25. The solid oral dosage form of claim 10 wherein R$_3$ is selected from the group consisting of hydrogen, formyl, methyl, isopropyl, benzyl and trifluoroethyl.

26. The solid oral dosage form of claim 10 wherein R$_5$ is one to two substituents independently selected from the group consisting of hydrogen, methyl, methoxy, chlorine, fluorine, hydroxy, dimethylamino and trifluoromethyl.

27. The solid oral dosage form of claim 6 wherein R$_6$ is selected from the group consisting of hydrogen, C$_1$–C$_4$ alkyl, C$_1$–C$_4$ alkoxy, phenyl (wherein the phenyl is optionally substituted with from one to two substituents independently selected from the group consisting of C$_1$–C$_4$ alkyl, C$_1$–C$_4$ alkoxy, fluorinated C$_1$–C$_4$ alkyl, fluorinated C$_1$–C$_4$ alkoxy, halogen, cyano, hydroxy, amino, nitro, C$_1$–C$_4$ alkylamino, C$_1$–C$_4$ dialkylamino (wherein the alkyl groups on the amino may be the same or different), C$_1$–C$_4$ alkylsulfonyl, C$_1$–C$_4$ alkylthio and C$_1$–C$_4$ alkylsulfinyl); heteroaryl (optionally substituted with one to two substituents independently selected from the group consisting of C$_1$–C$_4$ alkyl and halogen), heteroaryl(C$_1$–C$_8$)alkyl (wherein the heteroaryl portion is optionally substituted with one to two substituents independently selected from C$_1$–C$_8$ alkyl), (halo)$_{1-3}$(C$_1$–C$_4$)alkylthio and halogen.

28. The solid oral dosage form of claim 6 wherein R$_6$ is selected from the group consisting of hydrogen, C$_1$–C$_4$ alkyl, phenyl (optionally substituted with from one to two substituents independently selected from the group consisting of C$_1$–C$_4$ alkyl, C$_1$–C$_4$ alkoxy, halogen and hydroxy), heteroaryl (optionally substituted with one to two substituents independently selected from C$_1$–C$_4$ alkyl), (halo)$_{1-3}$(C$_1$–C$_4$)alkylthio and halogen.

29. The solid oral dosage form of claim 6 wherein R$_6$ is selected from the group consisting of hydrogen, methyl, phenyl (optionally substituted with from one to two substituents independently selected from the group consisting of methyl, methoxy, fluorine and hydroxy), thienyl (optionally substituted with methyl), difluoromethylthio, fluorine, chlorine and iodine.

30. The solid oral dosage of claim 6 wherein R$_7$ is one to three substituents independently selected from the group consisting of hydrogen, fluorine, chlorine, iodine, hydroxy, C$_1$–C$_6$ alkyl, C$_1$–C$_6$ alkoxy and fluorinated C$_1$–C$_6$ alkyl.

31. The solid oral dosage form of claim 6 wherein R$_7$ is one to three substituents independently selected from the group consisting of hydrogen, fluorine, chlorine, iodine, hydroxy, C$_1$–C$_4$ alkyl, C$_1$–C$_4$ alkoxy and fluorinated C$_1$–C$_4$ alkyl.

32. The solid oral dosage form of claim 6 wherein R$_7$ is one to three substituents independently selected from the group consisting of hydrogen, fluorine, chlorine, iodine, hydroxy, C$_1$–C$_2$ alkyl, C$_1$–C$_2$ alkoxy and fluorinated C$_1$–C$_2$ alkyl.

33. The solid oral dosage form of claim 6 wherein R$_7$ is one to three substituents independently selected from the group consisting of hydrogen, fluorine, chlorine, iodine, hydroxy, methyl, methoxy and trifluoromethyl.

34. The solid oral dosage form of claim 1 selected from the group consisting of
- 10-[4-[[(2-Biphenyl)carbonyl]amino]benzoyl]-10,11-dihydro-5H-piperidino[2,1-c][1,4]benzodiazepine;
- 10-[4-[[(2-Biphenyl)carbonyl]amino]benzoyl]-10,11-dihydro-5H-(tetrahydropyridino)[2,1-c][1,4]benzodiazepine;
- (RS)-2-Phenyl-N-[4-(1,3,4,12a-tetrahydro-6H-[1,4]thiazino[4,3-a][1,4]-benzodiazepin-11(12H)-yl-carbonyl)phenyl]benzamide;
- (S)-2-Phenyl-N-[3-chloro-4-(1,3,4,12a-tetrahydro-6H-[1,4]oxazino[4,3-a][1,4]-benzodiazepin-11(12H)-yl-carbonyl)phenyl]benzamide;
- (S)-2-(4-Hydroxyphenyl)-N-[3-chloro-4-(1,3,4,12a-tetrahydro-6H-[1,4]oxazino[4,3-a][1,4]-benzodiazepin-11(12H)-yl-carbonyl)phenyl]benzamide;
- (S)-2-Phenyl-4-hydroxy-N-[3-chloro-4-(1,3,4,12a-tetrahydro-6H-[1,4]oxazino[4,3-a][1,4]-benzodiazepin-11(12H)-yl-carbonyl)phenyl]benzamide;
- (S)-2-(3-Hydroxyphenyl)-N-[3-chloro-4-(1,3,4,12a-tetrahydro-6H-[1,4]oxazino[4,3-a][1,4]-benzodiazepin-11(12H)-yl-carbonyl)phenyl]benzamide;
- (S)-2-Phenyl-5-hydroxy-N-[3-chloro-4-(1,3,4,12a-tetrahydro-6H-[1,4]oxazino[4,3-a][1,4]-benzodiazepin-11(12H)-yl-carbonyl)phenyl]benzamide;
- (RS)-2-(4-Methyl-2-thienyl)-4-fluoro-N-[3-chloro-4-(1,3,4,12a-tetrahydro-6H-[1,4]oxazino[4,3-a][1,4]-benzodiazepin-11(12H)-yl-carbonyl)phenyl]benzamide;
- (RS)-2,6-Dimethyl-N-[3-chloro-4-(1,3,4,12a-tetrahydro-6H-[1,4]oxazino[4,3-a][1,4]-benzodiazepin-11(12H)-yl-carbonyl)phenyl]benzamide;
- (RS)-2,3-Dimethyl-N-[3-chloro-4-(1,3,4,12a-tetrahydro-6H-[1,4]oxazino[4,3-a][1,4]-benzodiazepin-11(12H)-yl-carbonyl)phenyl]benzamide;
- (RS)-2-(4-Methyl-phenyl)-N-[4-(1,3,4,12a-tetrahydro-6H-[1,4]oxazino[4,3-a][1,4]-benzodiazepin-11(12H)-yl-carbonyl)phenyl]benzamide;
- (R)-2-Phenyl-N-[3-chloro-4-(1,3,4,12a-tetrahydro-6H-[1,4]oxazino[4,3-a][1,4]-benzodiazepin-11(12H)-yl-carbonyl)phenyl]benzamide;

(RS)-2-Phenyl-N-[3-methoxy-4-(1,3,4,12a-tetrahydro-6H-[1,4]oxazino[4,3-a][1,4]-benzodiazepin-11(12H)-yl-carbonyl)phenyl]benzamide;

(RS)-2-Phenyl-N-[2-methoxy-4-(1,3,4,12a-tetrahydro-6H-[1,4]oxazino[4,3-a][1,4]thiazino[4,3-a][1,4]-benzodiazepin-11(12H)-yl-carbonyl)phenyl]benzamide;

(RS)-2,3,4,5-Tetrafluoro-N-[3-chloro-4-(1,3,4,12a-tetrahydro-6H-[1,4]oxazino[4,3-a][1,4]-benzodiazepin-11(12H)-yl-carbonyl)phenyl]benzamide;

(RS)-2-Chloro-5-trifluoromethyl-N-[3-chloro-4-(1,3,4,12a-tetrahydro-6H-[1,4]oxazino[4,3-a][1,4]-benzodiazepin-11(12H)-yl-carbonyl)phenyl]benzamide;

(RS)-2-Fluoro-3-chloro-N-[3-chloro-4-(1,3,4,12a-tetrahydro-6H-[1,4]oxazino[4,3-a][1,4]-benzodiazepin-11(12H)-yl-carbonyl)phenyl]benzamide;

(RS)-2-(Difluoromethylthio)-N-[3-chloro-4-(1,3,4,12a-tetrahydro-6H-[1,4]oxazino[4,3-a][1,4]-benzodiazepin-11(12H)-yl-carbonyl)phenyl]benzamide;

(RS)-2-Phenyl-N-[4-(1,3,4,12a-tetrahydro-6H-[1,4]oxazino[4,3-a][1,4]-benzodiazepin-11(12H)-yl-carbonyl)phenyl]benzamide;

(RS)-2-Phenyl-N-[2-hydroxy-4-(1,3,4,12a-tetrahydro-6H-[1,4]oxazino[4,3-a][1,4]-benzodiazepin-11(12H)-yl-carbonyl)phenyl]benzamide;

(RS)-2-Phenyl-N-[3-hydroxy-4-(1,3,4,12a-tetrahydro-6H-[1,4]oxazino[4,3-a][1,4]-benzodiazepin-11(12H)-yl-carbonyl)phenyl]benzamide;

(RS)-2-Methyl-N-[3-chloro-4-(1,3,4,12a-tetrahydro-6H-[1,4]oxazino[4,3-a][1,4]-benzodiazepin-11(12h)-yl-carbonyl)phenyl]benzamide;

(RS)-2-(4-Methyl-phenyl)-N-[3-chloro-4-(1,3,4,12a-tetrahydro-6H-[1,4]oxazino[4,3-a][1,4]-benzodiazepin-11(12H)-yl-carbonyl)phenyl]benzamide;

(RS)-2-Methyl-N-[4-(1,3,4,12a-tetrahydro-6H-[1,4]oxazino[4,3-a][1,4]-benzodiazepin-11(12H)-yl-carbonyl)phenyl]benzamide;

(RS)-2-Methyl-N-[3-methyl-4-(1,3,4,12a-tetrahydro-6H-[1,4]oxazino[4,3-a][1,4]-benzodiazepin-11(12H)-yl-carbonyl)phenyl]benzamide;

(RS)-2-(4-Methyl-phenyl)-N-[3-methyl-4-(1,3,4,12a-tetrahydro-6H-[1,4]oxazino[4,3-a][1,4]-benzodiazepin-11(12H)-yl-carbonyl)phenyl]benzamide;

(RS)-2-Phenyl-N-[3-methyl-4-(1,3,4,12a-tetrahydro-6H-[1,4]oxazino[4,3-a][1,4]-benzodiazepin-11(12H)-yl-carbonyl)phenyl]benzamide;

(RS)-2-(4-Methyl-phenyl)-N-[3-fluoro-4-(1,3,4,12a-tetrahydro-6H-[1,4]oxazino[4,3-a][1,4]-benzodiazepin-11(12H)-yl-carbonyl)phenyl]benzamide;

(RS)-2-Phenyl-N-[4-(8-methoxy-1,3,4,12a-tetrahydro-6H-[1,4]thiazino[4,3-a][1,4]-benzodiazepin-11(12H)-yl-carbonyl)phenyl]benzamide;

(RS)-2-Phenyl-N-[4-(8-fluoro-1,3,4,12a-tetrahydro-6H-[1,4]thiazino[4,3-a][1,4]-benzodiazepin-11(12H)-yl-carbonyl)phenyl]benzamide;

(RS)-2-Phenyl-N-[4-(9-chloro-1,3,4,12a-tetrahydro-6H-[1,4]thiazino[4,3-a][1,4]-benzodiazepin-11(12H)-yl-carbonyl)phenyl]benzamide;

(RS)-2-Phenyl-N-[4-(8,9-difluoro-1,3,4,12a-tetrahydro-6H-[1,4]thiazino[4,3-a][1,4]-benzodiazepin-11(12H)-yl-carbonyl)phenyl]benzamide;

(RS)-2-Phenyl-N-[4-(8-methyl-1,3,4,12a-tetrahydro-6H-[1,4]thiazino[4,3-a][1,4]-benzodiazepin-11(12H)-yl-carbonyl)phenyl]benzamide;

(RS)-2-Phenyl-N-[4-(8-chloro-1,3,4,12a-tetrahydro-6H-[1,4]thiazino[4,3-a][1,4]-benzodiazepin-11(12H)-yl-carbonyl)phenyl]benzamide;

(RS)-2-Phenyl-N-[3-chloro-4-(8-fluoro-1,3,4,12a-tetrahydro-6H-[1,4]thiazino[4,3-a][1,4]-benzodiazepin-11(12H)-yl-carbonyl)phenyl]benzamide;

(RS)-2-Phenyl-N-[4-(10-methyl-1,3,4,12a-tetrahydro-6H-[1,4]thiazino[4,3-a][1,4]-benzodiazepin-11(12H)-yl-carbonyl)phenyl]benzamide;

(RS)-3,5-Dimethyl-N-[3-chloro-4-(1,3,4,12a-tetrahydro-6H-[1,4]thiazino[4,3-a][1,4]-benzodiazepin-11(12H)-yl-carbonyl)phenyl]benzamide;

(RS)-2-Iodo-3-methyl-N-[3-chloro-4-(1,3,4,12a-tetrahydro-6H-[1,4]thiazino[4,3-a][1,4]-benzodiazepin-11(12H)-yl-carbonyl)phenyl]benzamide;

(RS)-3,5-Dichloro-N-[3-chloro-4-(1,3,4,12a-tetrahydro-6H-[1,4]thiazino[4,3-a][1,4]-benzodiazepin-11(12H)-yl-carbonyl)phenyl]benzamide;

(RS)-2-Methyl-3-iodo-N-[3-chloro-4-(1,3,4,12a-tetrahydro-6H-[1,4]thiazino[4,3-a][1,4]-benzodiazepin-11(12H)-yl-carbonyl)phenyl]benzamide;

(RS)-2-(2-Fluoro-phenyl)-N-[4-(1,3,4,12a-tetrahydro-6H-[1,4]thiazino[4,3-a][1,4]-benzodiazepin-11(12H)-yl-carbonyl)phenyl]benzamide;

(S)-2-Phenyl-N-[3-dimethylamino-4-(1,3,4,12a-tetrahydro-6H-[1,4]thiazino[4,3-a][1,4]-benzodiazepin-11(12H)-yl-carbonyl)phenyl]benzamide;

(S)-2-Phenyl-N-[3-chloro-4-(1,3,4,12a-tetrahydro-6H-[1,4]thiazino[4,3-a][1,4]-benzodiazepin-11(12H)-yl-carbonyl)phenyl]benzamide;

and pharmaceutically acceptable salts thereof.

35. The solid oral dosage form of claim 10 selected from the group consisting of (RS)-2-(3-Thienyl)-N-[4-(1,3,4,12a-tetrahydro-6H-[1,4]thiazino[4,3-a][1,4]-benzodiazepin-11(12H)-yl-carbonyl)phenyl]benzamide;

(RS)-2-(3-Thienyl)-N-[3-chloro-4-(1,3,4,12a-tetrahydro-6H-[1,4]thiazino[4,3-a][1,4]-benzodiazepin-11(12H)-yl-carbonyl)phenyl]benzamide;

(RS)-2-(3-Thienyl)-N-[3-fluoro-4-(1,3,4,12a-tetrahydro-6H-[1,4]thiazino[4,3-a][1,4]-benzodiazepin-11(12H)-yl-carbonyl)phenyl]benzamide;

(RS)-2-(2-Thienyl)-N-[4-(1,3,4,12a-tetrahydro-6H-[1,4]thiazino[4,3-a][1,4]-benzodiazepin-11(12H)-yl-carbonyl)phenyl]benzamide;

(RS)-2-(4-Methyl-2-thienyl)-N-[4-(1,3,4,12a-tetrahydro-6H-[1,4]thiazino[4,3-a][1,4]-benzodiazepin-11(12H)-yl-carbonyl)phenyl]benzamide;

(RS)-2-(4-Methyl-2-thienyl)-N-[4-(1,3,4,12a-tetrahydro-6H-[1,4]oxazino[4,3-a][1,4]-benzodiazepin-11(12H)-yl-carbonyl)phenyl]benzamide;

(RS)-2-Phenyl-N-[4-(1,3,4,12a-tetrahydro-2,2-dioxo-6H-[1,4]thiazino[4,3-a][1,4]-benzodiazepin-11(12H)-yl-carbonyl)phenyl]benzamide;

(RS)-2-Phenyl-N-[3-chloro-4-(1,3,4,12a-tetrahydro-2-methyl-6H-[1,4]pyrazino[4,3-a][1,4]-benzodiazepin-11(12H)-yl-carbonyl)phenyl]benzamide;

(RS)-2-Phenyl-N-[4-(1,3,4,12a-tetrahydro-2-benzyl-6H-[1,4]pyrazino[4,3-a][1,4]-benzodiazepin-11(12H)-yl-carbonyl)phenyl]benzamide;

(RS)-2-Phenyl-N-[4-(1,3,4,12a-tetrahydro-6H-[1,4]pyrazino[4,3-a][1,4]-benzodiazepin-11(12H)-yl-carbonyl)phenyl]benzamide;

(RS)-2-Phenyl-N-[4-(1,3,4,12a-tetrahydro-2-formyl-6H-[1,4]pyrazino[4,3-a][1,4]-benzodiazepin-11(12H)-yl-carbonyl)phenyl]benzamide;

(RS)-2-Phenyl-N-[3-chloro-4-(1,3,4,12a-tetrahydro-2-isopropyl-6H-[1,4]pyrazino[4,3-a][1,4]-benzodiazepin-11(12H)-yl-carbonyl)phenyl]benzamide;

(RS)-2-Methyl-N-[3-chloro-4-(1,3,4,12a-tetrahydro-2-methyl-6H-[1,4]pyrazino[4,3-a][1,4]-benzodiazepin-11(12H)-yl-carbonyl)phenyl]benzamide;

(RS)-2,3-Dimethyl-N-[3-chloro-4-(1,3,4,12a-tetrahydro-2-methyl-6H-[1,4]pyrazino[4,3-a][1,4]-benzodiazepin-11(12H)-yl-carbonyl)phenyl]benzamide;

(RS)-2,6-Dimethyl-N-[3-chloro-4-(1,3,4,12a-tetrahydro-2-methyl-6H-[1,4]pyrazino[4,3-a][1,4]-benzodiazepin-11(12H)-yl-carbonyl)phenyl]benzamide;

(RS)-2-(4-Methyl-phenyl)-N-[3-chloro-4-(1,3,4,12a-tetrahydro-2-methyl-6H-[1,4]pyrazino[4,3-a][1,4]-benzodiazepin-11(12H)-yl-carbonyl)phenyl]benzamide;

(RS)-2-(4-Methoxy-phenyl)-N-[3-chloro-4-(1,3,4,12a-tetrahydro-2-methyl-6H-[1,4]pyrazino[4,3-a][1,4]-benzodiazepin-11(12H)-yl-carbonyl)phenyl]benzamide;

(RS)-2-(3-Methoxy-phenyl)-N-[3-chloro-4-(1,3,4,12a-tetrahydro-2-methyl-6H-[1,4]pyrazino[4,3-a][1,4]-benzodiazepin-11(12H)-yl-carbonyl)phenyl]benzamide;

(RS)-2-Phenyl-N-[4-(1,3,4,12a-tetrahydro-2-methyl-6H-[1,4]pyrazino[4,3-a][1,4]-benzodiazepin-11(12H)-yl-carbonyl)phenyl]benzamide;

(RS)-2-Phenyl-N-[3-fluoro-4-(1,3,4, 12a-tetrahydro-2-methyl-6H-[1,4]pyrazino[4,3-a][1,4]-benzodiazepin-11(12H)-yl-carbonyl)phenyl]benzamide;

(RS)-2-Phenyl-N-[2-methoxy-4-(1,3,4,12a-tetrahydro-2-methyl-6H-[1,4]pyrazino[4,3-a][1,4]-benzodiazepin-11(12H)-yl-carbonyl)phenyl]benzamide;

(RS)-2-(4-,Methyl-phenyl)-N-[2-methoxy-4-(1,3,4,12a-tetrahydro-2-methyl-6H-[1,4]pyrazino[4,3-a][1,4]-benzodiazepin-11(12H)-yl-carbonyl)phenyl]benzamide;

(RS)-2-(4-Methyl-phenyl)-N-[3-trifluoromethyl-4-(1,3,4,12a-tetrahydro-2-methyl-6H-[1,4]pyrazino[4,3-a][1,4]-benzodiazepin-11(12H)-yl-carbonyl)phenyl]benzamide;

(RS)-2-(4-Methyl-phenyl)-N-[2-methyl-4-(1,3,4,12a-tetrahydro-2-methyl-6H-[1,4]pyrazino[4,3-a][1,4]-benzodiazepin-11(12H)-yl-carbonyl)phenyl]benzamide;

(RS)-2-Methyl-N-[3-methoxy-4-(1,3,4,12a-tetrahydro-2-methyl-6H-[1,4]pyrazino[4,3-a][1,4]-benzodiazepin-11(12H)-yl-carbonyl)phenyl]benzamide;

(RS)-2-Phenyl-N-[3-methoxy-4-(1,3,4,12a-tetrahydro-2-methyl-6H-[1,4]pyrazino[4,3-a][1,4]-benzodiazepin-11(12H)-yl-carbonyl)phenyl]benzamide;

(RS)-2-(4-Methyl-phenyl)-N-[3-methoxy-4-(1,3,4,12a-tetrahydro-2-methyl-6H-[1,4]pyrazino[4,3-a][1,4]-benzodiazepin-11(12H)-yl-carbonyl)phenyl]benzamide;

(RS)-2-Methyl-N-[4-(1,3,4,12a-tetrahydro-2-methyl-6H-[1,4]pyrazino[4,3-a][1,4]-benzodiazepin-11(12H)-yl-carbonyl)phenyl]benzamide;

(RS)-2-Phenyl-N-[3-methyl-4-(1,3,4,12a-tetrahydro-2-methyl-6H-[1,4]pyrazino[4,3-a][1,4]-benzodiazepin-11(12H)-yl-carbonyl)phenyl]benzamide;

(RS)-2-Phenyl-N-[3-chloro-4-(1,3,4,12a-tetrahydro-2-(2,2,2-trifluoroethyl)-6H-[1,4]pyrazino[4,3-a][1,4]-benzodiazepin-11(12H)-yl-carbonyl)phenyl]benzamide;

(RS)-2,3,4,5-Tetrafluoro-N-[3-chloro-4-(1,3,4,12a-tetrahydro-2-methyl-6H-[1,4]pyrazino[4,3-a][1,4]-benzodiazepin-11(12H)-yl-carbonyl)phenyl]benzamide;

(RS)-2-Methyl-5-fluoro-N-[3-chloro-4-(1,3,4,12a-tetrahydro-2-methyl-6H-[1,4]pyrazino[4,3-a][1,4]-benzodiazepin-11(12H)-yl-carbonyl)phenyl]benzamide;

(RS)-2-Methyl-3-chloro-N-[3-chloro-4-(1,3,4,12a-tetrahydro-2-methyl-6H-[1,4]pyrazino[4,3-a][1,4]-benzodiazepin-11(12H)-yl-carbonyl)phenyl]benzamide;

(RS)-2,3-Dichloro-N-[3-chloro-4-(1,3,4,12a-tetrahydro-2-methyl-6H-[1,4]pyrazino[4,3-a][1,4]-benzodiazepin-11(12H)-yl-carbonyl)phenyl]benzamide;

(RS)-2,6-Dichloro-N-[3-chloro-4-(1,3,4,12a-tetrahydro-2-methyl-6H-[1,4]pyrazino[4,3-a][1,4]-benzodiazepin-11(12H)-yl-carbonyl)phenyl]benzamide;

(RS)-2-Phenyl-5-fluoro-N-[3-chloro-4-(1,3,4,12a-tetrahydro-2-methyl-6H-[1,4]pyrazino[4,3-a][1,4]-benzodiazepin-11(12H)-yl-carbonyl)phenyl]benzamide;

(RS)-2-Methyl-3-fluoro-N-[3-chloro-4-(1,3,4,12a-tetrahydro-2-methyl-6H-[1,4]pyrazino[4,3-a][1,4]-benzodiazepin-11(12H)-yl-carbonyl)phenyl]benzamide;

(RS)-2-Phenyl-5-fluoro-N-[3-chloro-4-(1,3,4,12a-tetrahydro-6H-[1,4]thiazino[4,3-a][1,4]-benzodiazepin-11(12H)-yl-carbonyl)phenyl]benzamide;

(RS)-2-Phenyl-4-fluoro-N-[3-chloro-4-(1,3,4,12a-tetrahydro-6H-[1,4]thiazino[4,3-a][1,4]-benzodiazepin-11(12H)-yl-carbonyl)phenyl]benzamide;

(RS)-2-Phenyl-N-[3-fluoro-4-(1,3,4,12a-tetrahydro-6H-[1,4]thiazino[4,3-a][1,4]-benzodiazepin-11(12H)-yl-carbonyl)phenyl]benzamide;

(RS)-2-Phenyl-N-[3-methyl-4-(1,3,4,12a-tetrahydro-6H-[1,4]thiazino[4,3-a][1,4]-benzodiazepin-11(12H)-yl-carbonyl)phenyl]benzamide;

(RS)-2-Phenyl-N-[3-methoxy-4-(1,3,4,12a-tetrahydro-6H-[1,4]thiazino[4,3-a][1,4]-benzodiazepin-11(12H)-yl-carbonyl)phenyl]benzamide;

(RS)-2-Phenyl-N-[3-hydroxy-4-(1,3,4,12a-tetrahydro-6H-[1,4]thiazino[4,3-a][1,4]-benzodiazepin-11(12H)-yl-carbonyl)phenyl]benzamide;

(RS)-2-Methyl-5-fluoro-N-[3-chloro-4-(1,3,4,12a-tetrahydro-6H-[1,4]oxazino[4,3-a][1,4]-benzodiazepin-11(12H)-yl-carbonyl)phenyl]benzamide;

(RS)-2-Phenyl-5-fluoro-N-[3-chloro-4-(1,3,4,12a-tetrahydro-6H-[1,4]oxazino[4,3-a][1,4]-benzodiazepin-11(12H)-yl-carbonyl)phenyl]benzamide;

(RS)-2-(4-Methoxy-phenyl)-N-[3-chloro-4-(1,3,4,12a-tetrahydro-6H-[1,4]oxazino[4,3-a][1,4]-benzodiazepin-11(12H)-yl-carbonyl)phenyl]benzamide;

(RS)-2-(3-Methoxy-phenyl)-N-[3-chloro-4-(1,3,4,12a-tetrahydro-6H-[1,4]oxazino[4,3-a][1,4]-benzodiazepin-11(12H)-yl-carbonyl)phenyl]benzamide;

(RS)-2-Phenyl-4-fluoro-N-[3-chloro-4-(1,3,4,12a-tetrahydro-6H-[1,4]oxazino[4,3-a][1,4]-benzodiazepin-11(12H)-yl-carbonyl)phenyl]benzamide;

(RS)-2-Phenyl-4-methoxy-N-[3-chloro-4-(1,3,4,12a-tetrahydro-6H-[1,4]oxazino[4,3-a][1,4]-benzodiazepin-11(12H)-yl-carbonyl)phenyl]benzamide;

(RS)-2-Phenyl-5-methoxy-N-[3-chloro-4-(1,3,4,12a-tetrahydro-6H-[1,4]oxazino[4,3-a][1,4]-benzodiazepin-11(12H)-yl-carbonyl)phenyl]benzamide;

and pharmaceutically acceptable salts thereof.

36. A method of treating a condition selected from hypertension, congestive heart failure, cardiac insufficiency, coronary vasospasm, cardiac ischemia, liver cirrhosis, renal vasospasm, renal failure, cerebral edema and ischemia, stroke, thrombosis, or water retention in a subject in need thereof comprising administering to the subject a therapeutically effective amount of the compound of claim 1.

37. The method of claim 36, wherein the condition is congestive heart failure.

38. The method of claim 36, wherein the therapeutically effective amount of the compound is about 0.1 to about 300 mg/kg/day.

39. A method of treating a condition selected from hypertension, congestive heart failure, cardiac insufficiency, coronary vasospasm, cardiac ischemia, liver cirrhosis, renal vasospasm, renal failure, cerebral edema and ischemia, stroke, thrombosis, or water retention in a subject in need thereof comprising administering to the subject a therapeutically effective amount of the compound of claim 10.

40. The method of claim 39, wherein the condition is congestive heart failure.

41. The method of claim 39, wherein the therapeutically effective amount of the compound is about 0.1 to about 300 mg/kg/day.

42. A method of treating a condition selected from hypertension, congestive heart failure, cardiac insufficiency, coronary vasospasm, cardiac ischemia, liver cirrhosis, renal vasospasm, renal failure, cerebral edema and ischemia, stroke, thrombosis, or water retention in a subject in need thereof comprising administering to the subject a therapeutically effective amount of the compound of claim 6.

43. The method of claim 42, wherein the condition is congestive heart failure.

44. The method of claim 42, wherein the therapeutically effective amount of the compound is about 0.1 to about 300 mg/kg/day.

45. The solid dosage form of claim 34 wherein the compound is (S)-2-Phenyl-N-[3-chloro-4-(1,3,4,12a-tetrahydro-6H-[1,4]oxazino[4,3-a][1,4]-benzodiazepin-11(12H)-yl-carbonyl)phenyl]benzamide and pharmaceutically acceptable salts thereof.

46. The solid dosage form of claim 35 wherein the compound is (RS)-2-Phenyl-N-[3-chloro-4-(1,3,4,12a-tetrahydro-2-methyl-6H-[1,4]pyrazino[4,3-a][1,4]-benzodiazepin-11(12H)-yl-carbonyl)phenyl]benzamide and pharmaceutically acceptable salts thereof.

* * * * *